United States Patent
Slijkhuis et al.

(10) Patent No.: US 6,171,836 B1
(45) Date of Patent: Jan. 9, 2001

(54) PROCESS FOR OXIDATION OF STEROIDS AND GENETICALLY ENGINEERED CELLS USED THEREIN

(75) Inventors: Herman Slijkhuis, Berkel en Rodenrijs; Eric Bastiaan Smaal, Delft; Gerardus Cornelis Maria Selten, Berkel en Rodenrijs, all of (NL)

(73) Assignee: Hoechst Marion Roussel(FR)

( * ) Notice: Under 35 U.S.C. 154(b), the term of this patent shall be extended for 0 days.

(21) Appl. No.: 09/099,011

(22) Filed: Jun. 17, 1998

Related U.S. Application Data

(60) Division of application No. 08/418,085, filed on Apr. 6, 1995, now Pat. No. 5,869,283, which is a continuation-in-part of application No. 08/054,185, filed on Apr. 26, 1993, now abandoned, which is a continuation of application No. 07/474,857, filed on Oct. 30, 1990, now abandoned, and a continuation of application No. 08/002,608, filed on Jan. 11, 1993, now abandoned, which is a continuation of application No. 07/474,798, filed on Jul. 16, 1990, now abandoned.

(30) Foreign Application Priority Data

| May 6, 1988 | (NL) | 88200904 |
| Sep. 23, 1988 | (NL) | 88202080 |
| Sep. 25, 1989 | (NL) | PCT/NL89/0072 |

(51) Int. Cl.[7] ............ C12N 9/02; C12N 15/00; C12N 5/00; C12N 1/20; C12P 21/06

(52) U.S. Cl. ............ 435/189; 435/69.1; 435/320.1; 435/325; 435/252.3; 435/254.2; 536/23.1; 536/23.2

(58) Field of Search .............. 435/69.1, 320.1, 435/325, 189, 252.3, 254.2; 536/23.1, 23.2

(56) References Cited

U.S. PATENT DOCUMENTS

| 4,943,529 | * | 7/1990 | Van Den Berg et al. | 435/172.3 |
| 5,137,822 | * | 8/1992 | Yabusaki et al. | 435/193 |

OTHER PUBLICATIONS

White, P. et al., Proc. Natl. Acad. Sci. USA, vol. 81, pp. 1986–1990, Apr. 1984.*

Malpartida, F. et al., Nature, vol. 309, pp. 462–464, May 1984.*

* cited by examiner

Primary Examiner—Ponnathapu Achutamurthy
Assistant Examiner—Peter P. Tung
(74) Attorney, Agent, or Firm—Bierman, Muserlian and Lucas

(57) ABSTRACT

An expression cassette, operable in a recombinant host, comprising a heterologous DNA coding sequence encoding a protein, which is functional, alone or in cooperation with one or more additional proteins, of catalyzing an oxidation step in the biological pathway for conversion of cholesterol into hydrocortisone, which step is selected from the group consisting of:

the conversion of cholesterol to pregnenolone;

the conversion of pregnenolone to progesterone;

the conversion of progesterone to 17α-hydroxyprogesterone;

the conversion of 17α-hydroxyprogesterone to cortexolone;

the conversion of cortexolone to hydrocortisone, and the corresponding control sequences effective in said host.

19 Claims, 52 Drawing Sheets

```
AATTCACCTC GAAAGGAAGC TGATAAACCG ATACAATTAA AGGCTCCTTT TTTTTTGGAG ATTTTCAACG TGAAAAAATT
         30                                  60                                  90
ATTATTCGCA ATTCCAAGCT AATTCACCTC GAAAGCAAGC TGATAAACCG AATACAATTAA AGGCTCCTTT TGGAGCCTTT TTTTTTGGAG
         120                                 150                                 180
ATTTTCAACG TGAAAAAATT ATTATTCGCA ATTCCAAGCT CTGCCTCGCG CGTTTCGGTG ATGACGGTGA AAACCTCTGA CACATGCAGC
         210                                 240                                 270
TCCCGGAGAC GGTCACAGCT TGTCTGTAAG CGGATGCAGA TCACGCGCCC TGTAGCGGCG CATTAAGCGC GGCGGGTGTG GTGGTTACGC
         300                                 330                                 360
GCAGCGTGAC CGCTACACTT GCCAGCGCCC TAGCGCCCGC TCCTTTCGCT TTCTTCCCTT CACGTTCGCC GGCTTTCCCC
         390                                 420                                 450
GTCAAGCTCT AAATCGGGGG CTCCCTTTAG GGTTCCGATT TAGTGCTTTA CGGCACCTCG ACCCCAAAAA ACTTGATTAG GGTGATGGTT
         480                                 510                                 540
CACGTAGTGG GCCATCGCCC TGATAGACGG TTTTTCGCCC TTTGACGTTG GAGTCCACGT TCTTTAATAG TGGACTCTTG TTCCAAACTG
         570                                 600                                 630
GAACAACACT CAACCCTATC TCGGTCTATT CTTTTGATTT ATAAGGGATT TTGCCCGATTT CGGCCTATTG GTTAAAAAAT GAGCTGATTT
         660                                 690                                 720
AACAAAAAAT TAACGCGAAT TTTAACAAAA TATTAACGTT TACAATTTGA TCTGCGCTCG GTCGTTCGGC GGTATCAGCT
         750                                 780                                 810
CACTCAAAGG CGGTAATACG GTTATCCACA GAATCAGGGG ATAACGCAGG AAAGAACATG TGAGCAAAAG GCCAGCAAAA GGCCAGGAAC
         840                                 870                                 900
CGTAAAAAGG CCGCGTTGCT GGCGTTTTTC CATAGGCTCC GCCCCCCTGA CGAGCATCAC AAAAATCGAC GCTCAAGTCA GAGGTGGCGA
         930                                 960                                 990
AACCCGACAG GACTATAAAG ATACCAGGCG TTTCCCCCTG GAAGCTCCCT CGTGCGCTCT CCTGTTCCGA CCCTGCCGCT TACCGGATAC
         1020                                1050                                1080
```

FIG. 5A

```
                    1110                 1140                               1170
CTGTCCGCCT TTCTCCCTTC GGGAAGCCGTG GCGCTTTCTC ATAGCTCACG CTGTAGGTAT CTCAGTTCGG TGTAGGTCGT TCGCTCCAAG
                    1200                 1230                               1260
CTGGGCTGTG TGCACGAACC CCCCGTTCAG CCCGACCGCT GGGCCTTATC CGGTAACTAT CGTCTTGAGT CCAACCCGGT AAGACACGAC
                    1290                 1320                               1350
TTATCGCCAC TGGCAGCAGC CACTGGTAAC AGGATTAGCA GAGCGAGGTA TGTAGGCGGT GCTACAGAGT TCTTGAAGTG GTGGCCTAAC
                    1380                 1410                               1440
TACGGCTACA CTAGAAGGAC AGTATTTGGT ATCTGCGCTC TGCTGAAGCC AGTTACCTTC GGAAAAAGAG TTGGTAGCTC TTGATCCCGC
                    1470                 1500                               1530
AAACAAACCA CCGCTGGTAG CGGTGGTTTT TTTGTTTGCA AGCAGCAGAT TACGCGCAGA AAAAAAGGAT CTCAAGAAGA TCCTTTGATC
                    1560                 1590                               1620
TTTTCTACGG GGTCTGACGC TCAGTGGAAC GAAAACTCAC GTTAAGGGAT TTTGGTCATG AGATTATCAA AAAGGATCTT CACCTAGATC
                    1650                 1680                               1710
CTTTTAAATT AAAAATGAAG TTTTAAATCA ATCTAAAGTA TATATGAGTA AACTTGGTCT GACAGTTACC AATGCTTAAT CAGTGAGGCA
                    1740                 1770                               1800
CCTATCTCAG CGATCTGTCT ATTTCGTTCA TCCATAGTTG CCTGACTCCC CGTCGTGTAG ATAACTACGA TACGGGAGGG CTTACCATCT
                    1830                 1860                               1890
GGCCCCAGTG CTGCAATGAT ACCGCGAGAC CCACGCTCAC CGGCTCCAGA TTTATCAGGA ATAAACCAGC CAGCCGGAAG GGCCGAGCGC
                    1920                 1950                               1980
AGAAGTGGTC CTGCAACTTT ATCCGCCTCC ATCCAGTCTA TTAATTGTTG CCGGGAAGCT AGAGTAAGTA GTTCGCCAGT TAATAGTTTG
                    2010                 2040                               2070
CGCAACGTTG TTGCCATTGC TGCAGGCATC GTGGTGTCAC GCTCGTCGTT TGGTATGGCT TCATTCAGCT CCGGTTCCCA ACGATCAAGG
```

FIG. 5B

```
                2100                    2130                    2160
CGAGTTACAT GATCCCCCAT GTTGTGCAAA AAAGCGGTTA GCTCCTTCGG TCCTCCGATC GTTGTCAGAA GTAAGTTGCC CGCAGTGTTA
                2190                    2220                    2250
TCACTCATGG TTATGGCAGC ACTGCATAAT TCTCTTACTG TCATGCCATC CGTAAGATGC TTTTCTGTGA CTGGTGAGTA CTCAACCAAG
                2280                    2310                    2340
TCATTCTGAG AATAGTGTAT GCGGCGACCG AGTTGCTCTT GCCCGGCGTC AACACGGGAT AATACCGCGC CACATAGCAG AACTTTAAAA
                2370                    2400                    2430
GTGCTCATCA TTGGAAAACG TTCTTCGGGG CGAAAACTCT CAAGGATCTT ACCGCTGTTG AGATCCAGTT CGATGTAACC CACTCGTGCA
                2460                    2490                    2520
CCCAACTGAT CTTCAGCATC TTTTACTTTC ACCAGCGTTT CTGGGTGAGC AAAAACAGGA AGGCAAAATG CCGCAAAAAA GGGAATAAGG
                2550                    2580                    2610
GCGACACGGA AATGTTGAAT ACTCATACTC TTCCTTTTTC AATATTATTG AAGCATTTATC TTTTATTGTT CATGATGATA TATTTTTATC
                2640                    2670                    2700
TTGTGCAATG TAACATCAGA GATTTTGAGA CACAACGTGG CTTTGTTGAA TAAATCGAAC TTTTGCTGAG TTGACTCCCC GCGGCGCGATG
                2730                    2760                    2790
GGTCGAATTT GCTTTCGAAA AAAAAGCCCG CTCATTAGGC GGGCTAAAAA AAAGCCCGCT CATTAGGCGG GCTCGAATTT CTGCCATTCA
                2820                    2850                    2880
TCCGCTTATT ATCACTTATT CAGGCGTAGC AACCAGGCGT TTAAGGGCAC CAATAACTGC CTTAAAAAAA TTACGCCCCG CCCTGCCACT
                2910                    2940                    2970
CATCGCAGTA CTGTTGTAAT TCATTAAGCA TTCTGCCGAC ATGGAAGCCA TCACAGACGG CATGATGAAC CTGAATCGCC AGCGGCATCA
```

FIG. 5C

```
GCACCTTGTC GCCTTGCGTA TAATATTTGC CCATAGTGAA AACGGGGGCG AAGAAGTTGT CCATATTCGC CACGTTTAAA TCAAAACTGG
                     3000                 3030                 3060
TGAAACTCAC CCAGGGATTG GCTGAGACGA AAAACATATT CTCAATAAAC CCTTTAGGGA AATAGGCCAG GTTTTCACCG TAACACGCCA
                     3090                 3120                 3150
CATCTTGCGA ATATATGTGT AGAAACTGCC GGAAATCGTC GTGGTATTCA CTCCAGAGCG ATGAAAACGT TTCAGTTTGC TCATGAAAAA
                     3180                 3210                 3240
CGGTGTAACA AGGGTGAACA CTATCCCATA TCACCAGCTC ACCGTCTTTC ATTGCCATAC GAAATTCCGG ATGAGCATTC ATCAGGCGGG
                     3270                 3300                 3330
CAAGAATGTG AATAAAGGCC GGATAAAAACT TGTGCTTATT TTTCTTTAAA GTCTTTAAAA AGGCCCGTAAT ATCCAGCTAA ACGGTCTGGT
                     3360                 3390                 3420
TATAGGTACA TTGAGCAACT GACTGAAATG CCTCAAAAATG TTCTTTACGA TGCCATTGGG ATATATCAAC GGTGGTATAT CCAGTGATTT
                     3450                 3480                 3510
TTTTCTCCAT TTTAGCTTCC TTAGCTCCTG AAAATCTCGA TAACTCAAAA AATACGCCCG GTAGTGATCT TATTTCATTA TGGTGAAAGT
                     3540                 3570                 3600
TGGAACCTCT TACGTGCCGA TCAACGTCTC ATTTTCGCCA AAAGTTGGCC CAGGGCTTCC CGGTATCAAC AGGGACACCA GGATTTATTT
                     3630                 3660                 3690
ATTCTGCGAA GTGATCTTCC GTCACAGGTA TTTATTCGAA GACGAAAGGG CATCGCGCGC GGGGAATTCC CGGGAGAGCT CGATATCGCA
                     3720                 3750                 3780
TGCGGTACCT CTAGAAGAAG CTTGGAGACA AGTAAAAGGA TAAAACAGCA CAATTCCAAG AAAAACACGA TTTAGAACCT AAAAAGAACG
                     3810                 3840                 3870
AATTTGAACT AACTCATAAC AAAAAGAACG AAGTCGAGAT CAGGGAATGA GTTTATAAAA TAAAAAAAGC ACCTGAAAAG
                     3900                 3930                 3960
```

FIG. 5D

```
              3990                          4020                                              4050
GTGTCTTTTT TTGATGGTTT TGAACTTGTT CTTTCCTTATC TTGATACATA TAGAAATAAC GTCATTTTTA TTTTAGTTGC TGAAAGGTGC
         4080                          4110                                                  4140
GTTGAAGTGT TGGTATGTAT GTGTTTTAAA GTATTGAAAA CCCTTAAAAT TGGTTGCACA GAAAAACCCC ATCTGTTAAA GTTATAAGTG
                   4170                          4200                                        4230
ACTAAACAAA TAACTAAAATA GATGGGGGTT TCTTTTAATA TTATGTGTCC ATTTATTCAG ATGAAAAATC AAGGGTTTTA
              4260                          4290                                             4320
GTGGACAAGA CAAAAAGTGG AAAAGTGAGA CCATGGAGAG AAAAGAAAAT CGCTAATGTT GATTACTTTG AACTTCTGCA TATTCTTGAA
         4350                          4380                                                  4410
TTTAAAAAGG CTGAAAGAGT AAAAGATTGT GCTGAAATAT ACAAAATCGT GAAACAGGCG AAAGAAAGTT GTATCGAGTG
                   4440                          4470                                        4500
TGGTTTTGTA AATCCAGGCT TTGTCCAATG TGCAACTGGA GGAGAGCAAT GAAACATGGC ATTCAGTCAC AAAAGGTTGT TGCTGAAGTT
              4530                          4560                                             4590
ATTAAACAAA AGCCAACAGT TCGTTGGTTG TTTCTCACAT TAACAGTTAA AAATGTTTAT GATGGCGAAG AATTAAATAA GAGTTTGTCA
         4620                          4650                                                  4680
GATATGGCTC AAGGATTTCG CCGAATGATG CAATATAAAA AAATTAATAA AAATCTTGTT GGTTTTATGC GTGCAACGGA AGTGACAATA
                   4710                          4740                                        4770
AATAATAAAG ATAATTCTTA TAATCAGCAC ATGCATGTAT TGGTATGTGT GGAACCAACT TATTTTAAGA ATACAGAAAA CTACGTGAAT
              4800                          4830                                             4860
CAAAAACAAT GGATTCAATT TTGGAAAAAG GCAATGAAAT TAGACTATGA TCCAAATGTA AAAGTTCAAA TGATTCGACC GAAAAATAAA
         4890                          4920                                                  4950
TATAAATCGG ATATACAAATC GGCAATTGAC GAAACTGCAA AATATCCTGT AAAGGATACG GATTTTATGA CCGATGATGA AGAAAAGAAT
                   4980                          5010                                        5040
TTGAAACGTT TGTCTGATTT GGAGGAAGGT TTACACCGTA AAAGGTTAAT CTCCTATGGT GGTTTGTTAA AAGAAATACA TAAAAAATTA
```

FIG. 5E

```
                              5070                              5100                              5130
AACCCTTGATG ACACAGAAGA AGGCGATTTG ATTCATACAG ATGATGACGA AAAAGCCGAT GAAGATGGAT TTTCTATTAT TGCAATGTGG
                              5160                              5190                              5220
AATTGGGAAC GGAAAAATTA TTTTATTAAA GAGTAGTTCA ACAAACGGGC CAGTTGTTG AAGATTAGAT GCTATAATTG TTATTAAAAG
                              5250                              5280                              5310
GATTGAAGGA TGCTTAGGAA GACGAGTTAT TAATAGCTGA ATAAGAACGG TGCTCTCCAA ATATTCTTAT TTAGAAAAGC AAATCTAAAA
                              5340                              5370                              5400
TTATCTGAAA AGGGAATGAG AATAGTGAAT GGACCAATAA TAATGACTAG AGAAGAAAGA ATGAAGATTG TTCATGAAAT TAAGGAACGA
                              5430                              5460                              5490
ATATTGGATA AATATGGGGA TGATGTTAAG GCTATTGGTG TCTTGGTCGT CAGACTGATG GGCCCTATTC GGATATTGAG
                              5520                              5550                              5580
ATGATGTGTG TCATGTCAAC AGAGGAAGCA GAGTTCAGCC ATGAATGGAC AACCGGTGAG TGGAAGGTGG AAGTGAATTT TGATAGCGAA
                              5610                              5640                              5670
GAGATTCTAC TAGATTATGC ATCTCAGGTG GAATCAGATT GGCCGCTTAC ACATGGTCAA TTTTTCTCTA TTTTGCCGAT TTATGATTCA
                              5700                              5730                              5760
GGTGGATACT TAGAGAAAGT GTATCAAACT GCTAAATCGG TAGAAGCCCA AACGTTCCAC GATGCGGATTT GTGCCCTTAT CGTAGAAGAG
                              5790                              5820                              5850
CTGTTTGAAT ATGCAGGCAA ATGGCGTAAT ATTCGTGTGC AAGGACCGAC AACATTCTA CCATCCTTGA ACTGAAGCAG AGCAATGGCA
                              5880                              5910                              5940
GGTGCCATGT TGATTGGTCT GCATCATCGC ATCTGTTATA CGACGAGCGC TTCGGTCTTA ACTGAAGCAG TTAAGCAATC AGATCTTCCT
                              5970                              6000                              6030
TCAGGTTATG ACCATCTGTG ATGTCTTCGTA AACTTCCGA CTCTGAGAAA CTTCTGGAAT CGCTAGAGAA TTTCTGGAAT
                              6060                              6090                              6120
GGGATTCAGG AGTGGACAGA ACGACACGGA TATATAGTGG ATGTGTCAAA ACGCATACCA TTTTGAACGA TGACCTCTAA TAATTGTTAA
```

FIG. 5F

```
      6150                    6180                    6210
TCATGTTGGT TACGTATTTA TTAACTTCTC CTAGTATTAG TAATTATCAT GGCTGTCATG GCCCATTAAC GGAATAAAGG GTGTGCTTAA
      6240                    6270                    6300
ATCGGGCCAT TTTGCGTAAT AAGAAAAAGG ATTAATTATG AGCGAATTGA AGTAATAATA TTTACATTAG AAAATGAAAG
      6330                    6360                    6390
GGGATTTTAT GCGTGAGAAT GTTACAGTCT ATCCCGGGCAT TGCCAGTCGG GGATATTAAA AAGAGTATAG GTTTTTATTG CGATAAACTA
      6420                    6450                    6480
GGTTTCACTT TGGTTCACCA TGAAGATGGA TTCGCAGTTC TAATGTGTAA TGAGGTTCGG ATTCATCTAT GGGAGGCAAG TGATGAAGGC
      6510                    6540                    6570
TGGCGCCTCTC GTAGTAATGA TTCACCGGTT TGTACAGGTG CGGAGTCGTT TATTGCTGGT ACTGCTAGTT GCCGCATTGA AGTAGAGGGA
      6600                    6630                    6660
ATTGATGAAT TATATCAACA TATTAAGCCT TTGGGCATTT TGCACCCCAA TACATCATTA AAAGATCAGT GGTGGGATGA ACGAGACTTT
      6690                    6720                    6750
GCAGTAATTG ATCCCGACAA CAATTTGATT AGCTTTTTTC AACAAATAAA AAGCTAAAAT CTATTATTAA TCTGTTCAGC AATCGGGCGC
      6780                    6810                    6840
GATTGCTGAA TAAAAGATAC GAGAGACCTC TCTTGTATCT TTTTTATTTT GAGTGGTTTT GTCCGTTACA CTAGAAAAACC GAAAGACAAT
      6870                    6900                    6930
AAAAATTTTA TTCTTGCTGA GTCTGGCTTT CGGTAAGCTA GACAAAACGG ACAAAATAAA AATTGGCAAG GGTTTAAAGG TGGAGATTTT
      6960                    6990                    7020
TTGAGTGATC TTCTCAAAAA ATACTACCTG TCCCTTGCTG ATTTTTAAAC GAGCACGAGA GCAAAACCCC CCTTTGCTGA GGTGGCAGAG
      7050                    7080                    7110
GGCAGGTTTT TTTGTTTCTT TTTTCTCGTA AAAAAAAGAA AGGTCTTAAA GGTTTTATGG TTTTGGTCGG CACTGCCGAC AGCCTCGCAG
      7140                    7170                    7200
GACACACACT TTATGAATAT AAAGTATAGT GTGTTATACT TTACTTGGAA GTGGTTGCCG GAAAGAGCGA AAATGCCTCA CATTTGTGCC
      7230                    7260                    7290
ACCTAAAAAG GAGCGATTTA CATATGAGTT ATGCAGTTTG TAGAATGCAA AAAGTGAAAT CAGGGGGATC CTCTAGAGTC GAGCTCAAGC
      7320
TAGCTTGGTA CGTACCAGAT CTGAGATCAC GCGTTCTAGA GGTCGA
```

FIG. 5G

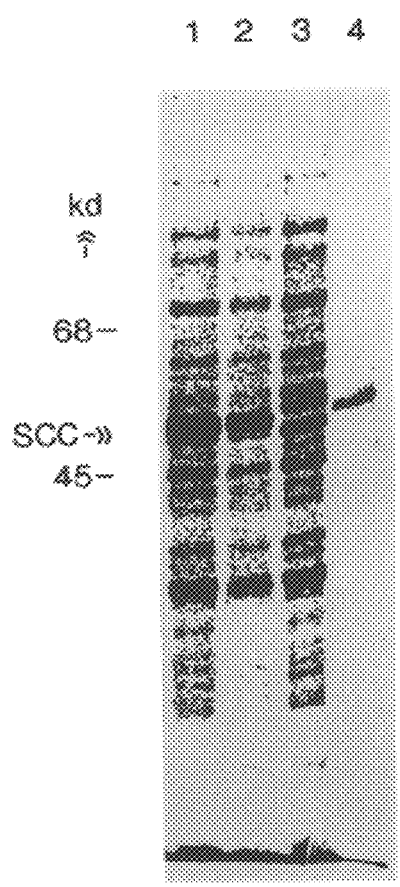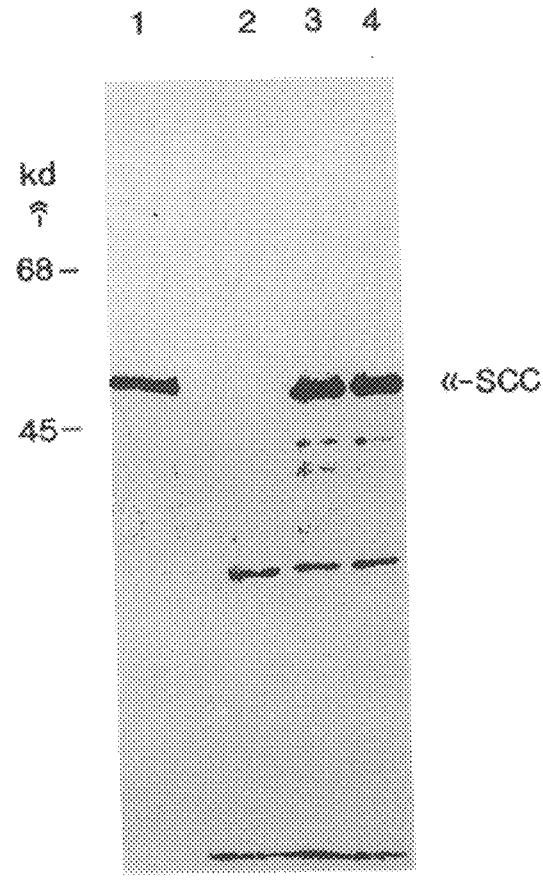
FIG. IIA  FIG. IIB

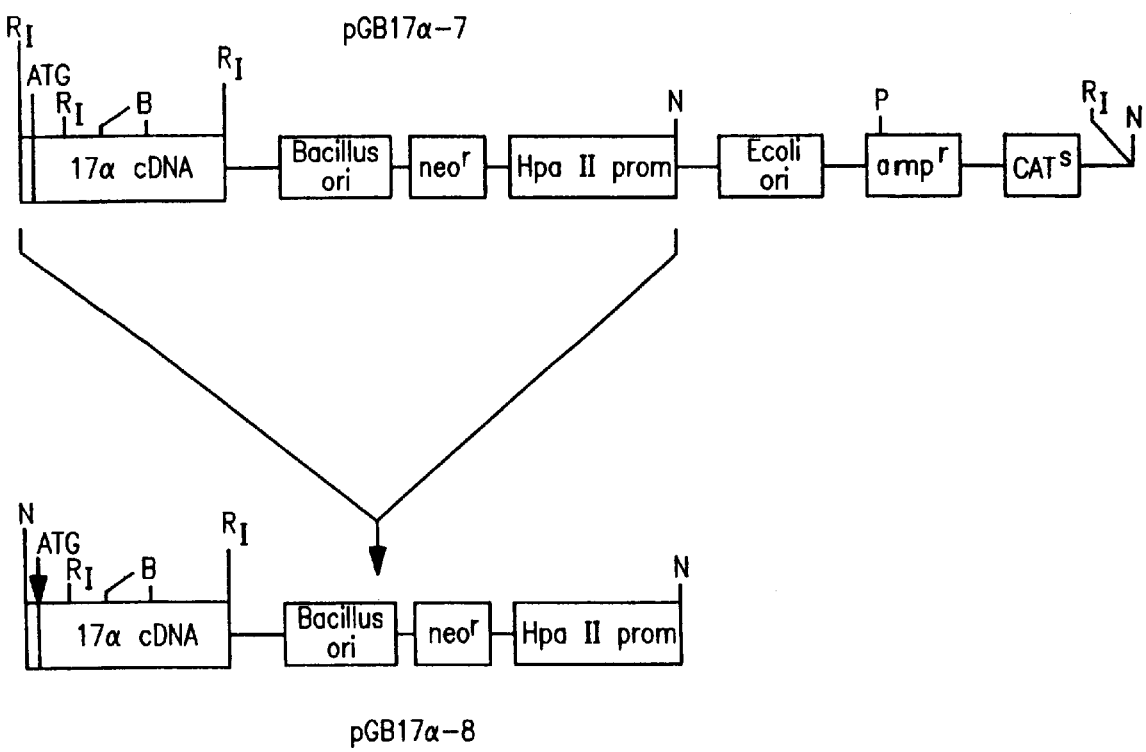
FIG. 27
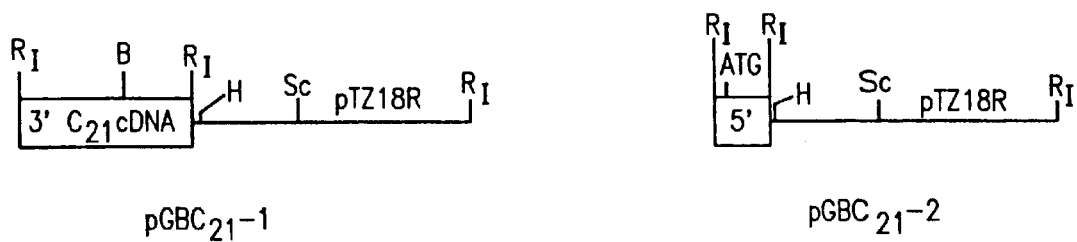
FIG. 28A
FIG. 28B

PROCESS FOR OXIDATION OF STEROIDS AND GENETICALLY ENGINEERED CELLS USED THEREIN

PRIOR APPLICATIONS

This application is a division of U.S. application Ser. No. 08/418,085 filed Apr. 6, 1995, now U.S. Pat. No. 5,869,283 which is a continuation-in-part of U.S. patent application Ser. No. 08/054,185 filed Apr. 26, 1993, now abandoned, which is a continuation of U.S. patent application Ser. No. 07/474,857 filed Oct. 30, 1990, now abandoned and U.S. patent application Ser. No. 08/002,608 filed Jan. 11, 1993, now abandoned, which is a continuation of U.S. patent application Ser. No. 07/474,798 filed Jul. 16, 1990, now abandoned.

STATE OF THE ART $\Delta^4$-pregnene-11$\beta$, 17$\alpha$, 21-triol-3,20-dione (hydrocortisone) is an important pharmaceutical steroid, used for its pharmacological properties as a corticosteroid and as a starting compound for the preparation of numerous useful steroids, particularly other corticosteriods. Hydrocortisone is produced in the adrenal cortex of vertebrates and was originally obtained, in small amounts only, by a laborious extraction from adrenal cortex tissue. Only after structure elucidation were new production routes developed, characterized by a combination of chemical synthesis steps and microbiological conversions. Only because the starting compounds which are employed such as sterols, bile acids and sapogenins are abundant and cheap, the present processes afford a less expensive product, but these still are rather complicated. Several possibilities were envisaged to improve the present processes, and also biochemical approaches have been tried.

One attempt was to have a suitable starting steroid converted in an in vitro biochemical system using the isolated adrenal cortex proteins which are known to be responsible for the enzymatical conversion in vivo of steroids to hydrocortisone. However, the difficult isolation of the proteins and the high price of the necessary cofactors, appeared to be prohibitive for an economically attractive large scale process.

Another approach was to keep the catalyzing proteins in their natural environment and to have the adrenal cortex cells produce the desired hydrocortisone in a cell culture. But due to the low productivity of the cells, in practice, it appeared to be impossible to make such a biochemical process economically attractive.

The in vivo process in the adrenal cortex of mammals and other vertebrates constitutes a biochemical pathway, which starts with cholesterol and via various intermediate compounds eventually affords hydrocortisone (see FIG. 1). Eight proteins are directly involved in this pathway, five of them being enzymes, among which four cytochrome $P_{450}$ enzymes, and the other three being electron transferring proteins.

The first step is the conversion of cholesterol to 3$\beta$-hydroxy-5-pregnene-20-one (pregnenolone). In this conversion, a mono-oxygenase reaction, three proteins are involved: side-chain cleaving enzyme ($P_{450}$SCC, a heme-Fe-containing protein), adrenodoxin (ADX, a $Fe_2S_2$ containing protein) and adrenodoxin reductase (ADR, a FAD-containing protein).

Besides cholesterol as a substrate, the reaction further requires molecular oxygen and NADPH. Subsequently, pregnenolone is converted by dehydrogenation/isomerization to $\Delta^4$-pregnene-3,20-dione (progesterone). This reaction, catalyzed by the protein 3$\beta$-hydroxy steroid dehydrogenase/isomerase (3$\beta$-HSD), requires pregnenolone and NAD+.

To obtain hydrocortisone, progesterone subsequently is hydroxlated at three positions which conversions are catalyzed by mono-oxygenases. In the conversions of progesterone into 17$\alpha$-hydroxy progesterone, two proteins are involved:

steroid 17$\alpha$-hydroxylase ($P_{450}$17$\alpha$, a heme-Fe-containing protein) and NADPH cytochrome $P_{450}$ reductase (RED, a FAD- and FMN-containing protein). The reaction consumes progesterone, molecular oxygen and NADPH.

For the conversion of 17$\alpha$-hydroxyprogesterone into 17$\alpha$, 21-dihydroxy-$\Delta^4$-pregnene-3,20-dione (cortexolone), also two proteins are needed: steroid-21-hydroxylase ($P_{450}$C21, a heme-Fe-containing protein) and the before-mentioned protein RED. The reaction consumes 17$\alpha$-hydroxy progesterone, molecular oxygen and NADPH.

In the conversion of cortexolone into hydrocortisone, three proteins are involved: steroid 11$\beta$-hydroxylase ($P_{450}$11$\beta$, a heme-Fe-containing protein), and the above mentioned proteins ADX and ADR.

As described above, cytochrome $P_{450}$ proteins are enzymes which are essential for the biochemical conversion of cholesterol to hydrocortisone. These enzymes belong to a larger group of cytochrome $P_{450}$ proteins (or shortly $P_{450}$ proteins). They have been encountered in prokaryotes (various bacteria) and eukaryotes (yeasts, molds, plants and animals). In mammals, high levels of $P_{450}$ proteins are found in the adrenal cortex, ovary, testes and liver.

Many of these proteins have been purified and are well characterized now. Their specific activity has been determined. Recently, a number of reviews on this subject have been published such as K. Ruckpaul and H. Rein (eds), "Cytochrome $P_{450}$" and P. R. Oritz de Montellano (ed.) "Cytochrome $P_{450}$, structure, mechanism and biochemistry". Cytochrome $P_{450}$ proteins are characterized by their specific absorbance maximum at 450 nm after reduction with carbon monoxide. In prokaryotic organisms, the $P_{450}$ proteins are either membrane bound or cytoplasmatic. As far as the bacterial $P_{450}$ proteins have been studied in detail (e.g. $P_{450}$meg and $P_{450}$cam), it has been shown that a ferredoxin and a ferredoxin reductase are involved in the hydroxylating activity. For eukaryotic organisms, two types of $P_{450}$ proteins, I and II have been described. Their two differences reside in:

1. subcellular localization, type I is localized in the microsomal fraction and type II is localized in the inner membrane of mitochondria;
2. the way the electrons are transferred to the $P_{450}$ protein. Type I is reduced by NADPH via a $P_{450}$ reductase, whereas Type II is reduced by NADPH via a ferredoxin-reductase (e.g. adrenodoxin reductase) and a ferredoxin (e.g. adrenodoxin).

According to EP-A-0,281,245, cytochrome $P_{450}$ enzymes can be prepared from Streptomyces species and used for the hydroxylation of chemical compounds. The enzymes are used in isolated form, which is a rather tedious and expensive procedure.

JP-A-62,236,485 (Derwent 87-331,234) teaches that it is possible to introduce into *Saccharomyces cerevisiae* the genes of liver cytochrome $P_{450}$ enzymes and to express them affording enzymes which may be used for their oxidation activity. However, in the above references, there is no indication of the use of cytochrome $P_{450}$ enzymes for the preparation of steroid compounds.

OBJECTS OF THE INVENTION

It is an object of the invention to provide an improved biochemical pathway for the production of hydrocortisone and expression cassettes useful therein.

It is another object of the invention to provide recombinant host cells and their progeny containing said expression cassettes.

These and other objects and advantages of the invention will become obvious from the following detailed description.

THE INVENTION

The process of the invention for the preparation of hydrocortisone from sterols comprises culturing a recombinant cell in a nutrient medium, the recombinant host containing an expression cassette, operable in a recombinant host, comprising a heterologous DNA coding sequence encoding a protein, which is functional, alone or in cooperation with one or more additional proteins, of catalyzing an oxidation step in the biological pathway for conversion of cholesterol into hydrocortisone, which step is selected from the group consisting of:

the conversion of cholesterol to pregnenolone;
the conversion of pregnenolone to progesterone;
the conversion of progesterone to 17α-hydroxyprogesterone;
the conversion of 17α-hydroxyprogesterone to cortexolone;
the conversion of cortexolone to hydrocortisone, and the corresponding control sequences effective in said host.

The invention provides a multiplicity of expression cassettes for production of proteins necessary in the construction of a multigenic system for the one-step conversion of inexpensive steroid starting materials to more rare and expensive end products, wherein such conversion is carried out in native systems through a multiplicity of enzyme-catalyzed and cofactor-mediated conversions, such as the production of hydrocortisone from cholesterol. The expression cassettes of the invention are useful in the ultimate production of multigenic systems for conducting these multi-step conversions.

Accordingly, in one aspect, the invention is directed to an expression cassette effective in a recombinant host cell in expressing a heterologous coding DNA sequence, wherein said coding sequence encodes an enzyme which is able, alone or in cooperation with additional proteins, to catalyze an oxidation step in the biological pathway for the conversion of cholesterol to hydrocortisone. The expression cassettes of the invention, therefore, include those sequences capable of producing, in a recombinant host, the following proteins: side-chain cleaving enzyme ($P_{450}SCC$); adrenodoxin (ADX); adrenodoxin reductase (ADR); 3β-hydroxy steroid dehydrogenase/isomerase (3β-HSD); steroid 17α-hydroxylase ($P_{450}17\alpha$); NADPH cytochrome $P_{450}$ reductase (RED); steroid-21-hydroxylase ($P_{450}C21$); and steroid 11β-hydroxylase ($P_{450}11\beta$).

In other aspects, the invention is directed to recombinant host cells transformed with these vectors or with the expression cassettes of the invention, to methods to produce the above enzymes and to use these enzymes for oxidation, to processes to use said host cells for specific oxidations in a culture broth and to pharmaceutical compositions containing compounds prepared by said processes.

BRIEF DESCRIPTION OF THE FIGURES

Abbreviations used in all figures: $R_I$, EcoRI; H, HindIII; Sc, ScaI; P, PstI; K, KpnI; St, StuI; Sp, SphI; X, XbaI; N, NdeI; S, SmaI; Ss, SstI; $V_v$, EcoRV; $S_I$, SacI; B, BamHI; $S_{II}$, SacII; Sal, SalI; Xh, XhoI; Pv, PvuII; Bg, BglII and M, MluI.

FIG. 5 shows the complete nucleotide sequence of plasmid pBHA-1 (SEQ ID NO: 3).

FIG. 11 shows the $P_{450}$SCC expression of pGBSCC-17 in E.coli JM101.

Figure 1:
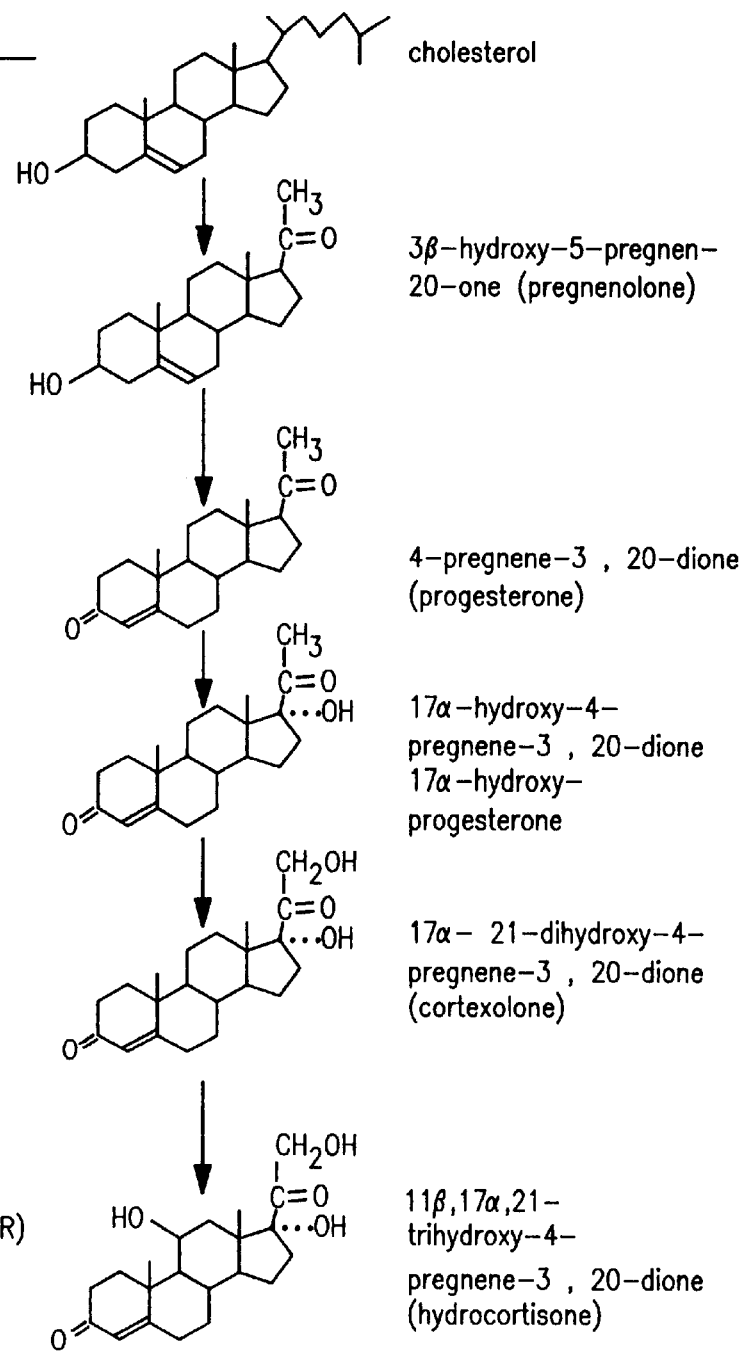
FIG. 1 shows a schematic overview of the proteins involved in the succeeding steps in the conversion of cholesterol in hydrocortisone as occurring in the adrenal cortex of mammals.

(a) SDS/PAGE and Coomassie brilliant blue staining of the cellular protein fractions (20 μl) prepared from the E.coli control strain (lane 3) and E.coli transformants SCC-301 and 302 (lanes 1 and 2, resp.). 400 ng purified bovine $P_{450}$SCC (lane 4) is shown for comparison.

(b) Western-blot analysis probed with antibodies against $P_{450}$SCC of cellular protein fractions (5 μl) prepared from the control strain E.coli JM101 (lane 2) and from the E.coli JM101 (lane 3) and SCC-302 (lane 4). 100 ng purified bovine $P_{450}$SCC (lane 1) is shown for comparison.

Figure 12:
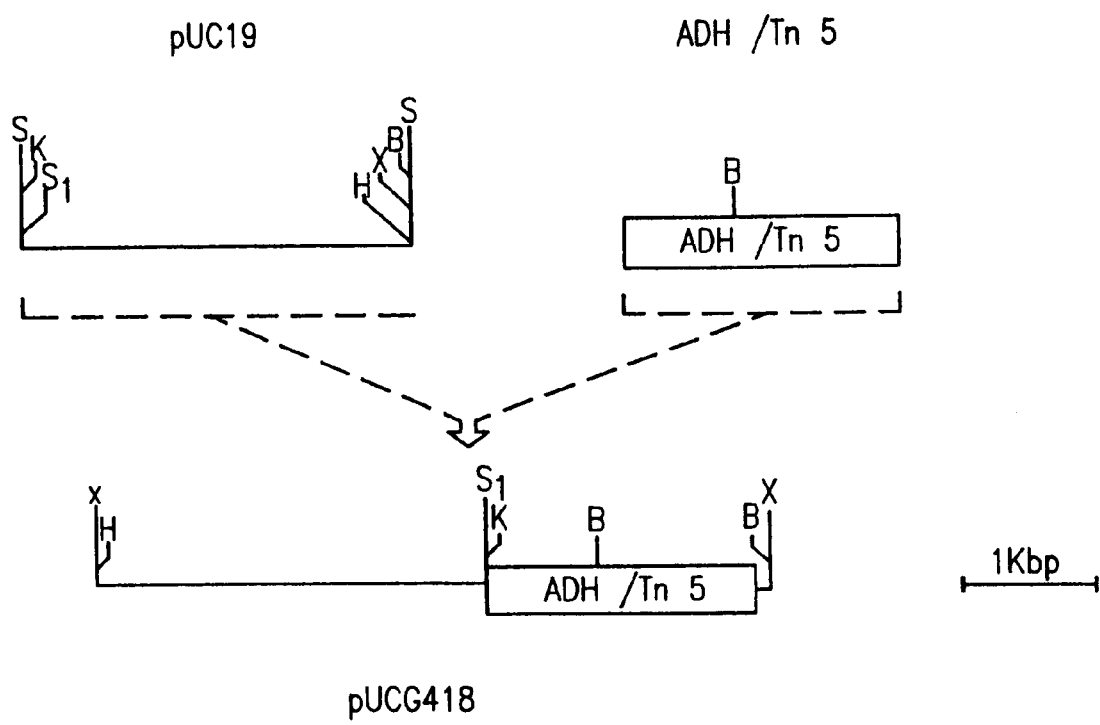

FIG. 12 shows the construction of plasmid pUCG418.

Figure 13:
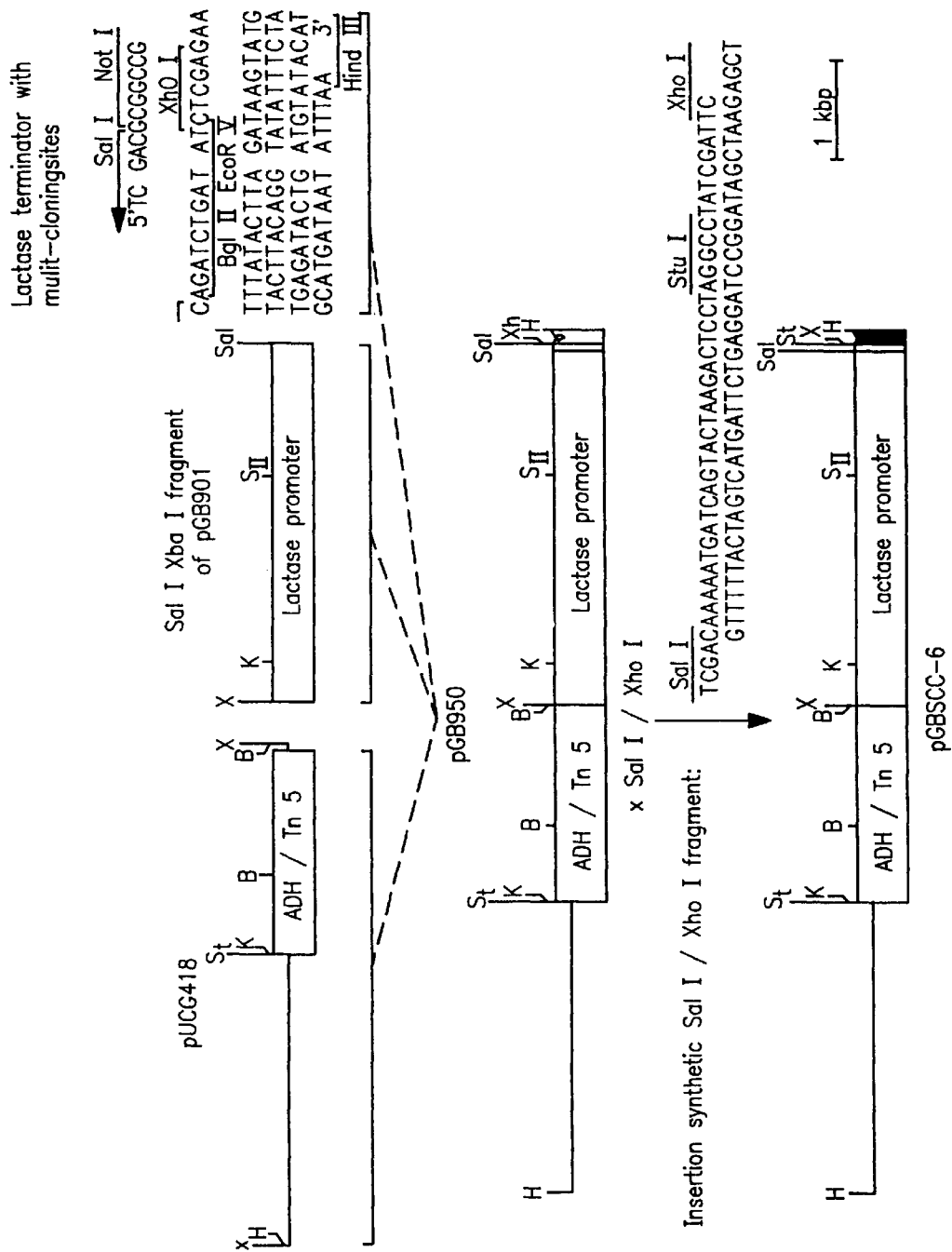

FIG. 13 shows the construction of the yeast expression vector PGB950 by insertion of the promoter and terminator with multiple cloning sites (SEQ ID NO: 8) (▨) of lactase in pUCG418. To derive pGBSCC-6, a synthetic SalI/XhoI fragment (SEQ ID NO: 9) containing an ATG start codon and the codons for the first 8 amino acids of $P_{450}$SCC is inserted in pGB950.

Figure 14:
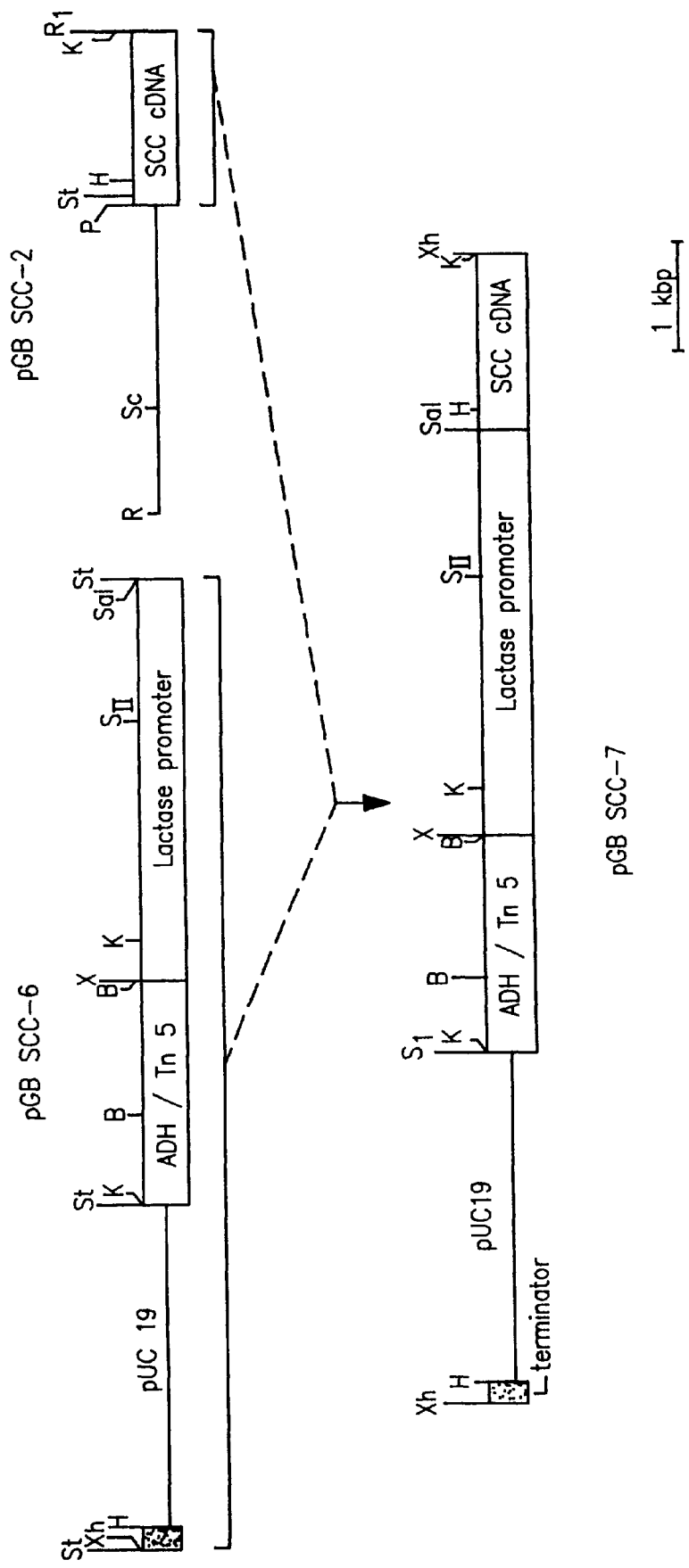

FIG. 14 is a schematic presentation showing the construction of the yeast $P_{450}$SCC-expression cassette pGBSCC-7.

FIG. 15 shows a Western-blot probed with antibodies specific for the protein $P_{450}$SCC.
Blot A contains extracts derived from Saccharomyces cerevisiae 273-10B transformed with pGBSCC-10 (lane 1); from S.cerevisiae 273-10B as a control (lane 2); from Kluyveromyces lactis CBS 2360 transformed with pGBSCC-7 (lane 3) and from K.lactis CBS 2360 as a control (lane 4).
Blot B contains extracts derived from K.lactis CBS 2360 as a control (lane 1) and K.lactis CBS 2360 transformed with pGBSCC-15 (lane 2), with pGBSCC-12 (lane 3) or with pGBSCC-7 (lane 4).
Blot C contains extracts derived from S.cerevisiae 273-10B as a control (lane 1) transformed with pGBSCC-16 (lane 2) or with pGBSCC-13 (lane 3).

Figure 16:
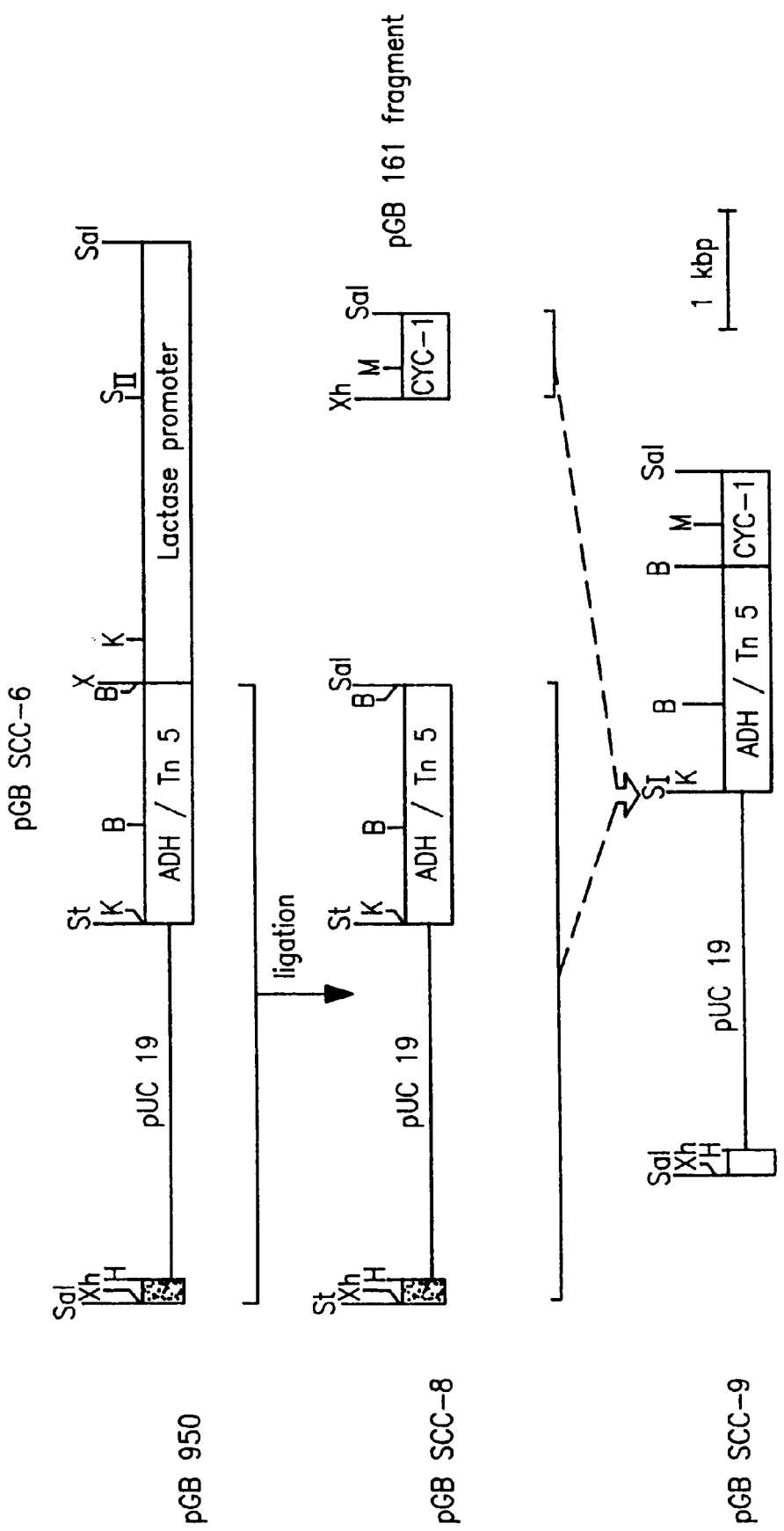

FIG. 16 is a schematic presentation of the construction of the yeast expression vector pGBSCC-9 containing the isocytochrome CI (cyc-1) promoter from S.cerevisiae.

Figure 17:
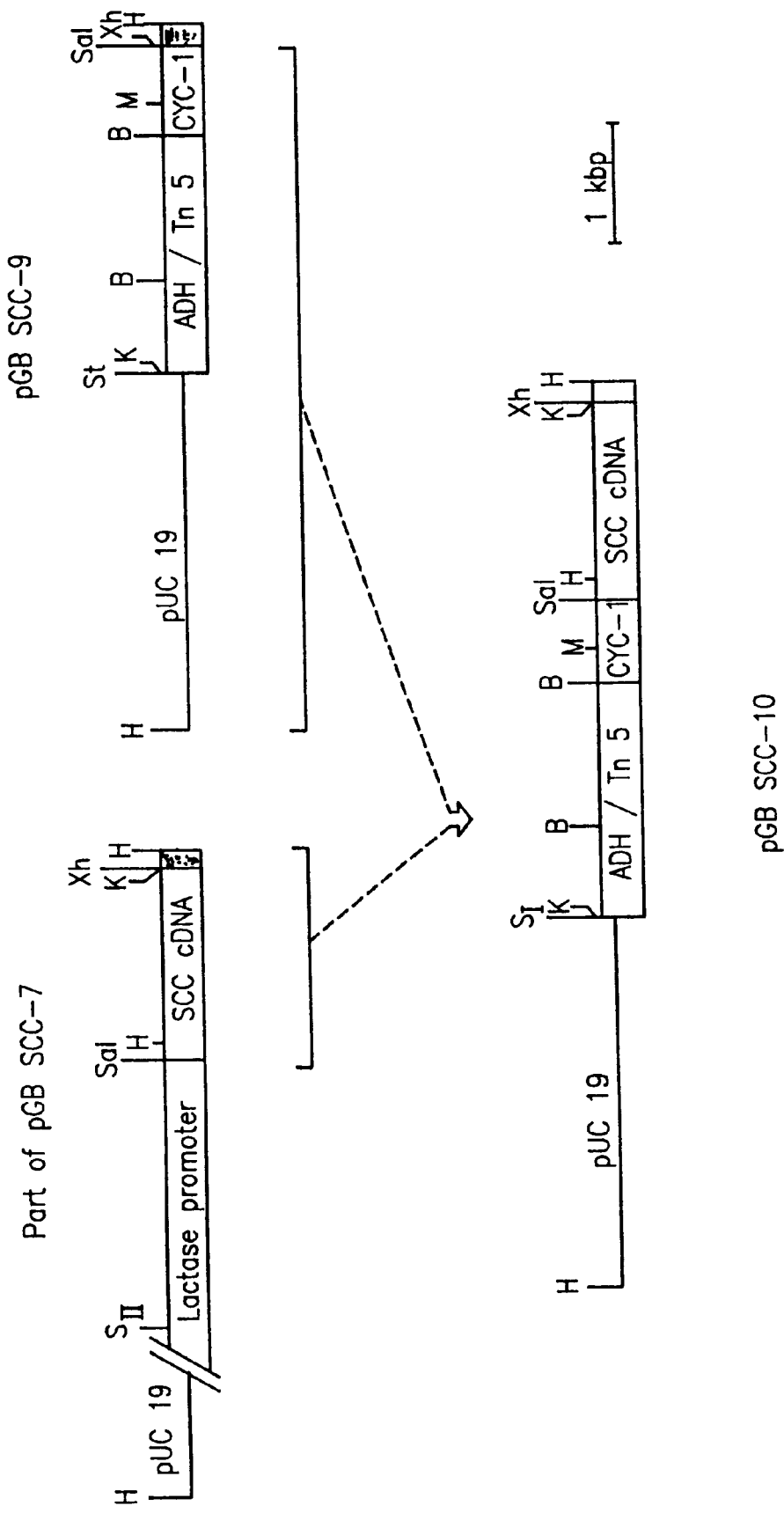

FIG. 17 shows a construction diagram of the $P_{450}$SCC cDNA containing expression vector pGBSCC-10 for S.cerevisiae.

Figure 18:
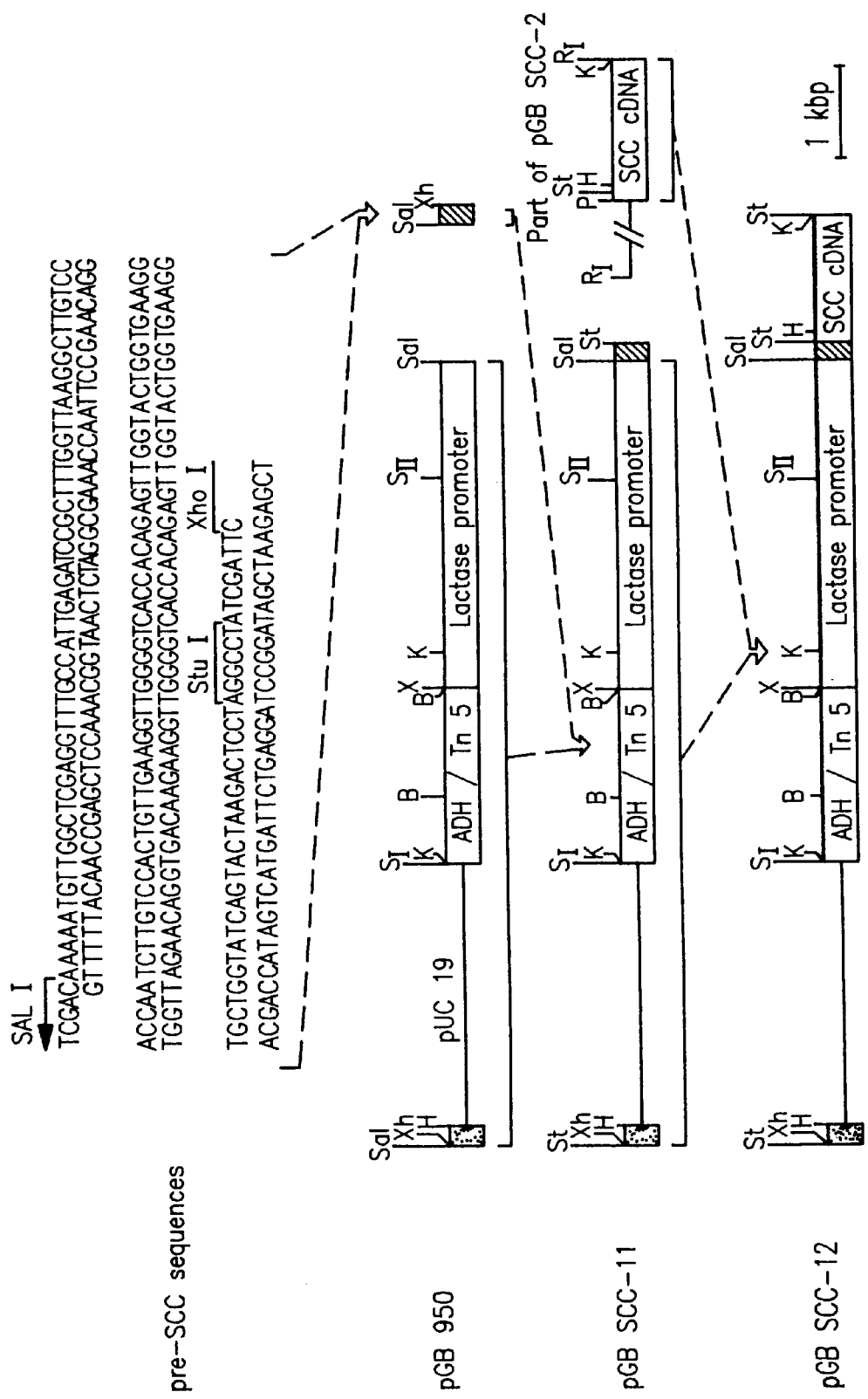

FIG. 18 shows the construction of the $P_{450}$SCC expression vector pGBSCC-12 in which a synthetically derived DNA-fragment encoding the pre-$P_{450}$SCC sequence (▨) is inserted 5' for the coding sequence of mature $P_{450}$SCC.

Figure 19:
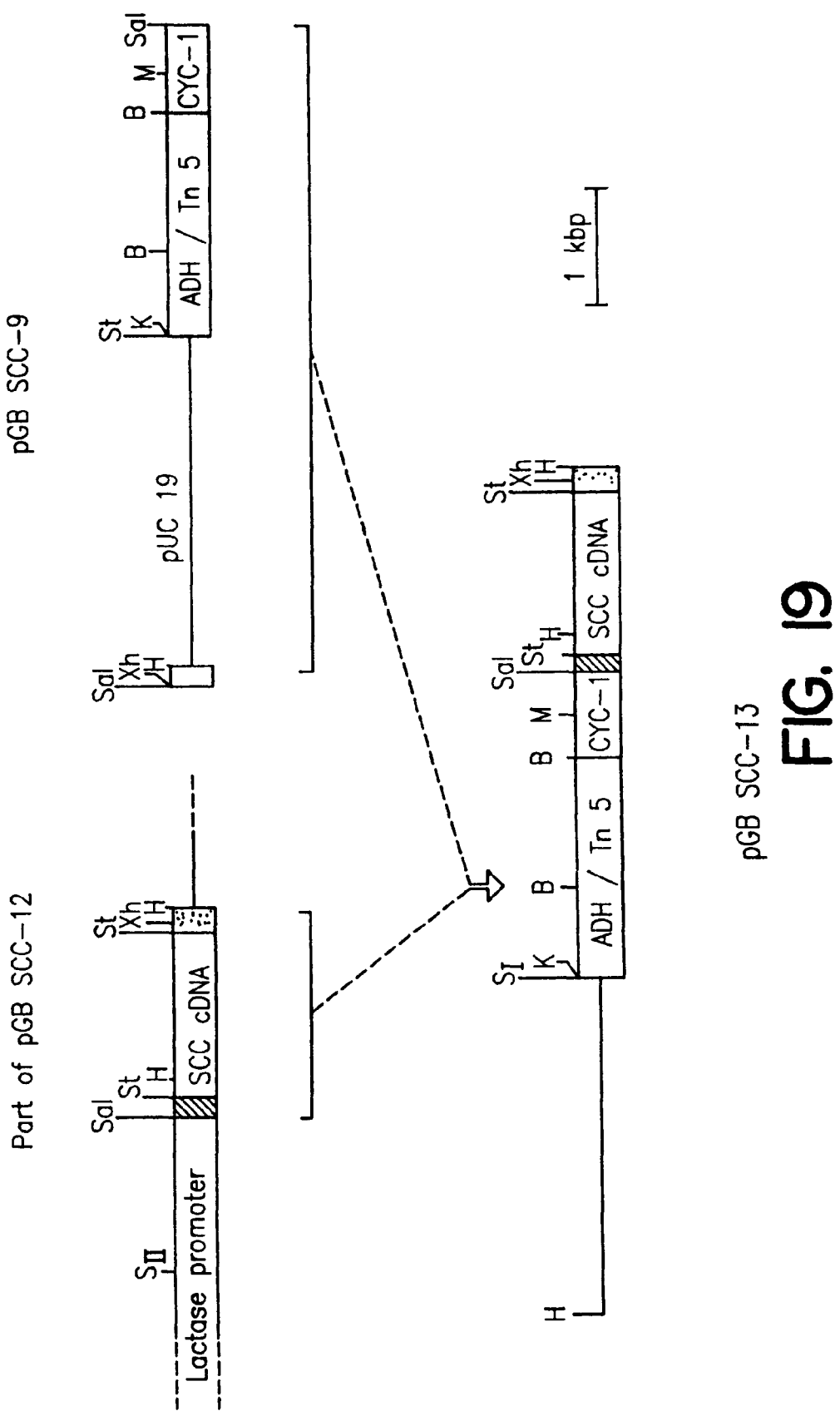

FIG. 19 shows the construction of the pGBSCC-13. This $p_{450}$SCC expression cassette for S.cerevisiae contains the pre-$P_{450}$SCC cDNA sequence positioned 3' of the cyc-1 promoter of S.cerevisiae.

Figure 20:
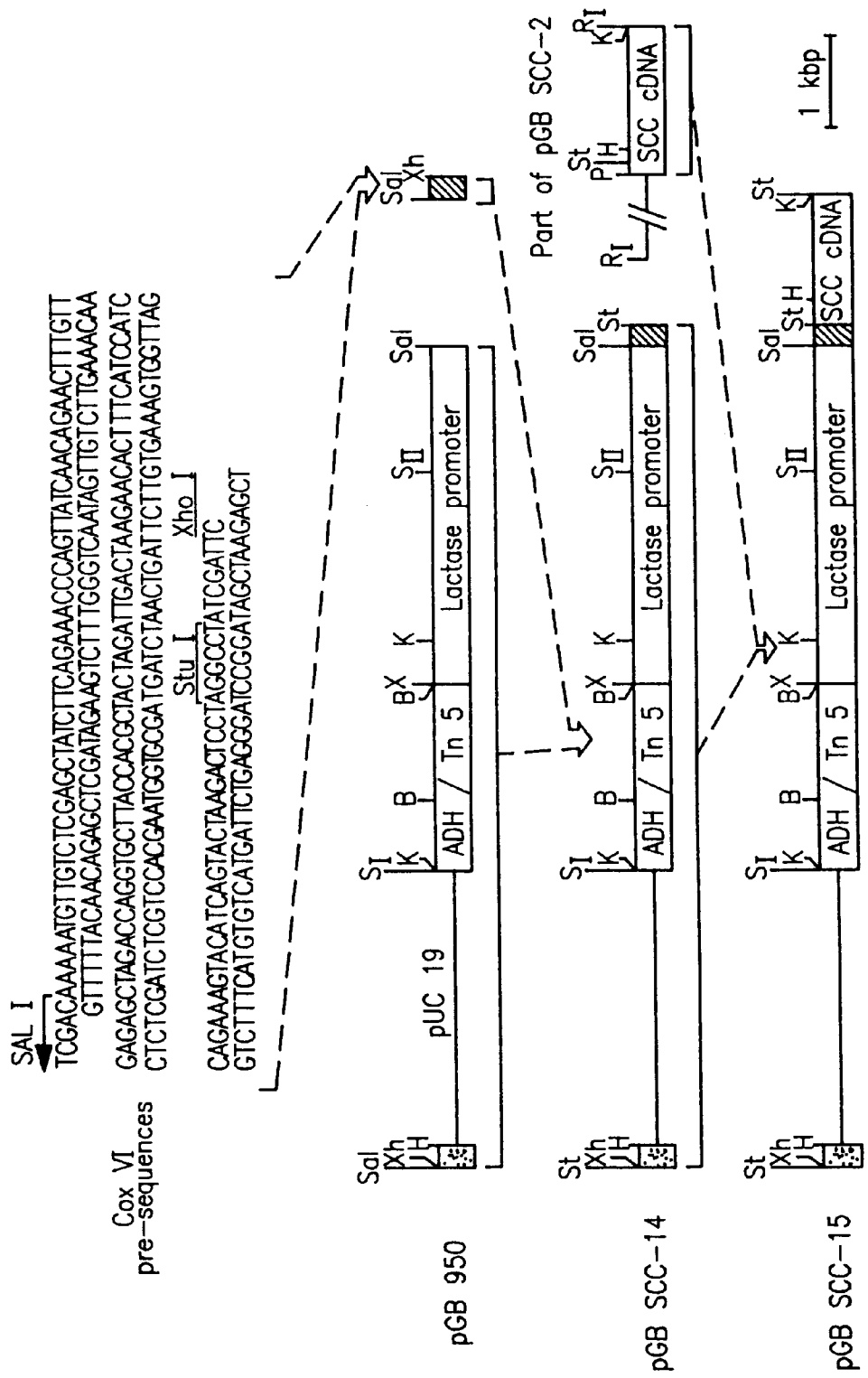

FIG. 20 shows a schematic representation of the construction of the plasmids pGBSCC-14 and pGBSCC-15. The latter contains the $P_{450}$SCC coding sequence in frame with the cytochrome oxidase VI pre-sequence (▨).

Figure 21:
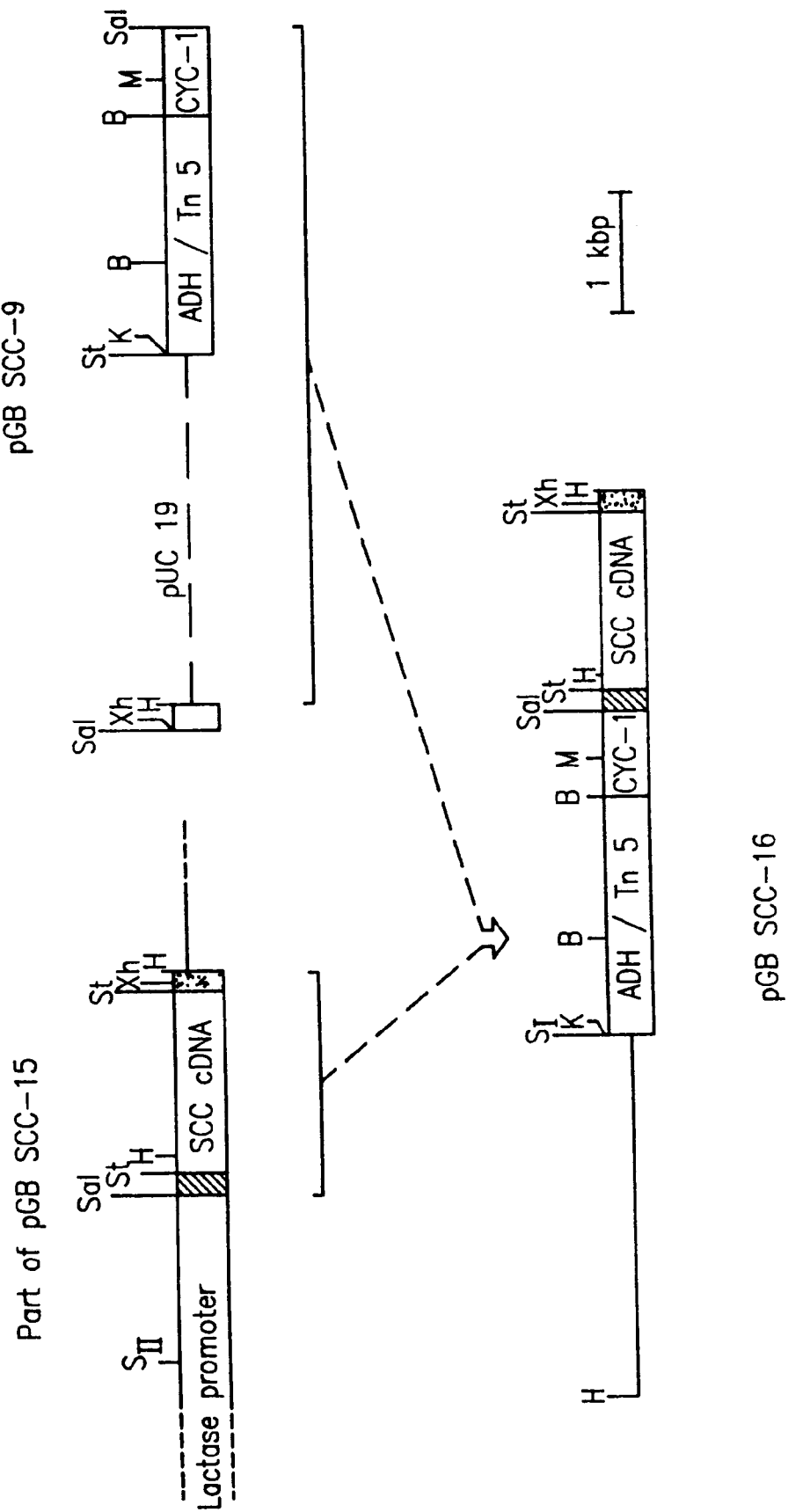

FIG. 21 shows the construction of the plasmid pGBSCC-16. In this plasmid, the cytochrome oxidase VI presequence (▨) of S.cerevisiae fused to the coding $P_{450}$SCC sequence is positioned 3' of the cyc-1 promoter.

Figure 22A:
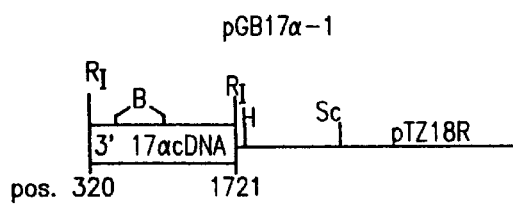
Figure 22B:
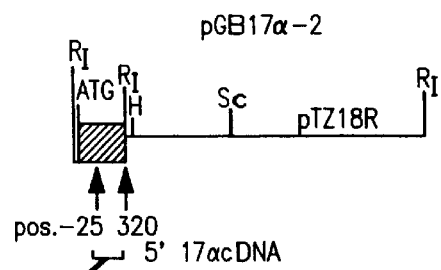
Figure 22C:
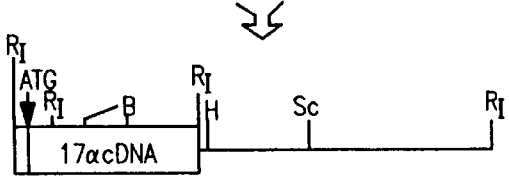

FIGS. 22A, 22B and 22C show the physical maps of the plasmids pGB17α-1 (A) and pGB17α-2 (B) containing the 3' 1.4 kb fragment and the 5' 345 bp fragment (▨) of $P_{450}17α$ cDNA, resp. In pGB17α-3 (C) containing the full length $P_{450}17α$ cDNA sequence, the position of the ATG start codon is indicated.

Figure 23A:
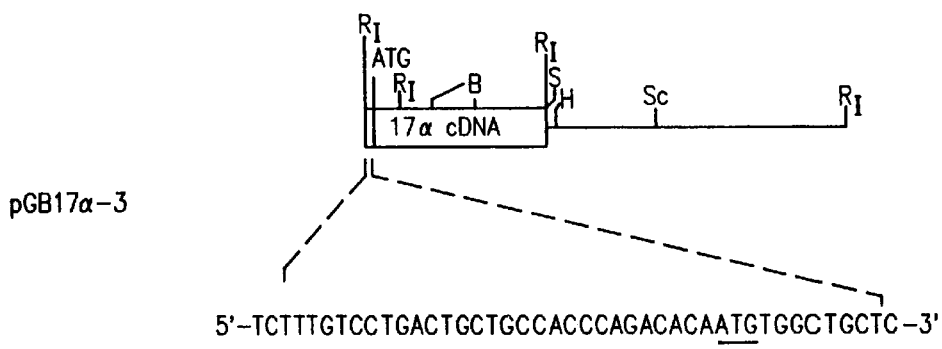
Figure 23B:
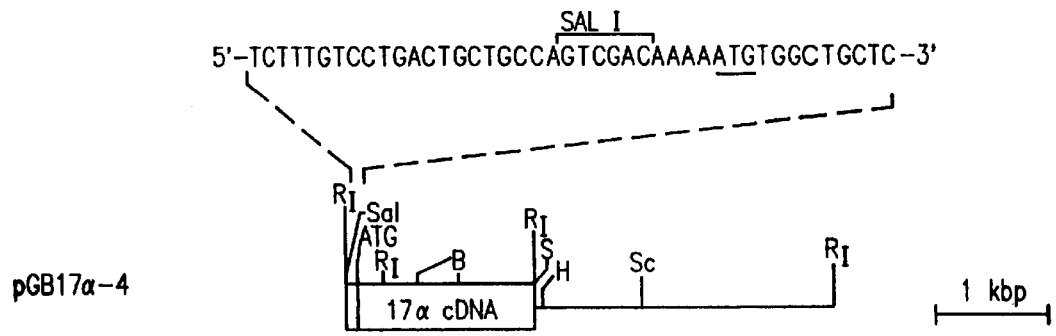

FIGS. 23A and 23B show the mutation of pGB17α-3 by in vitro mutagenesis (SEQ ID NO: 17). The obtained plasmid pGB17α-4 contains a SalI restriction site (SEQ ID NO: 18) followed by optimal yeast translation signals just upstream the ATG initiation codon.

Figure 24:
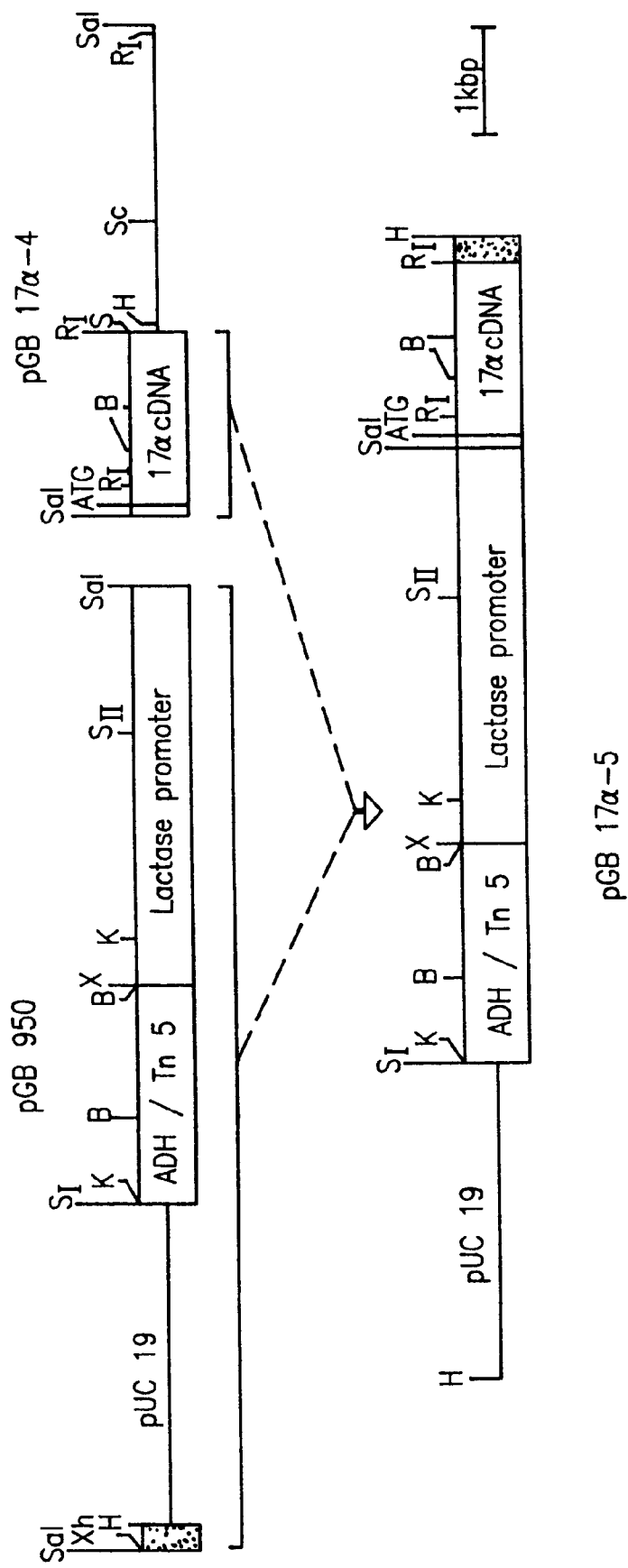

FIG. 24 is a schematic view of the construction of the yeast $P_{450}17α$ expression cassette pGB17α-5.

Figure 25:
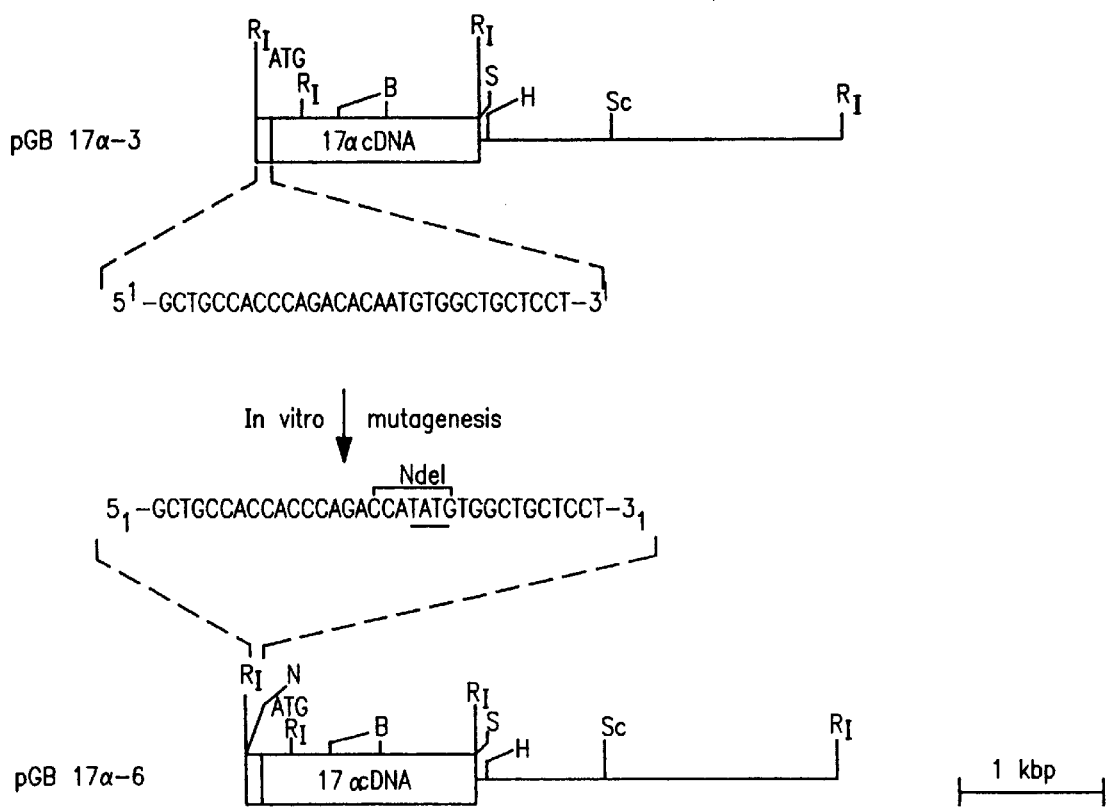

FIG. 25 shows the mutation of pGB17α-3 by in vitro mutagenesis (SEQ ID NO: 19). The obtained plasmid pGB17α-6 contains an NdeI restriction site (SEQ ID NO: 20) at the ATG-initiation codon.

Figure 26:
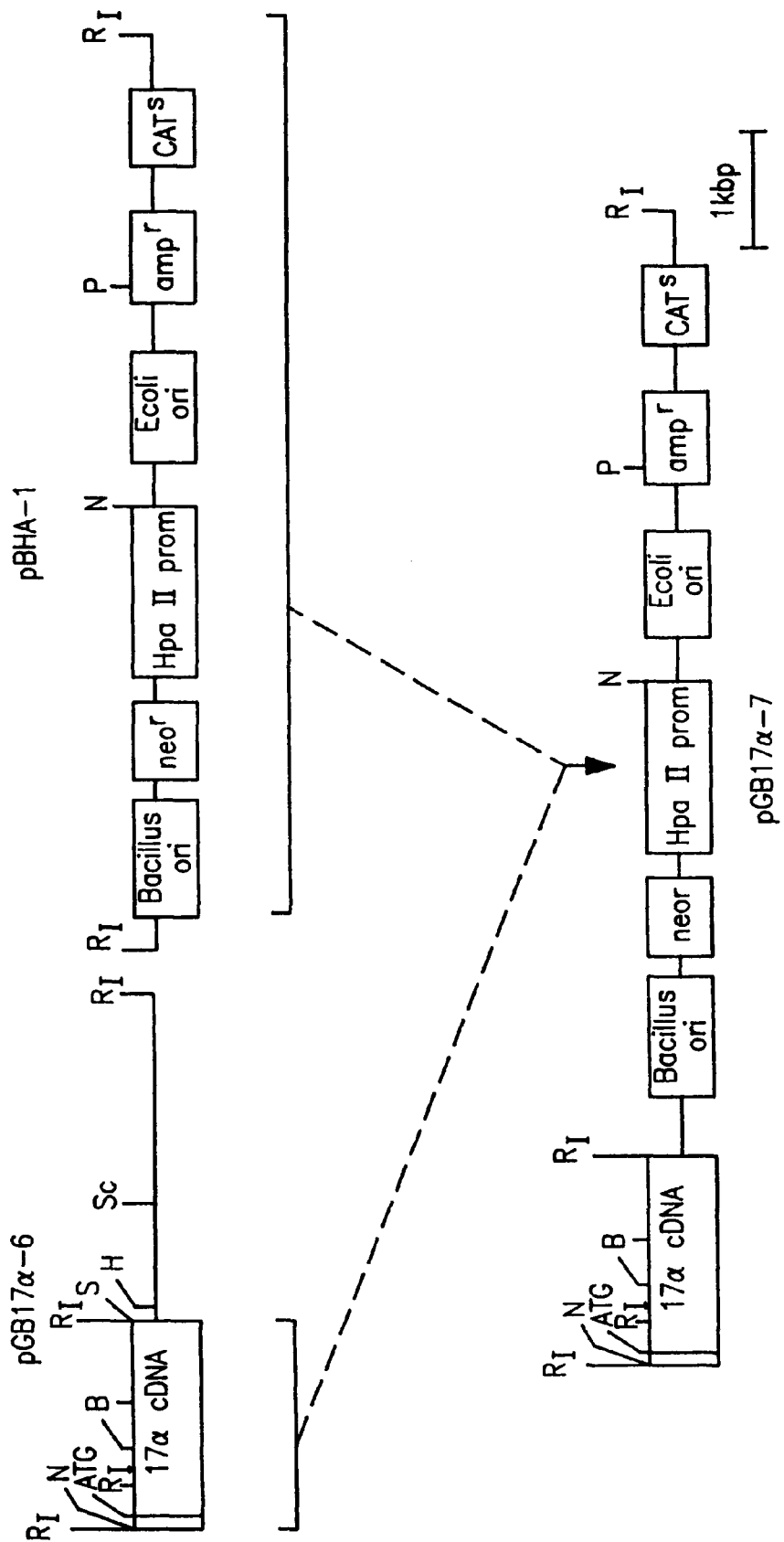

FIG. 26 is a schematic representation of the construction of pGB17α-7. $P_{450}17α$ cDNA sequences from plasmid pGB17α-6 were introduced into the Bacillus/E.coli shuttle plasmid pBHA-1.

FIG. 27 shows a physical map of pGB17α-8 which is obtained by removal of E.coli sequences from the plasmid pGB17α-7.

FIGS. 28A and 28B show physical maps of pGBC21-1 and 2, containing an 1.53 kb 3'-$P_{450}$C21 cDNA and a 540 bp 5'-$P_{450}$ cDNA EcoRI fragment, respectively, in the EcoRI-site of the cloning vector pTZ18R.

Figure 29:
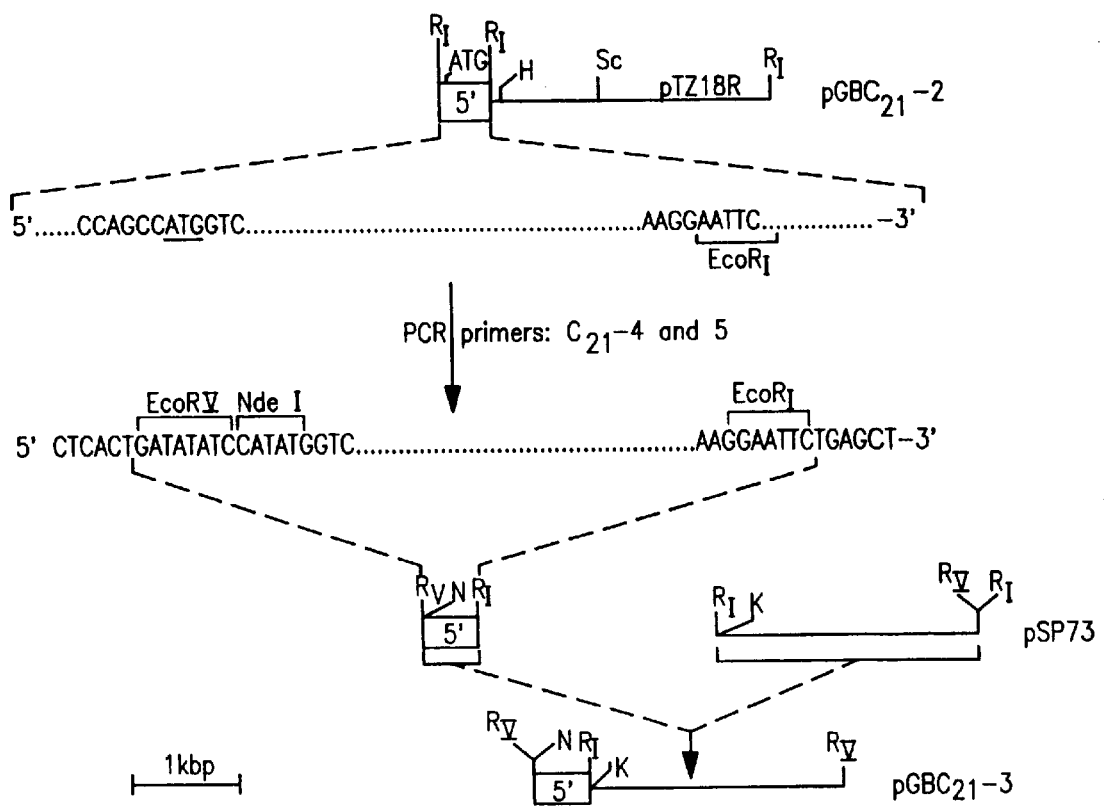

FIG. 29 shows the in vitro mutagenesis by the polymerase chain reaction (PCR) of pGBC21-2 (SEQ ID NOS: 26 and 27) to introduce EcoRV and NdeI restriction sites (SEQ ID NOS: 28 and 29) upstream the $P_{450}$C21 ATG-initiation codon, followed by molecular cloning into the cloning vector pSP$_{73}$ to derive pGBC21-3.

Figure 30:
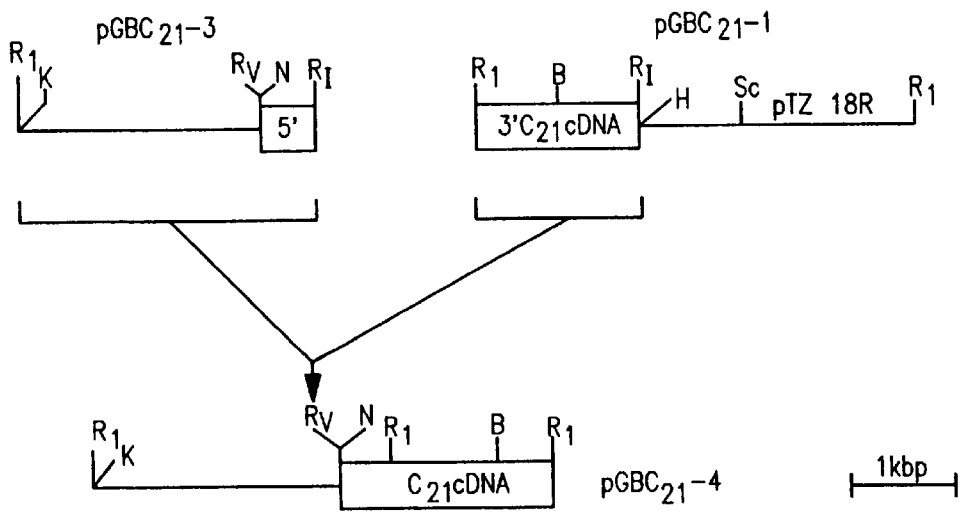

FIG. 30 is a schematic view of the construction of pGBC21-4, containing the full-length $P_{450}$C21 cDNA sequence.

Figure 31:
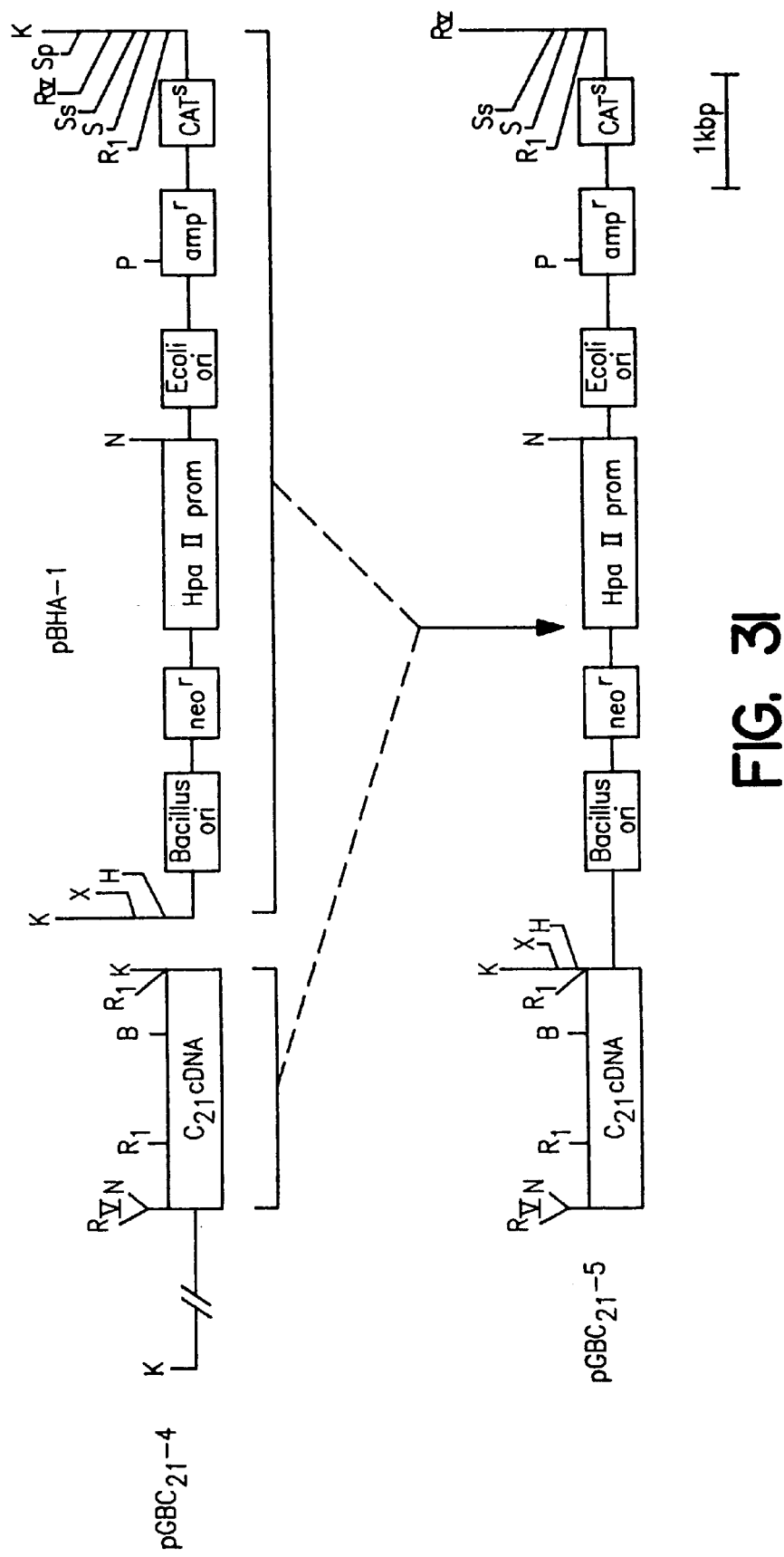

FIG. 31 is a schematic representation of the construction of pGBC21-5. The $P_{450}$C21 cDNA sequence from plasmid pGBC21-4 was introduced into the Bacillus/E.coli shuttle plasmid pBHA-1.

Figure 32A:
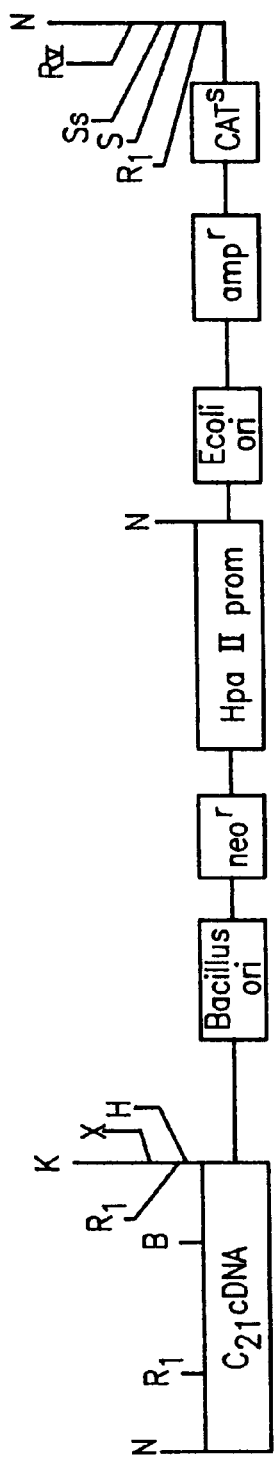
Figure 32B:
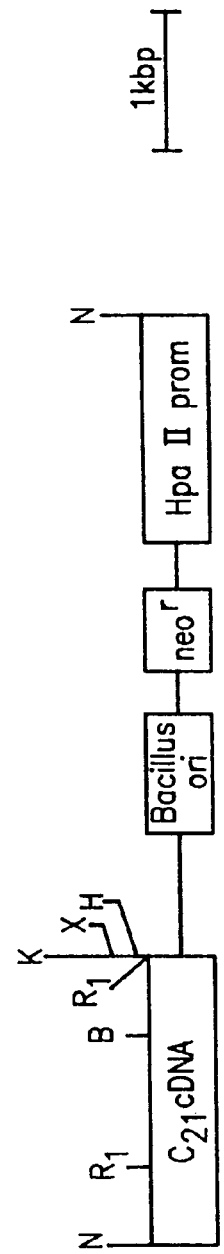

FIG. 32 shows a physical map of pGBC21-6 which is obtained by removal of E.coli sequences from the plasmid pGBC21-5.

Figure 33:
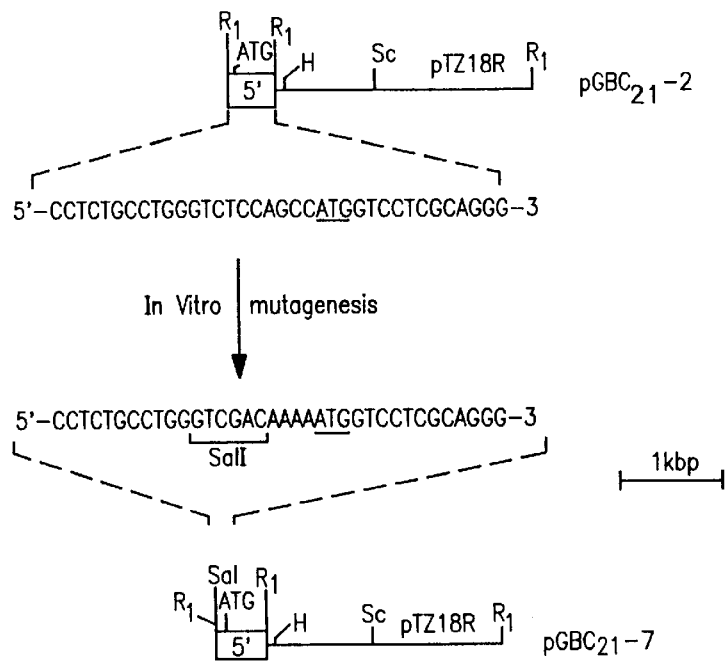

FIG. 33 shows the mutation of pGBC21-2 by in vitro mutagenesis (SEQ ID NO: 31). The obtained plasmid pGBC21-7 contains a SalI restriction site (SEQ ID NO: 30) followed by optimal yeast translation signals just upstream the ATG initiation codon.

Figure 34:
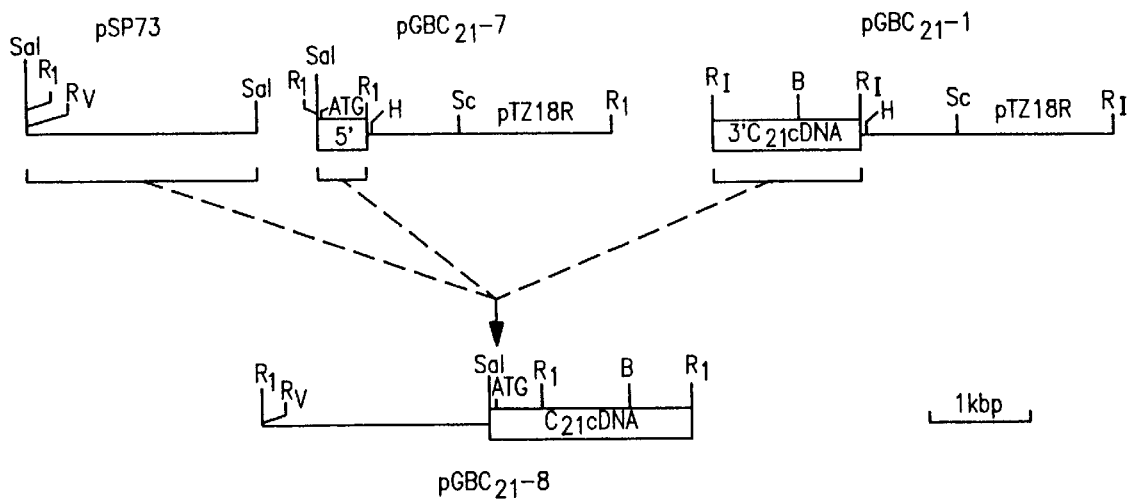

FIG. 34 represents the construction of pGBC21-8, containing a full-length $P_{450}$C21 cDNA with modified flanking restriction sites suitable for cloning into the yeast expression vector.

Figure 35:
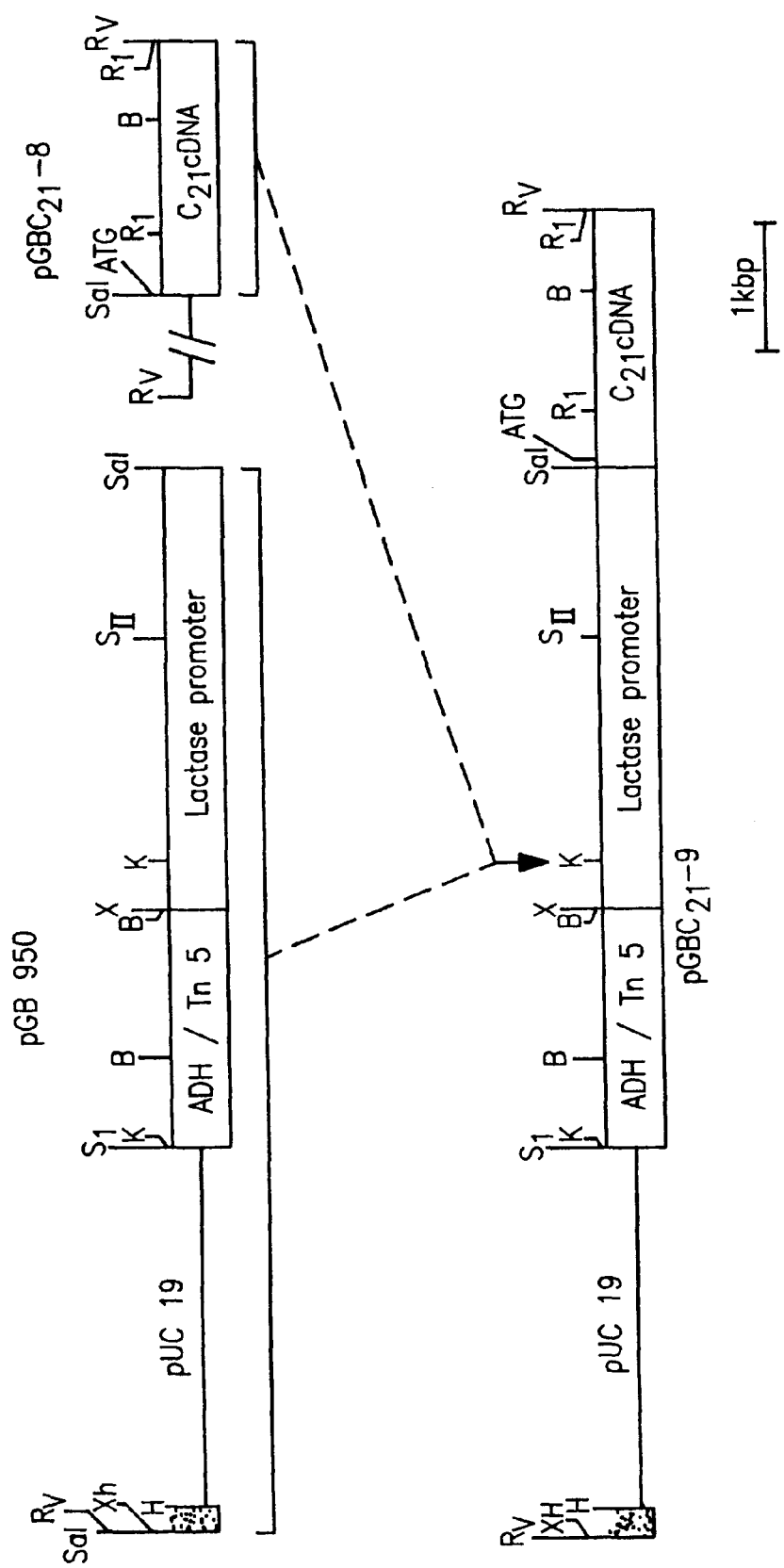

FIG. 35 is a schematic presentation showing the construction of the yeast $P_{450}$C21-expression cassette pGBC21-9.

Figure 36:
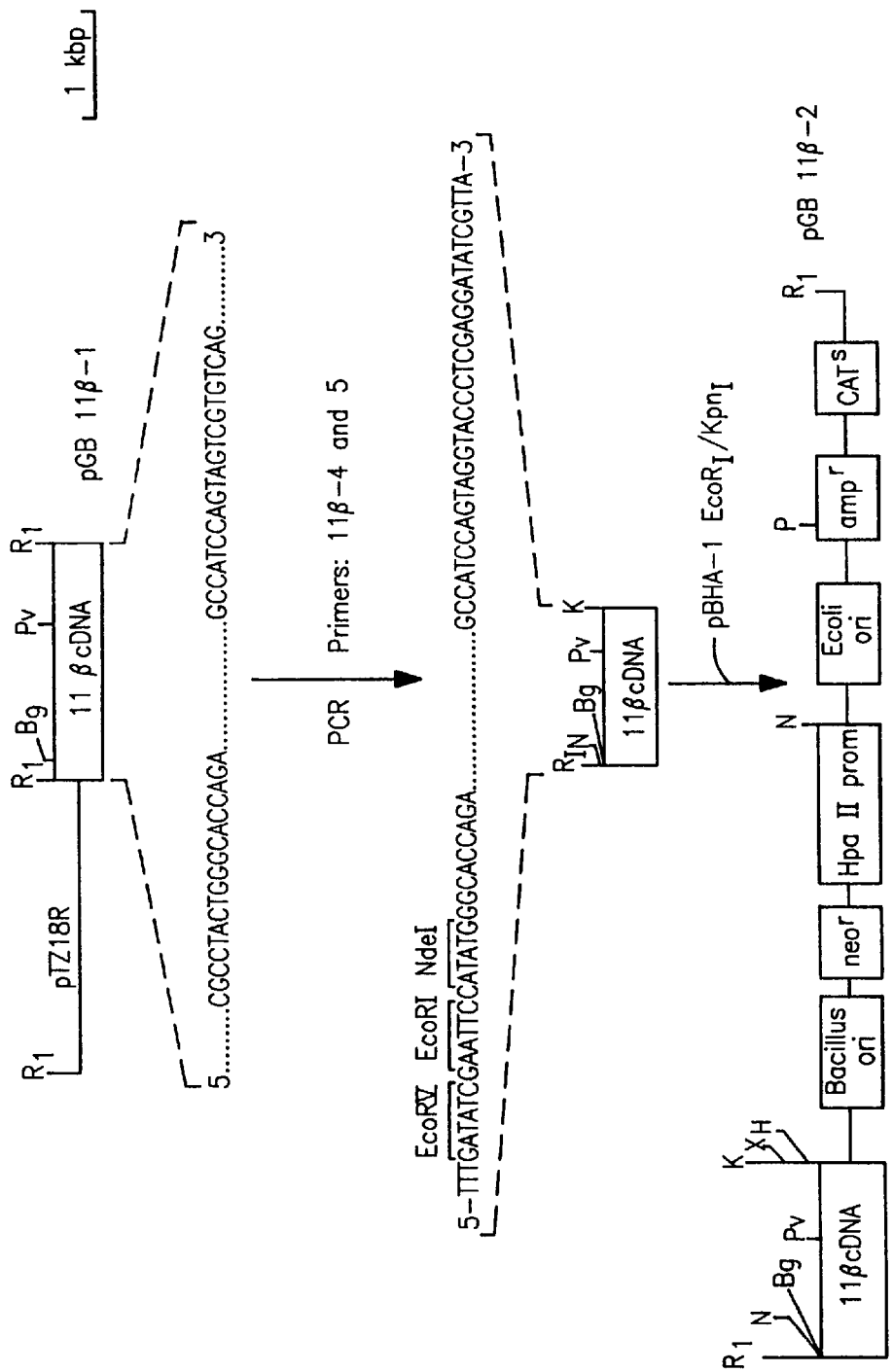

FIG. 36 shows the in vitro mutagenesis by the polymerase chain reaction of pGB11β-1 to introduce appropriate flanking restriction sites and an ATG initiation codon to the full-length $P_{450}11β$ cDNA sequence, followed by molecular cloning into the Bacillus/E.coli shuttle vector pBHA-1 to derive the plasmid pGB11β-2.

Figure 37:
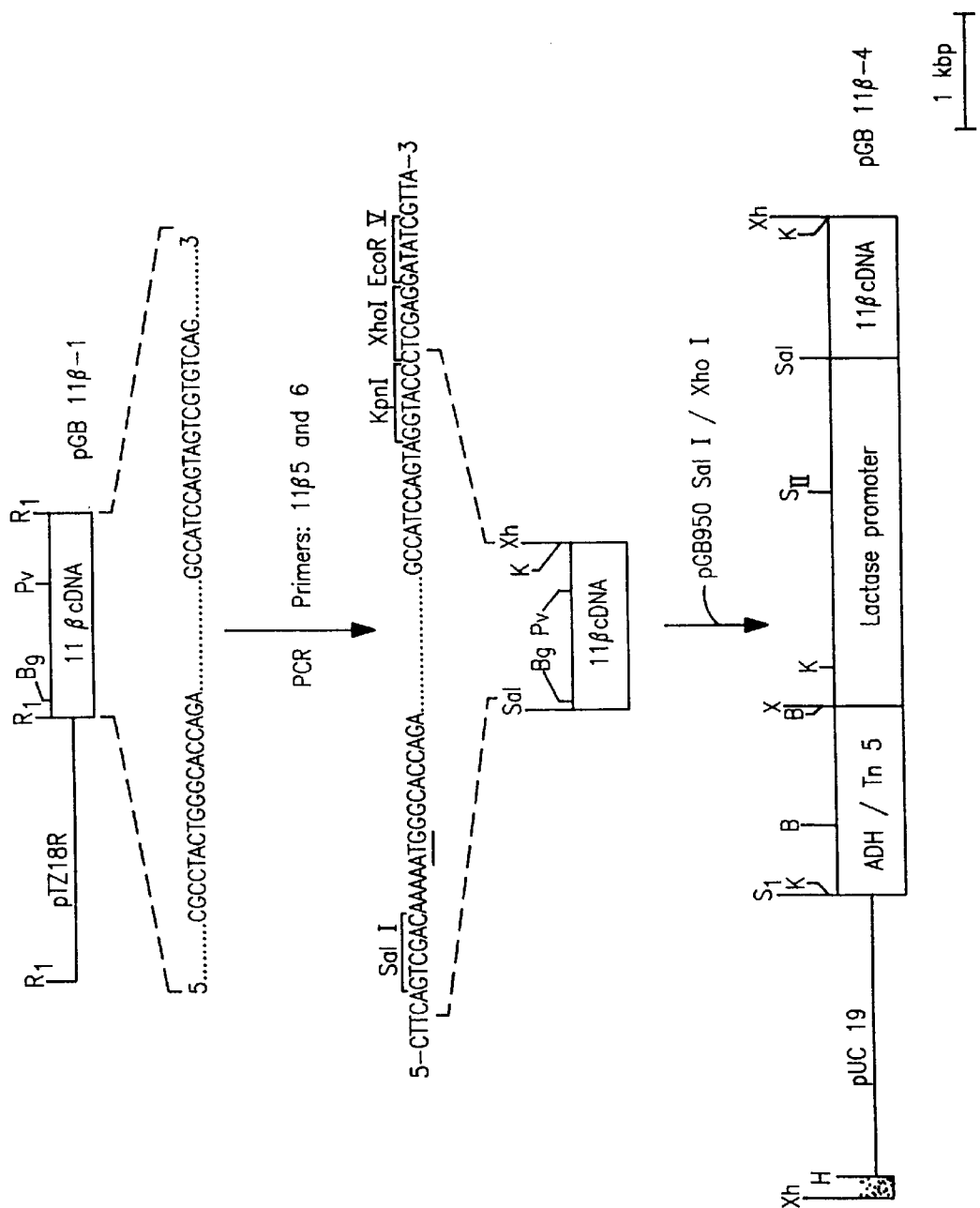

FIG. 37 shows the in vitro mutagenesis by the polymerase chain reaction of pGB11β-1 to introduce appropriate flanking restriction sites and an ATG initiation codon to the full-length $P_{450}11β$ cDNA sequence, followed by molecular cloning into the yeast expression vector pGB950 to derive the plasmid pGB11β-4.

Figure 38:
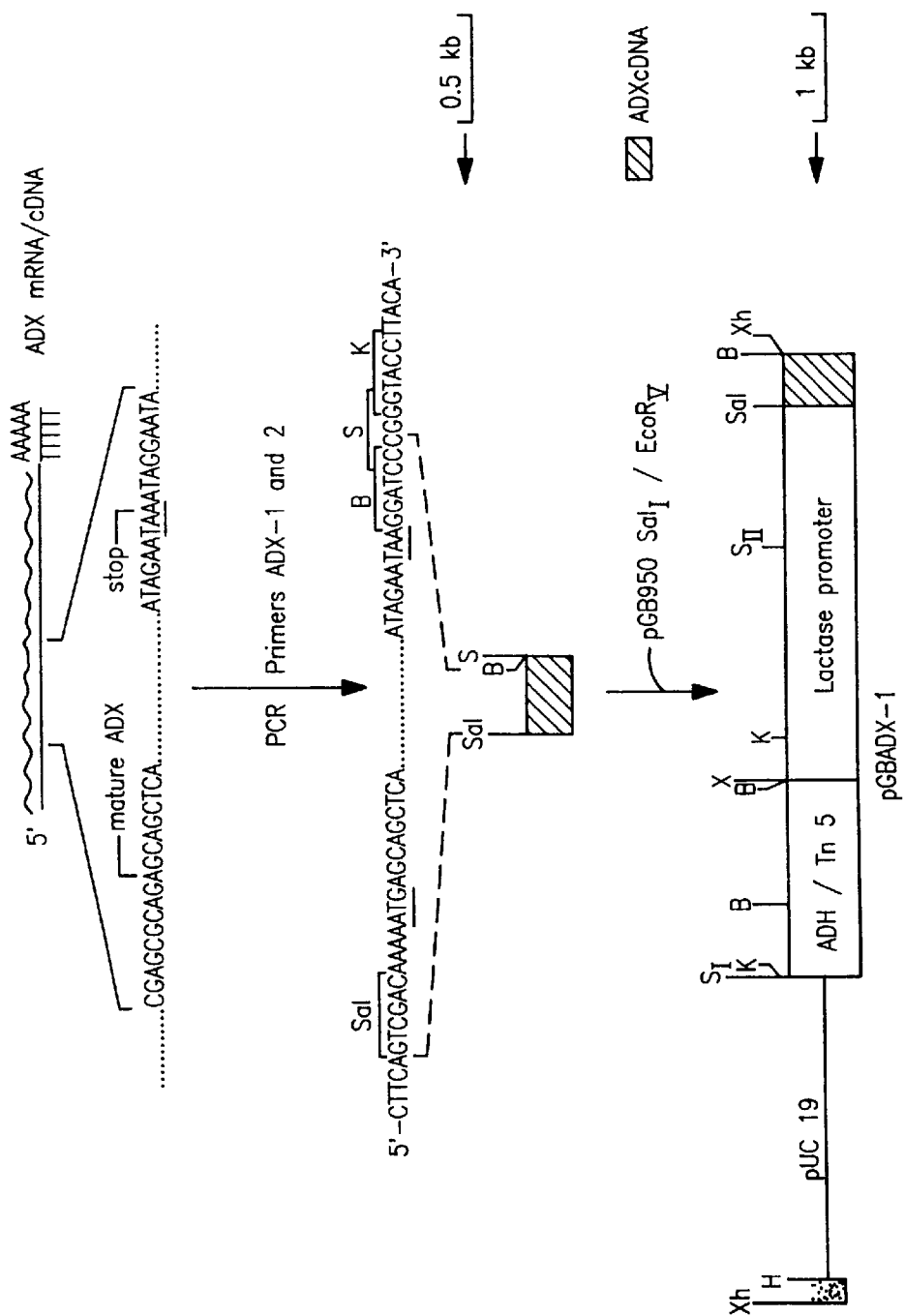

FIG. 38 is a schematic view of the molecular cloning of the ADX cDNA sequence from a bovine adrenal cortex polyA⁺RNA/cDNA mixture by the polymerase chain reaction method. The cDNA sequence encoding the mature ADX protein was inserted into the appropriate sites of the yeast expression vector pGB950 to obtain the plasmid pGBADX-1.

Figure 39:
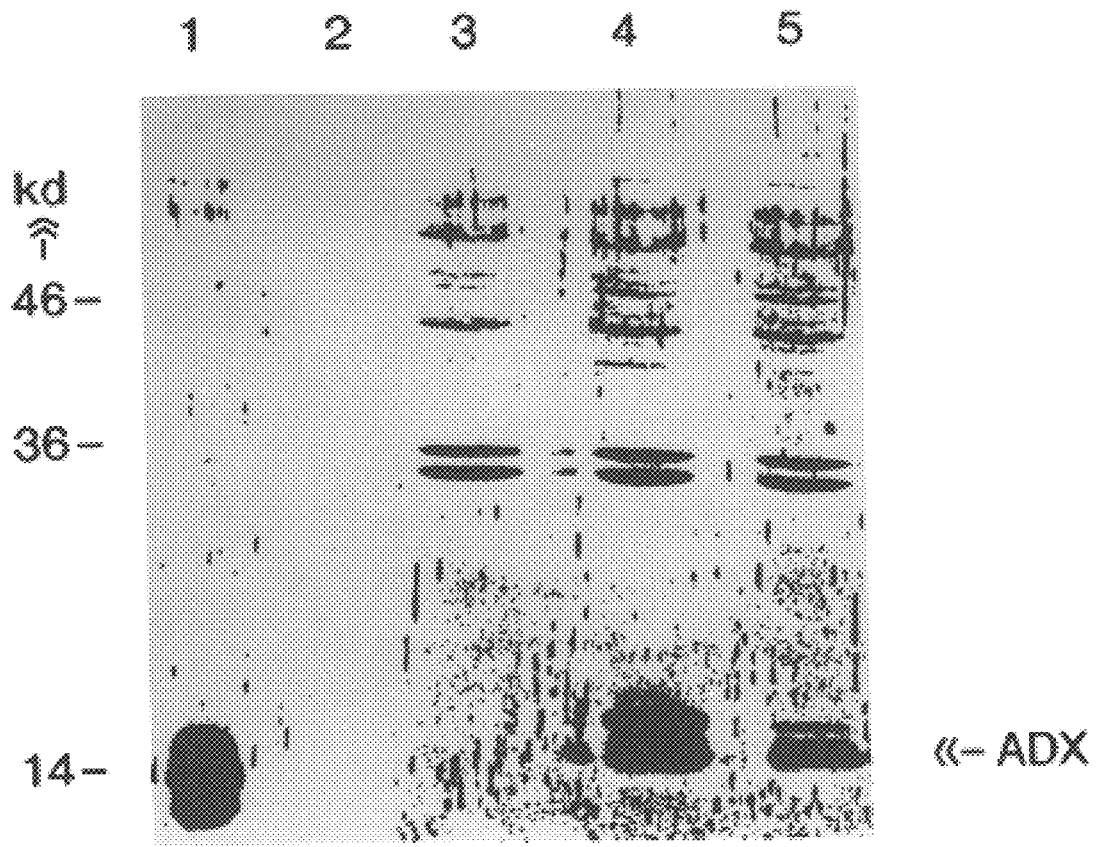

FIG. 39 shows a Western-blot probed with antibodies against ADX, demonstrating the ADX expression of plasmid pGBADX-1 in K.lactis CBS 2360 transformants ADX-101 and 102 (lanes 4 and 5, resp.). Extract of control strain K.lactis CBS 2360 is shown in lane 3. For comparison, also purified adrenal cortex ADX (100 ng) is supplied to the gel in lane 1.

Figure 40:
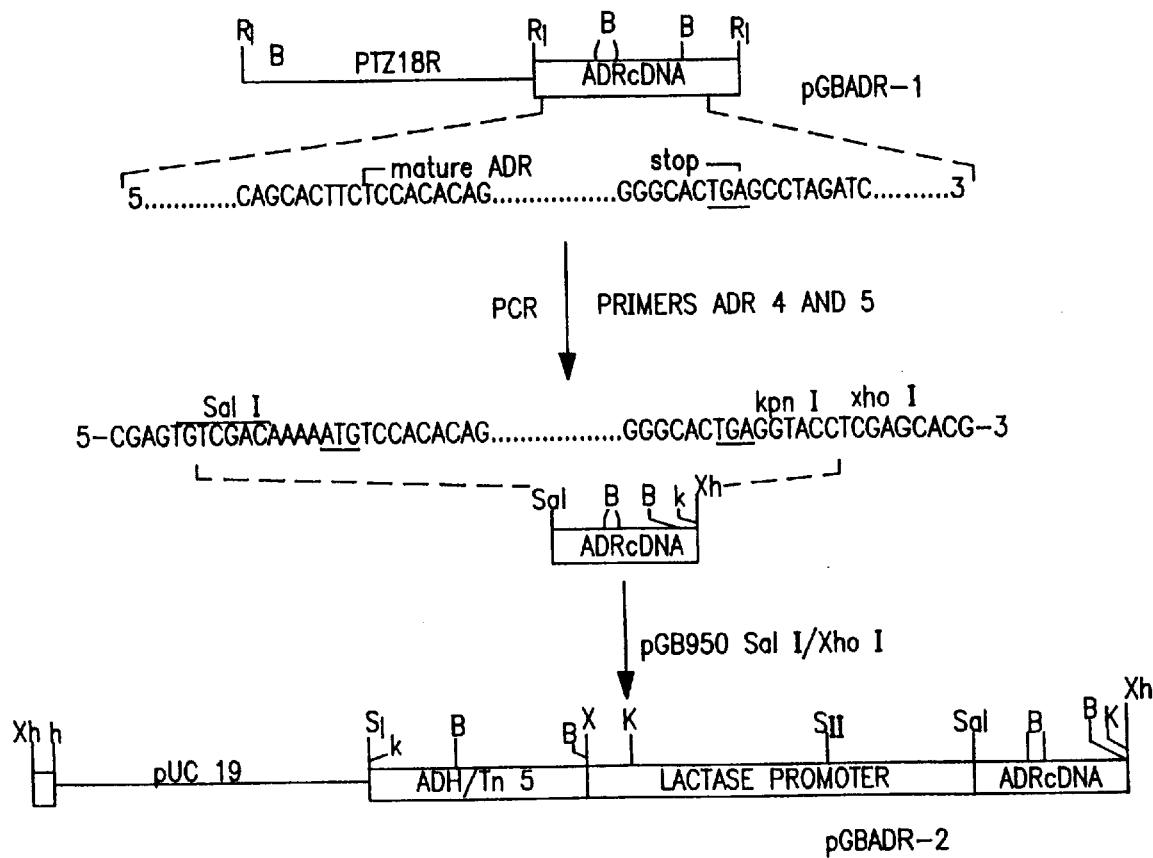

FIG. 40 shows the in vitro mutagenesis by the polymerase chain reaction of pGBADR-1 to introduce appropriate flanking restriction sites and an ATG-initiation codon to the full-length ADR cDNA sequence, followed by molecular cloning into the yeast expression vector pGB950 to derive pGBADR-2.

Figure 41:
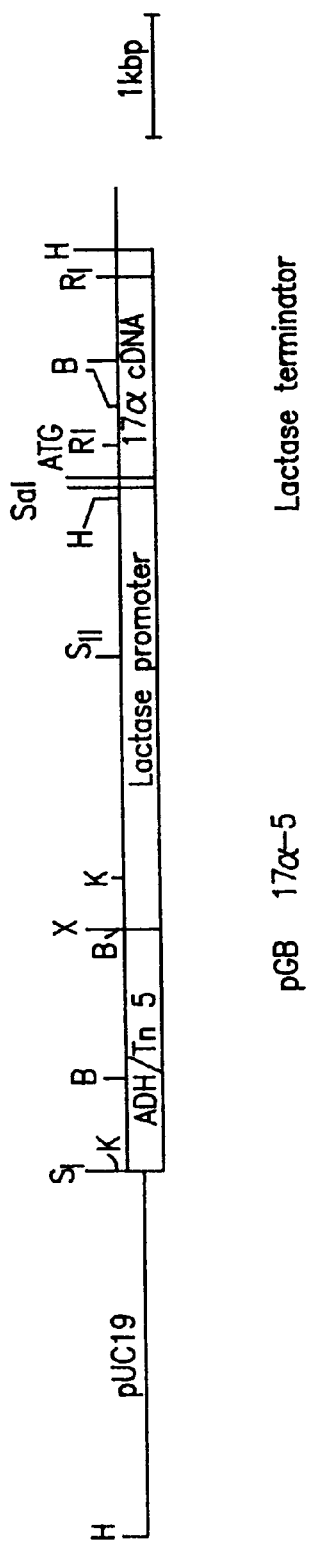

FIG. 41 shows a physical map of the expression cassette pGB17α-5.

Figure 42:
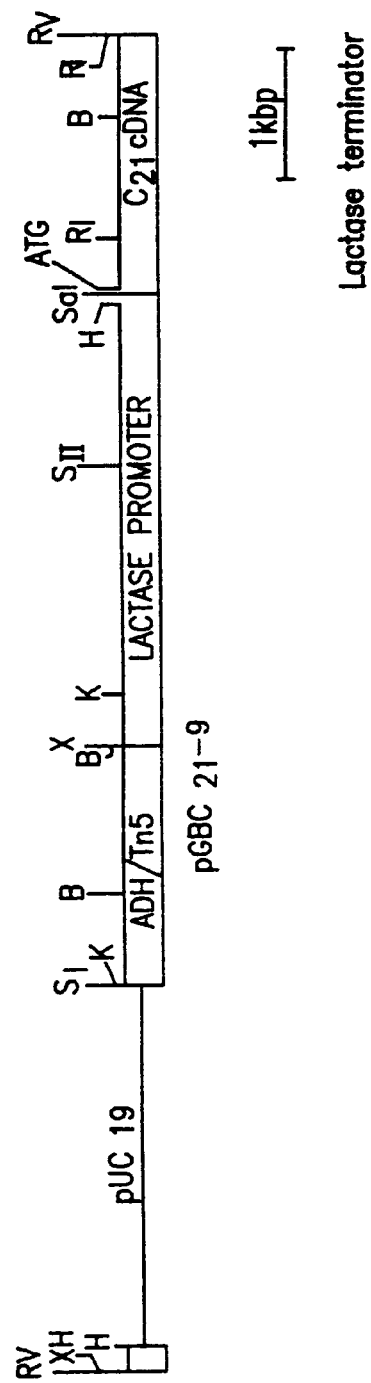

FIG. 42 shows a physical map of the expression cassette pGBC21-9.

Figure 43:
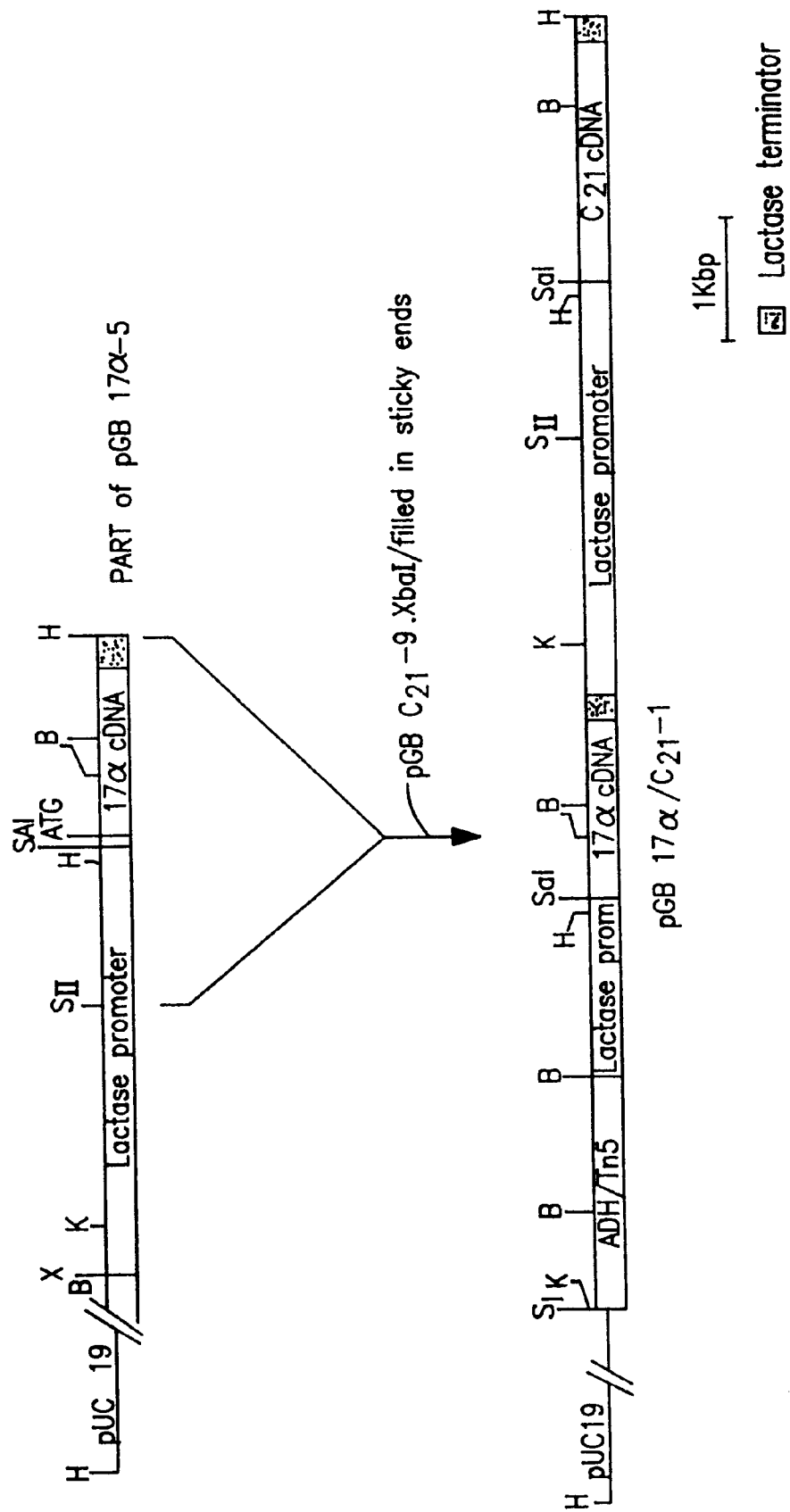

FIG. 43 represents the construction of the expression cassette pGB17α/C21-1, containing the coding sequence for $P_{450}17α$ and $P_{450}$C21, both driven by the lactase promoter.

Figure 44:
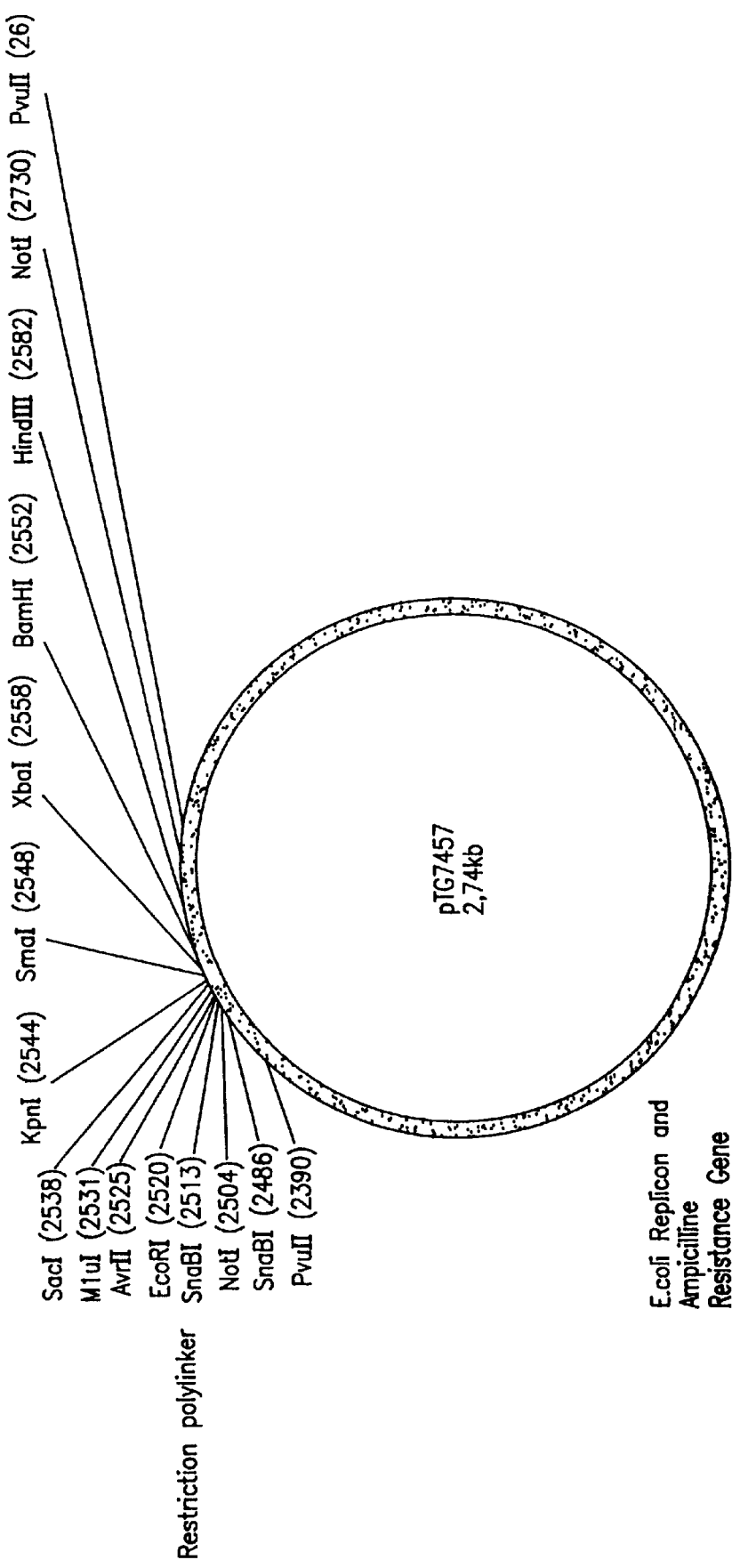

FIG. 44 shows a physical map of the plasmid pTG7457.

Figure 45:
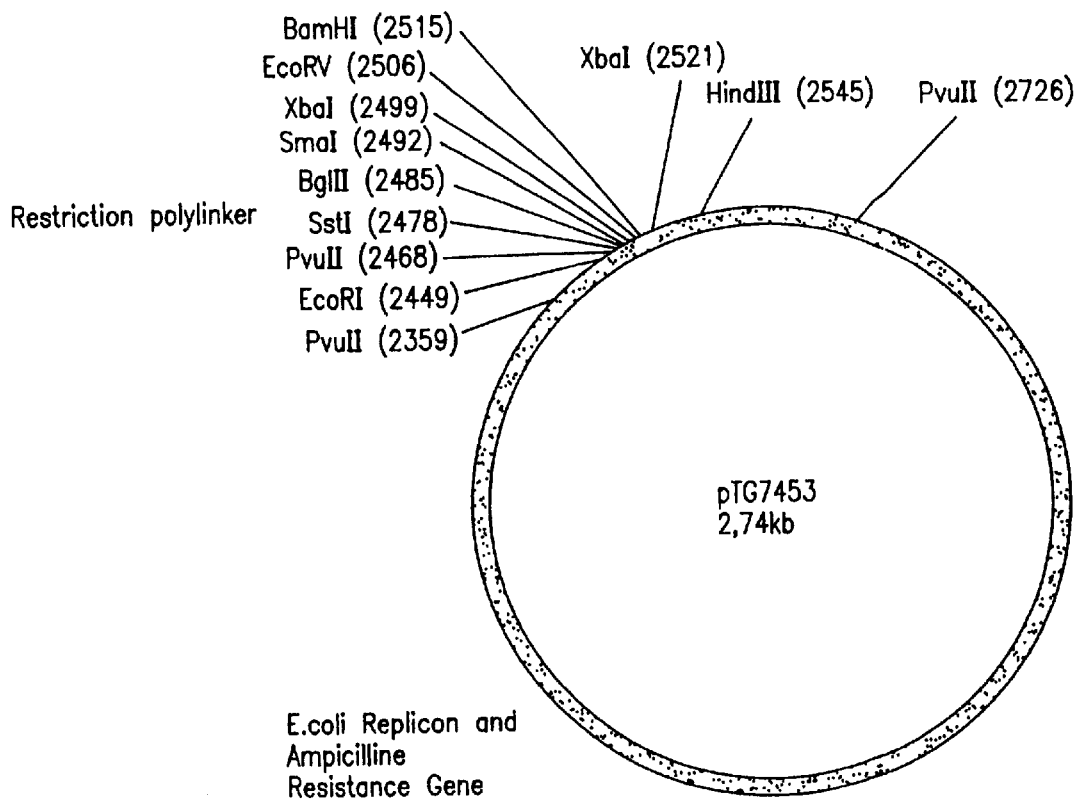
Figure 46:
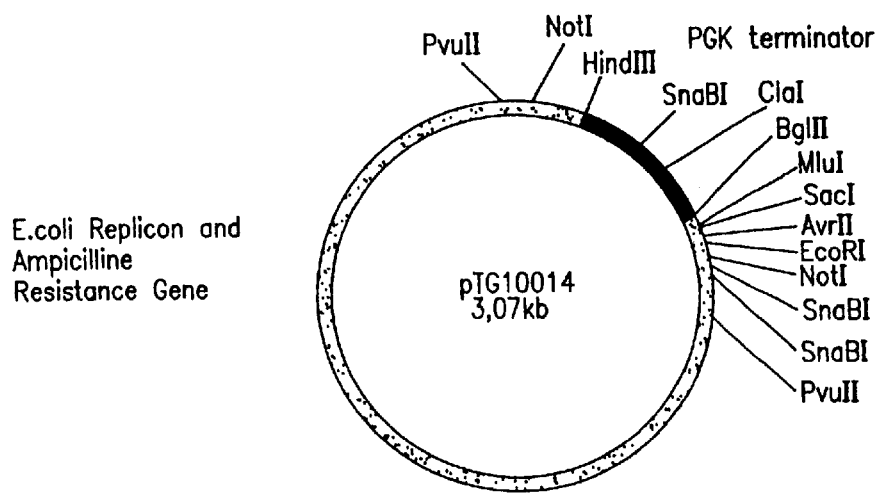
Figure 47:
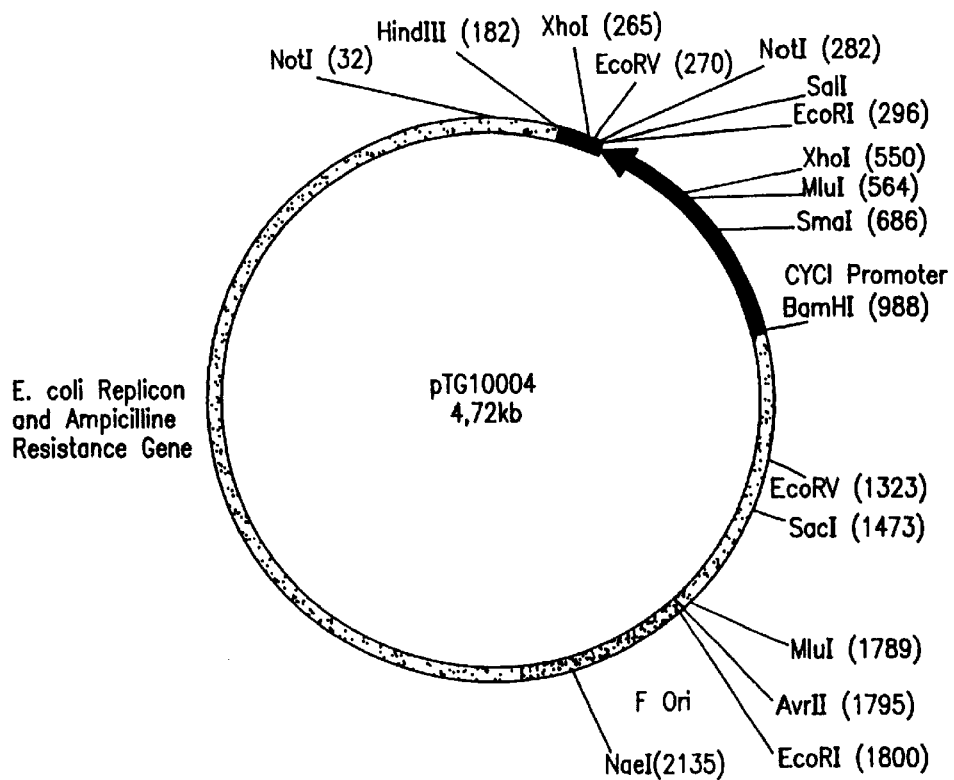
Figure 48:
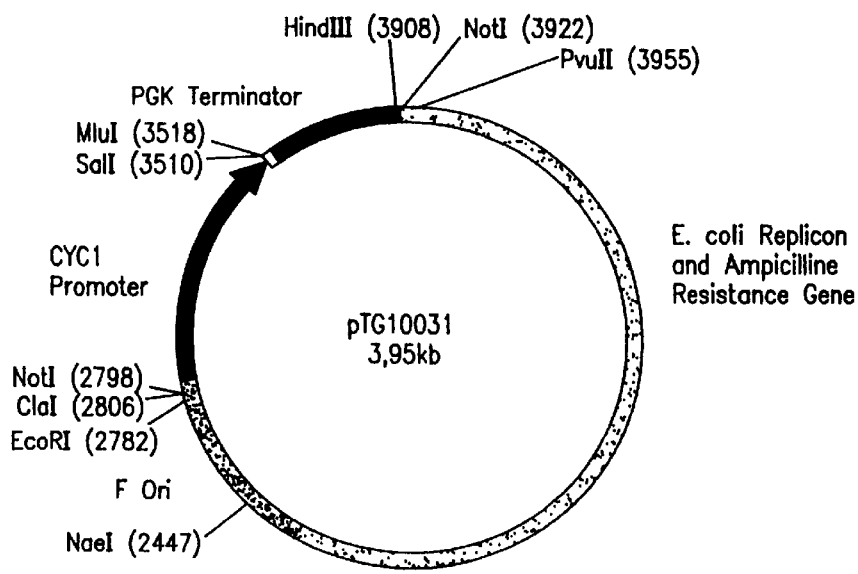
Figure 49:
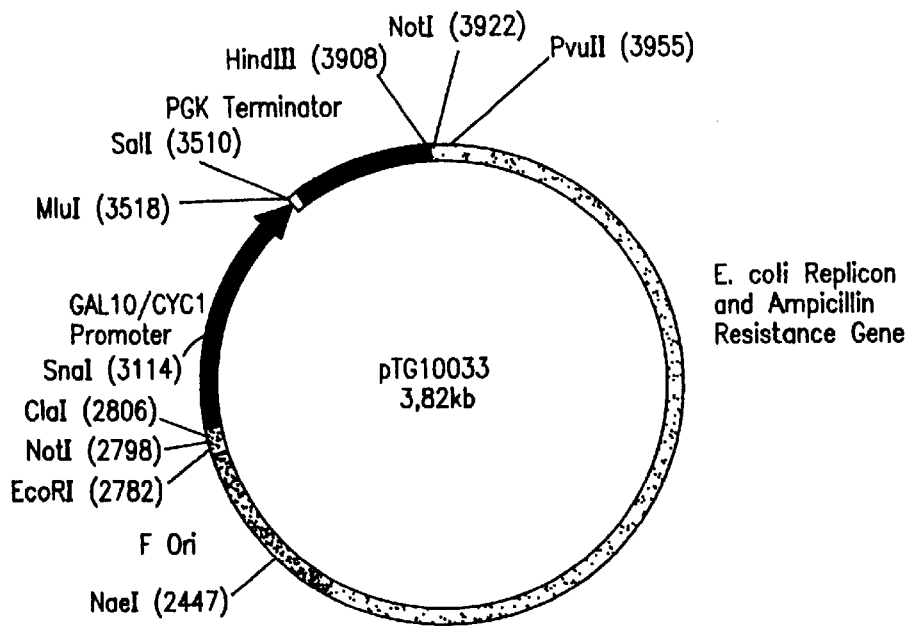
Figure 50:
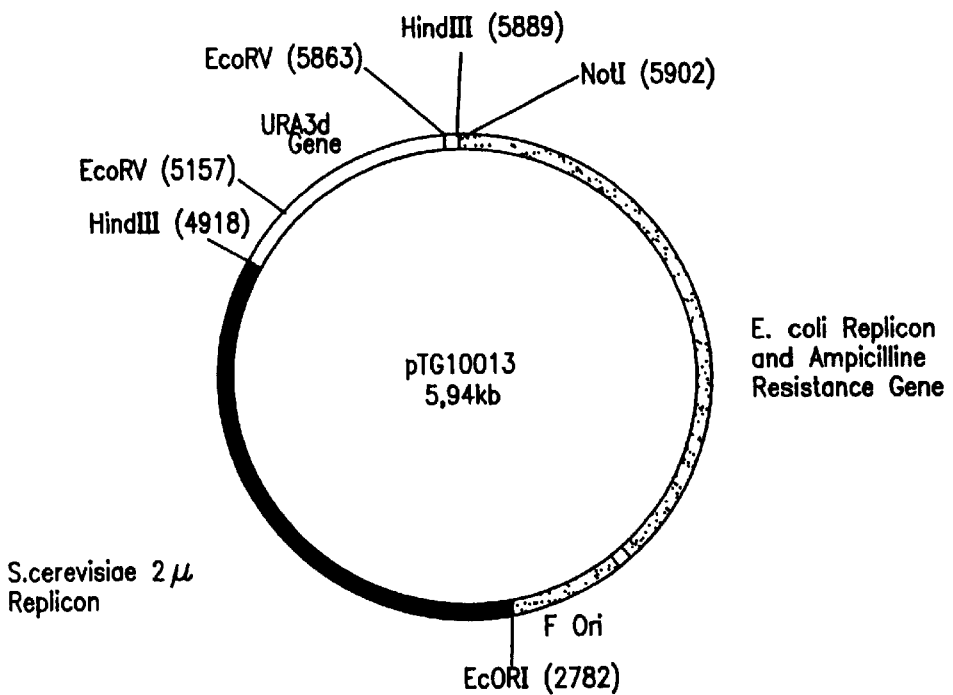
Figure 51:
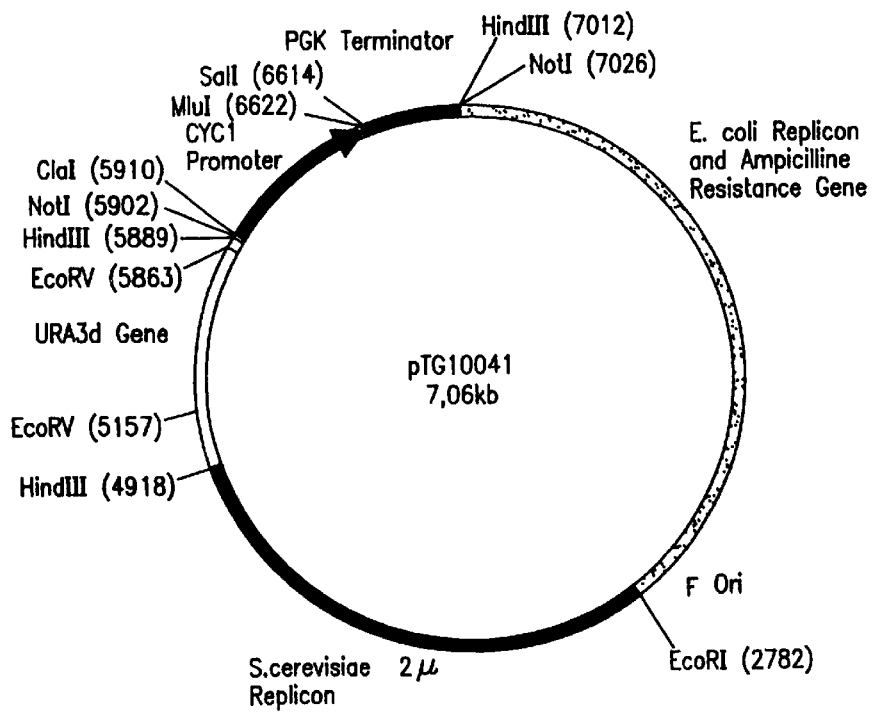
Figure 52:
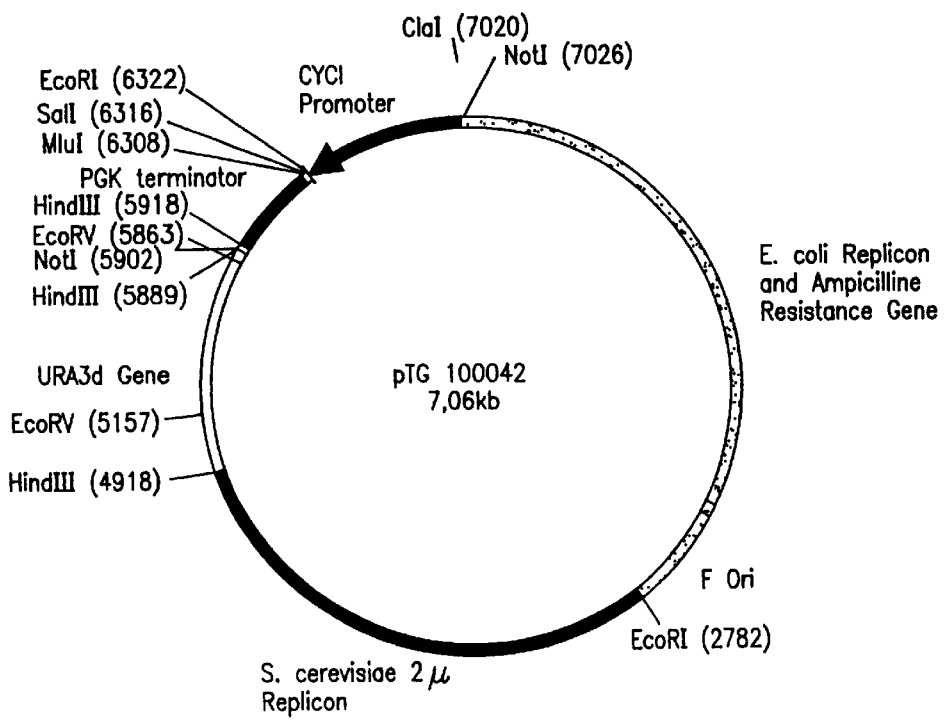
Figure 53:
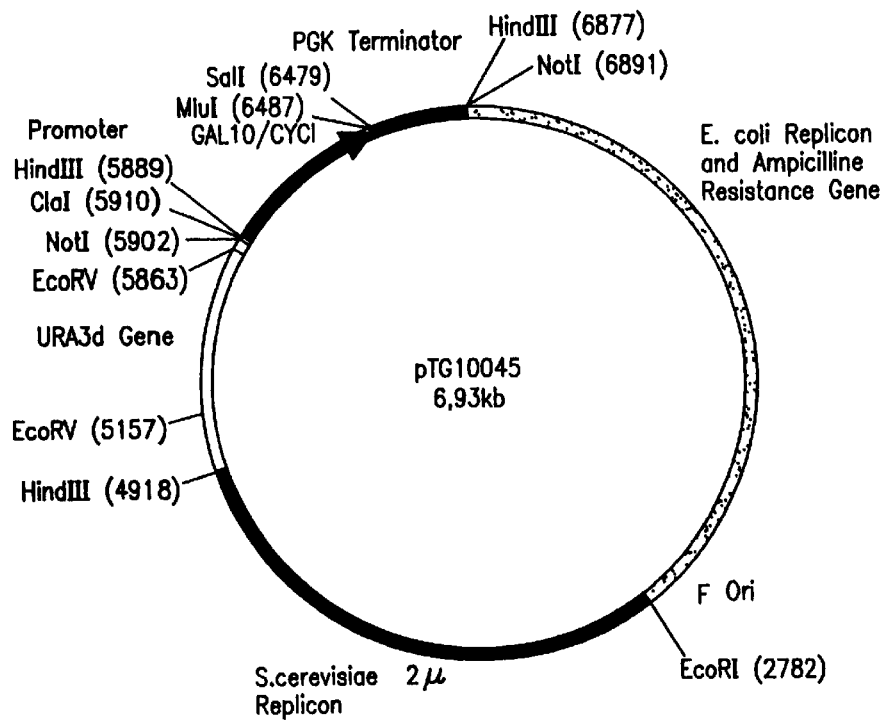
Figure 54:
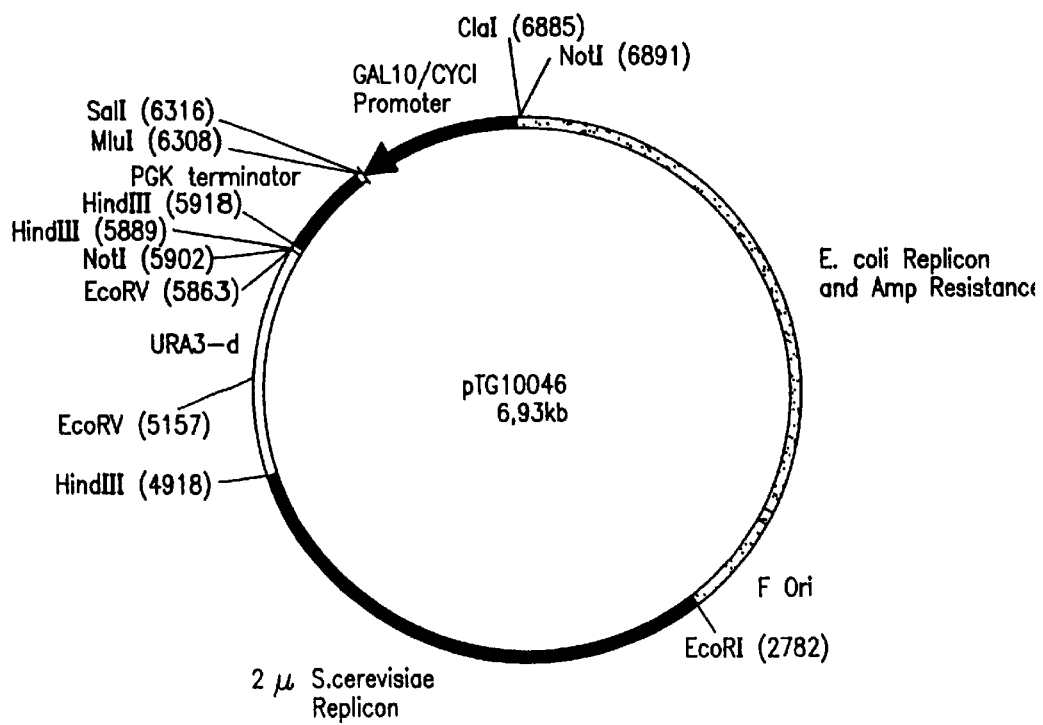
Figure 55:
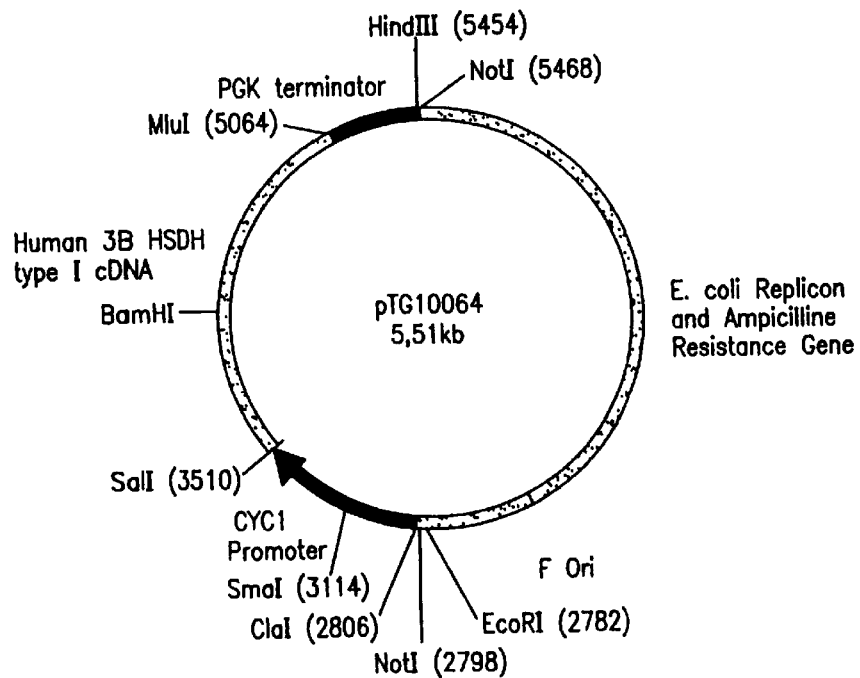
Figure 56:
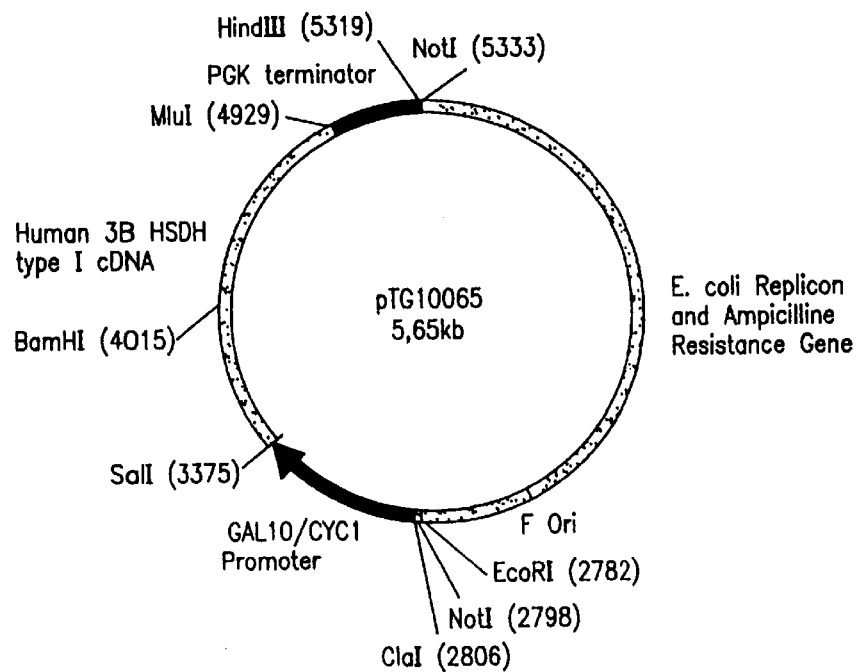
Figure 57A:
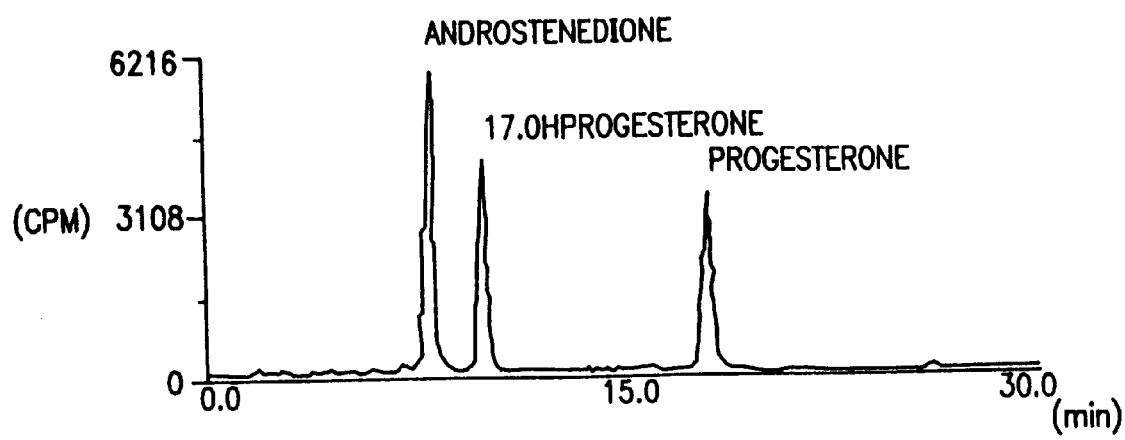
Figure 57B:
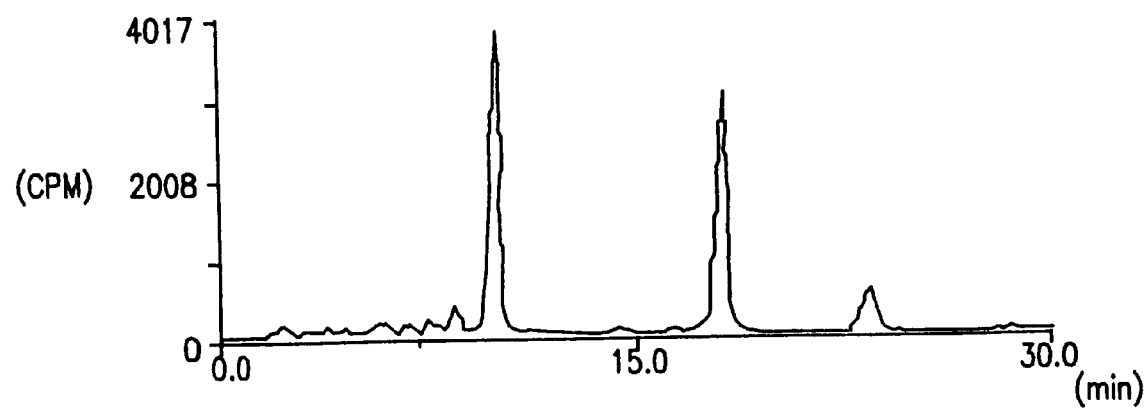

FIG. 45 shows a physical map of the plasmid pTG7453.
FIG. 46 shows a physical map of the plasmid pTG10014.
FIG. 47 shows a physical map of the plasmid pTG10004.
FIGS. 48 and 49, respectively show a physical map of the plasmid pTG10031 and pTG10033.
FIG. 50 shows a physical map of the plasmid pTG10013.
FIGS. 51 and 52, respectively show a physical map of the plasmid pTG10041 and pTG10042.
FIGS. 53 and 54, respectively show a physical map of the plasmid pTG10045 and pTG10046.
FIGS. 55 and 56, respectively show a physical map of the plasmid pTG10064 and pTG10065.
FIG. 57 is RP-HPLC analysis of Example 34.

The invention comprises the preparation and culturing of cells which are suited to be used in large scale biochemical production reactors and the use of these cells for the oxidation of compounds and particularly for the production of steroids, shown in FIG. 1. Each of the depicted reactions can be carried out separately. Also interchange of steps in a multi-step reaction is included in the invention. Micro-organisms are preferred hosts but other cells may be used as well as cells of plants or animals, optionally applied in a cell culture or in the tissue of living transgenic plants or animals.

The cells of the invention are obtained by the genetic transformation of suitable receptor cells, preferably cells of suited micro-organisms, with vectors containing DNA sequences encoding the proteins involved in the conversion of cholesterol to hydrocortisone, comprising side-chain cleaving enzyme ($P_{450}SCC$), adrenodoxin (ADX), adrenodoxin reductase (ADR), 3β-hydroxy-steroid dehydrogenase/isomerase (3β-HSD), steroid-17α-hydroxylase ($P_{450}17\alpha$), NADPH cytochrome $P_{450}$ reductase (RED), steroid-21-hydroxylase ($P_{450}C21$) and steroid-lip-hydroxylase ($P_{450}11\beta$). Some host cells may already produce on their own one or more of the necessary proteins at a sufficient level and therefore have to be transformed with the supplementary DNA sequences only. Such possible own proteins are ferredoxin, ferredoxin reductase, $P_{450}$-reductase, and 3β-hydroxy-steroid dehydrogenase/isomerase.

For retrieval of the sequences which encode proteins which are involved in the conversion of cholesterol to hydrocortisone, suitable DNA sources have been selected. An appropriate source for the retrieval of DNA encoding all proteins involved in the conversion of cholesterol to hydrocortisone is the adrenal cortex tissue of vertebrates e.g. bovine adrenal cortex tissue. Also from various micro-organisms, the relevant DNA can be retrieved, e.g. from *Pseudomonas testosteroni*, *Streptomyces griseocarneus* or *Brevibacterium sterolicum* for DNA encoding the 3β-hydroxy-steroid dehydrogenase/isomerase and from *Curvularia lunata* or *Cunninghamella blakesleeana* for DNA encoding proteins involved in the 11β-hydroxylation of cortexolone. The DNA-sequences coding for the proteins bovine $P_{450}SCC$, bovine $P_{450}11\beta$ or a microbial equivalent protein, bovine adrenodoxin, bovine adrenodoxin reductase, 3β-hydroxy-steroid dehydrogenase/isomerase of bovine or microbial origin, bovine $P_{450}17\alpha$, bovine $P_{450}C21$ and NADPH cytochrome $P_{450}$ reductase of bovine or microbial origin, were isolated according to the following steps:

1. Eukaryotic sequences (cDNA's)
   a. Total RNA was prepared from appropriate tissue.
   b. PolyA$^+$ containing RNA was transcribed into double stranded cDNA and ligated into bacteriophage vectors.
   c. The obtained cDNA library was screened with $^{32}$P-labeled oligomers specific for the desired cDNA or by screening an isopropyl-β-D-thiogalactopyranoside (IPTG)-induced lambda-gt11 cDNA library using a specific ($^{125}$I-labeled) antibody.
   d. cDNA inserts of positive plaque forming units (pfu's) were inserted into appropriate vectors to verify:
      the entire length of the cDNA by nucleotide sequencing.
2. Prokaryotic genes
   a. Genomic DNA was prepared from an appropriate micro-organism.
   b. To obtain a DNA library, DNA fragments were cloned into appropriate vectors and transformed to an appropriate *E.coli* host.
   c. The DNA library was screened with $^{32}$P-labeled oligomers specific for the gene of interest or by screening an IPTG-induced lambda-gt11 cDNA library using a specific ($^{125}$I-labeled) antibody.
   d. Plasmids of positive colonies were isolated and inserted DNA fragments subcloned into appropriate vectors to verify:
      the entire length of the gene.

Note: According to an improved method, the particular cDNA (eukaryotic sequences) or gene (prokaryotic sequences) was amplified using two specific oligomers by the method known as the polymerase chain reaction (PCR) (Saiki et al, Science, Vol. 239, pp. 487–491, 1988). Subsequently, the amplified cDNA or DNA was inserted into the appropriate vectors.

According to one aspect of the invention, suitable expression cassettes are provided in which the heterologous DNA isolated by the previous procedure is placed between suitable control sequences for transcription and translation, which enables the DNA to be expressed in the cellular environment of a suitable host, affording the desired protein or proteins. Optionally, the initiation control sequences are followed by a secretion signal sequence. Suitable control sequences have to be introduced together with the structural DNA by said expression cassettes. Expression is made possible by transformation of a suitable host cell with a vector containing control sequences which are compatible with the relevant host and are in operable linkage to the coding sequences of which expression is desired.

Alternatively, suitable control sequences present in the host genome are employed. Expression is made possible by transformation of a suitable host cell with a vector containing coding sequences of the desired protein flanked by host sequences enabling homologous recombination with the host genome in such a manner that host control sequences properly control the expression of the introduced DNA.

As is generally understood, the term control sequences comprises all DNA segments which are necessary for the proper regulation of the expression of the coding sequence to which they are operably linked, such as operators, enhancers and, particularly, promoters and sequences which control the translation.

The promoter may or may not be controllable by regulating its environment. Suitable promoters for prokaryotes include, for example, the trp promoter (inducible by tryptophan deprivation), the lac promoter (inducible with the galactose analog IPTG), the β-lactamase promoter, and the phage derived $P_L$ promoter (inducible by temperature variation). Additionally, especially for expression in Bacillus, useful promoters include those for alpha-amylase, protease, Spo2, spac and Ø105 and synthetic promoter sequences. A preferred promoter is the one depicted in FIG. 5 and denoted with "HpaII".

Suitable promoters for expression in yeast include the 3-phospho-glycerate kinase promoter and those for other glycolytic enzymes, as well as promoters for alcohol dehydrogenase and yeast phosphatase. Also suited are the promoters for transcription elongation factor (TEF) and lactase. Mammalian expression systems generally employ promoters and the SV40 promoter but they also include regulatable promoters such as the metallothionein promoter, which is controlled by heavy metals or gluco-corticoid concentration. Presently, viral-based insect cell expression systems are also suited, as well as expression systems based on plant cell promoters such as the nopaline synthetase promoters.

Translation control sequences include a ribosome binding site (RBS) in prokaryotic systems, whereas in eukaryotic systems translation may be controlled by a nucleotide sequence containing an initiation codon such as AUG.

In addition to the necessary promoter and the translation control sequence, a variety of other control sequences, including those regulating termination (for example, resulting in polyadenylation sequences in eukaryotic systems) may be used in controlling expression. Some systems contain enhancer elements which are desirable, but mostly not obligatory, in effecting expression.

The invention also discloses expression cassettes containing still another heterologous coding sequence encoding an enzyme which catalyzes, alone or in cooperation with one or more additional proteins, another step of the pathway of FIG. 1.

A group of vectors denoted with pGBSCC-n, where "n" is any integer from 1 to 17, is especially developed for the DNA encoding the $P_{450}SCC$ enzyme.

Another group of vectors denoted with pGB17α-n, where "n" is any integer from 1 to 5, is especially developed for the DNA encoding the $P_{450}17\alpha$ enzyme.

A further group of vectors denoted with pGBC21-n, where "n" is any integer from 1 to 9, is especially developed for the DNA encoding the $P_{450}C21$ enzyme.

Still another group of vectors denoted with pGB11β-n, where "n" is any integer from 1 to 4, is especially developed for the DNA encoding the $P_{450}11\beta$ enzyme.

According to a further aspect of the invention, suitable host cells have been selected which accept the vectors of the invention and allow the introduced DNA to be expressed. When culturing the transformed host cells, the proteins involved in the conversion of cholesterol to hydro-cortisone appear in the cell contents. The presence of the desired DNA can be proven by DNA hybridizing procedures, their transcription by RNA hybridization, their expression by immunological assays and their activity by assessing the presence of oxidized products after incubation with the starting compound in vitro or in vivo.

Transformed microorganisms are preferred hosts, particularly bacteria (more preferably *Escherichia coli* and Bacillus and Streptomyces species) and yeasts (such as Saccharomyces and Kluyveromyces). Other suitable host organisms are found among plants and animals, comprising insects, of which the isolated cells are used in a cell culture, such as COS cells, $C_{127}$ cells, CHO cells, and *Spodoptera frugiperda* (Sf9) cells. Alternatively, a transgenic plant or animal is used.

A particular type of recombinant host cells are the ones in which either two or more expression cassettes of the invention have been introduced or which have been transformed by an expression cassette coding for at least two heterologous proteins, enabling the cell to produce at least two proteins involved in the pathway of FIG. 1.

A major feature of the invention is that the prepared novel cells are not only able to produce the proteins involved in the oxidative conversion of steroids resulting eventually into hydrocortisone, but also to use these proteins on the spot in the desired oxidative conversion of the corresponding substrate compound added to the culture liquid. Steroids are preferred substrates. The cells transformed with the heterologous DNA are especially suited to be cultured with the steroids mentioned in FIG. 1, including other sterols such as β-sitosterol. As a result, oxidized steroids are obtained.

Depending on the presence in the host cell of a multiplicity of heterologous DNA encoding proteins involved in the pathway of FIG. 1, several biochemical conversions result comprising the side-chain cleaving of a sterol and/or oxidative modifications of C11, C17, C3 and C21. Therefore, the expression cassettes of the invention are useful in constructing a multigenic system which can effect successive intra-cellular transformations of the multiple steps in the sequence as depicted in FIG. 1. It may be necessary to introduce into the desired host expression cassettes which encode in their entirety the required proteins. In some instances, one or more of the proteins involved in the pathway may already be present in the host as a natural protein exerting the same activity. For example, ferredoxin, ferredoxin reductase and $P_{450}$ reductase may already be present in the host. Under those circumstances, only the remaining enzymes must be provided by recombinant transformation.

As an alternative to biochemical conversions in vivo, the proteins involved in the conversion of cholesterol to hydrocortisone are collected, purified as far as necessary, and used for the in vitro conversion of steroids in a cell free system, e.g. immobilized on a column. Alternatively, the more or less purified mixture containing one or more enzymes of the pathway is used as such for steroid conversion. One exemplified host contains DNA encoding two heterologous proteins viz. the enzyme $P_{450}SCC$ and the protein ADX necessary for the production of pregnenolone. In comparison with a host with only $P_{450}SCC$ DNA, the yield of pregnenolone in a cell-free extract after adding ADR, NADPH and cholesterol is considerably improved.

The present invention provides expression cassettes necessary for the construction of a one-step production process for several useful steroids. Starting from cheap and abundantly available starting compounds, it is especially suited from the production of hydrocortisone and intermediate compounds. The invention renders obsolete traditional expensive chemical reactions. Intermediate compounds need not be isolated. Apart from the novel host cells, the processes used for culturing these cells on behalf of steroid conversions are analogous to bio-technological procedures well known in the art.

It has now been accomplished to clone in one host organism, the genes which code for the proteins which are able to catalyze two separate oxidations on the steroid molecule and particularly for the proteins shown in FIG. 1. In particular, it has been realized to clone the proteins responsible for the steroid 17α-hydroxylation and for the steroid C21-hydroxylation in one and the same host organism and to have said host organism express said proteins in a functional form. Moreover, in another aspect of the invention, a process is provided in which said transformed micro-organisms when grown in a fermentation medium oxidize a steroid substrate present in the medium simultaneously at two different positions of the steroid molecule. In particular, a one-step process is achieved for the introduction of the 17α- as well as the 21-hydroxyl group.

A preferred host organism is *Kluyveromyces lactis* or is *Saccharomyces cerevisiae*, but other host organisms and in particular micro-organisms, especially those previously mentioned, can be used. More particularly, the micro-organisms are suitable which have been described above for cloning and expressing the genes of the biochemical pathway as shown in FIG. 1.

One way to prepare a host able to carry out a multiple steroid oxidation is to transform the host with two or more vectors, each containing the gene for one oxidation step. One exemplified transformed host contains DNA encoding the $P_{450}$ 17α and 3β-HSDH proteins. Another way is to have the host transformed by one vector containing an expression cassette with all genes coding for the proteins necessary for the desired multiple oxidation reaction. According to the invention, the expression cassette contains at least two structural genes, each flanked by proper control sequences. One exemplified expression cassette contains DNA encoding the proteins $P_{450}$17α and $P_{450}$-C21 (pGB17-α/C21-1).

Using the method of the invention it is possible, using methods known in the art, to prepare analogous expression cassettes and host cells containing them, with which it is possible to carry out other multiple steroid oxidations and eventually the conversion of cholesterol into hydrocortisone in a single fermentation process.

In another embodiment of the invention, the 3β-hydroxy-5-ene steroid dehydrogenase and 5-ene-4-ene steroid isomerase (3β HSDH) form a bifunctional enzyme which catalyzes two independant reactions transforming pre-genenolone into progesterone. The protein of 42 kD is encoded by a single open reading frame. cDNA's and/or genes have been cloned from human (Lachance et al., J. Biol. Chem. 265 (1990) p 20469–20475 ; Lachance et al., DNA Cell Biol. 10 (1991) p 701–711), bovine (Zhao et al., FEBS lett. 259 (1989) p 153–157) and rat (Zhao et al., J. Biol. Chem. 266 (1990) p 583–593; Simard J. et al., J. Biol. Chem. 266 (1991) p 14842–14845). The determined N-terminus corresponds to the deduced amino acid sequence. In human, two types have been described: type I 3β HSDH has been isolated from placenta and is also expressed in skin; type II 3β HSDH was isolated from adrenals and gonads. Nucleotide homologies between exons 1 till 4 are 77.1, 91.8, 94 and 94% respectively and 94% at the amino acid level. After expression in HeLa cells of the respective cDNA's, it was found that the type I enzyme is more active (Vmax/Km) on pregenenolone, DHEA (dehydroepiandrosterone) and DHT (dihydrotestosterone). This is primarily due to a lower Km, e.g. for pregnenolone (0.24 versus 1.2 μM). Even in the absence of a mitochondrial targetting sequence, the 3β HSDH enzymes are known as membrane-associated proteins, located in microsomal as well as in mitochondrial membranes.

In the following examples, there are described several preferred embodiments to illustrate the invention. However, it should be understood that the invention is not intended to be limited to the specific embodiments.

EXAMPLE 1

Molecular cloning of a full-length cDNA encoding the bovine cytochrome $P_{450}$ side chain cleavage enzyme ($P_{450}$SCC)

General cloning techniques as well as DNA and RNA analyses have been used as described in the handbook of T. Maniatis et al., Molecular Cloning, Cold Spring Harbor Laboratory, 1982. Unless described elsewhere, all DNA modifying enzymes, molecular cloning vehicles and *E.coli* strains were obtained from commercial suppliers and used according to the manufacturer's instructions. Materials and apparatus for DNA and RNA separation and purification were used according to instructions of the suppliers.

Bovine adrenal cortex tissue was prepared from freshly obtained bovine kidneys, quickly frozen in liquid nitrogen and stored at −80° C. From frozen bovine adrenal cortex, total cellular RNA was prepared as described by Auffrey et al (Eur. J. Biochem., Vol. 107, p. 303–314, 1980). Adrenal poly A+ RNA was obtained by heating the total RNA sample at 65° C. before polyA selection on oligo(dt) chromatography.

DNA's complementary to polyA$^+$ RNA from bovine adrenal cortex were synthesized as follows: 10 μg of polyA$^+$ RNA, treated with methylmercuric hydroxide were neutralized with β-mercaptoethanol and the mixture was adjusted to 50 mM Tris/HCl (pH 8.3 at 42° C.), 40 mM KCl, 6 mM $MgCl_2$, 10 mM DTT, 3000 U RNasin/ml, 4 mM $Na_4P_2O_7$, 50 μg actinomycine D/ml, 0.1 mg oligo(dT$_{12-18}$)/ml, 0.5 mM dGTP, 0.5 mM dATP, 0.5 mM dTTP, 0.25 mM dCTP and 400 μCi α $^{32}$P-dCTP/ml, all in a final volume of 100 μl. The mixture was put on ice for 10 minutes, heated for 2 minutes at 42° C. and the synthesis was started by addition of 150 U AMV reverse transcriptase (Anglian Biotechnology Ltd.); incubation was performed for 1 hour at 42° C.

Second strand synthesis was performed by adding DNA polymerase and RNase H according to Gubler et al (Gene, Vol. 25, pp. 263–269, 1983). After treatment of the ds DNA with T4 DNA polymerase (BRL) to obtain blunt ends, decameric EcoRI linkers (Biolabs Inc.) were ligated to the ds DNA fragments. After digestion with EcoRI-linkers by Biogel A15 m (Bio-Rad) chromatography. Approximately 200 ng EcoRI-linker containing double stranded cDNA was ligated with 10 μg of EcoRI digested and calf intestine-phosphatase (Boehringer) treated with lambdagt11 vector DNA (Promega) by T4-DNA ligase (Boehringer) as described by Huynh et al. (In: "DNA cloning techniques: A practical approach", pp. 49–78, Oxford IRL-press, 1985). Phages obtained after in vitro packaging of the ligation mixture were used to infect the *E.coli* Y1090 host (Promega)

Figure 2:
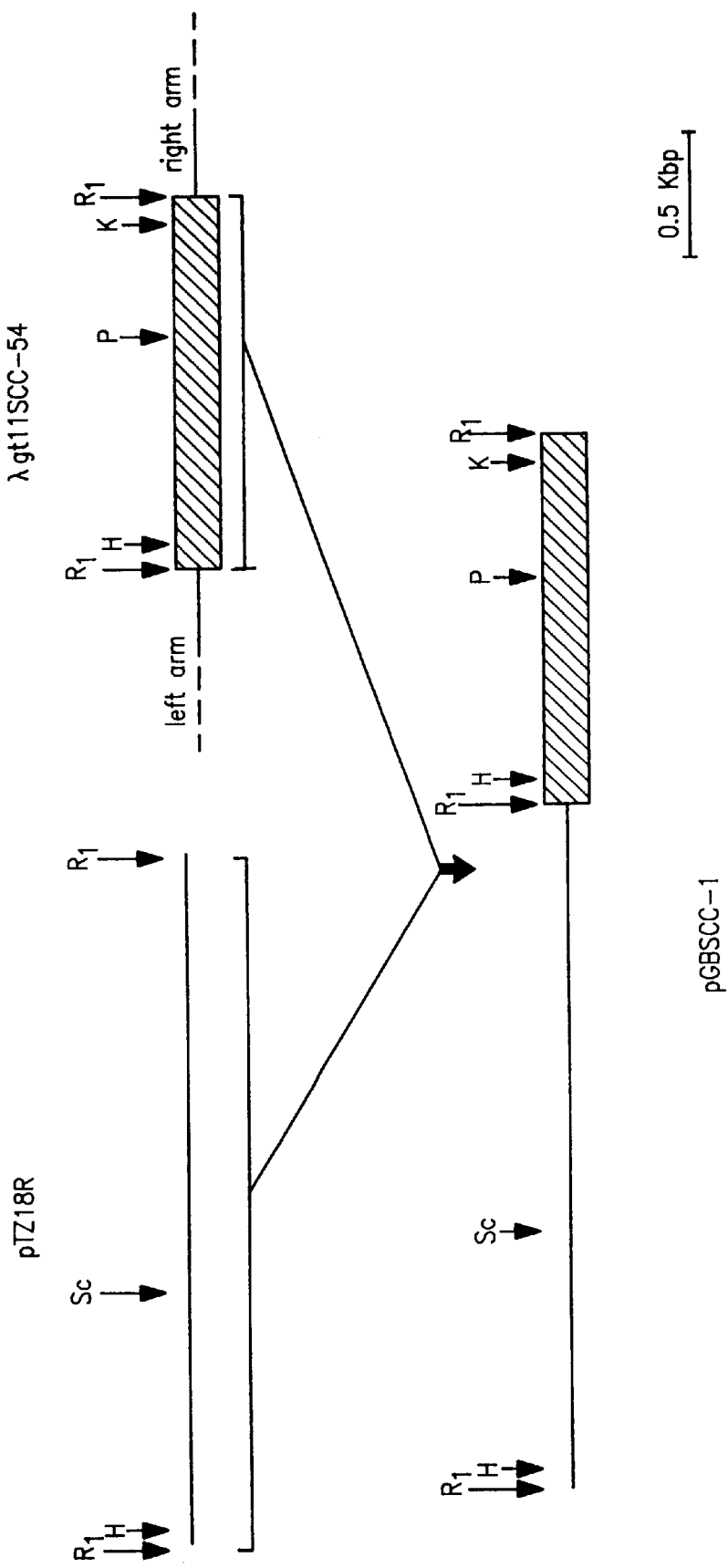
FIG. 2 shows the construction of plasmid pGBSCC-1. The $P_{450}$SCC-sequences are indicated in a box (▨).

From this cDNA library, approximately $10^6$ plaque forming units (pfu's) were screened with a $^{32}$P-end labeled synthetic oligomer SCC-1 (5'-GGC TGA CGA AGT CCT GAG ACA CTG GAT TCA GCA CTGG-3') (SEQ ID NO: 1), specific for bovine $P_{450}$SCC DNA sequences as described by Morohashi et al. (Proc. Natl. Acad. Sci. USA, Vol. 81, pp. 4647–4651, 1984). Six hybridizing pfu's were obtained and further purified by two additional rounds of infection, plating and hybridization. The $P_{450}$SCCcDNA EcoRI inserts were subcloned into the EcoRI site of pTZ18R (Pharmacia). Clone pGBSCC-1 (FIG. 2), containing the largest EcoRI insert (1.4 kb), derived from the clone lambdagt11 SCC-54 was further analyzed by restriction enzyme mapping and sequencing.

The sequence data revealed that the pGBSCC-1 EcoRI insert was identical with the nucleotide sequence of SCCcDNA between positions 251 and 1824 on the $P_{450}$SCCcDNA map as described by Morohashi et al.

Figure 3:
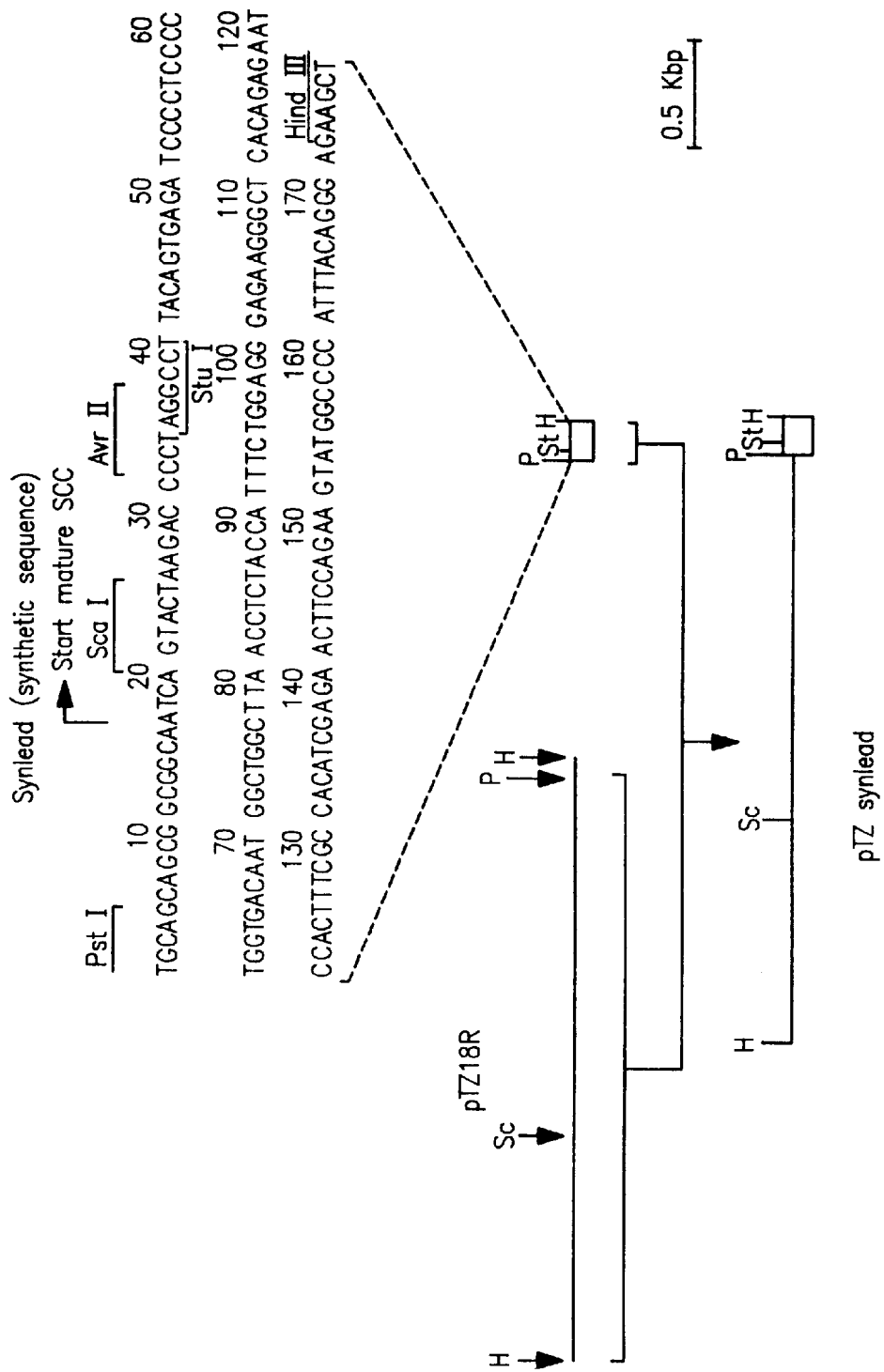
FIG. 3 shows the insertion of a synthetically derived PstI/HindIII fragment (SEQ ID NO: 2) containing the 5'-$P_{450}$SCC-sequences into the plasmid pTZ18R to obtain the plasmid pTZ synlead.

The remaining 5'-$P_{450}$SCCcDNA nucleoptides were synthetically derived by cloning a 177 bp Pst HindIII fragment (SEQ ID NO: 2) into the appropriate sites of pTZ18R, resulting in the pTZ/syn lead as shown in FIG. 3, containing besides the nucleotides coding for the mature $P_{450}SCC$ protein from position 188 to 273 as published by Morohashi et al., additional restrictive sites for ScaI, AvrII and StuI without affecting the predicted amino acid sequence of the $P_{450}SCC$ protein.

Figure 4:
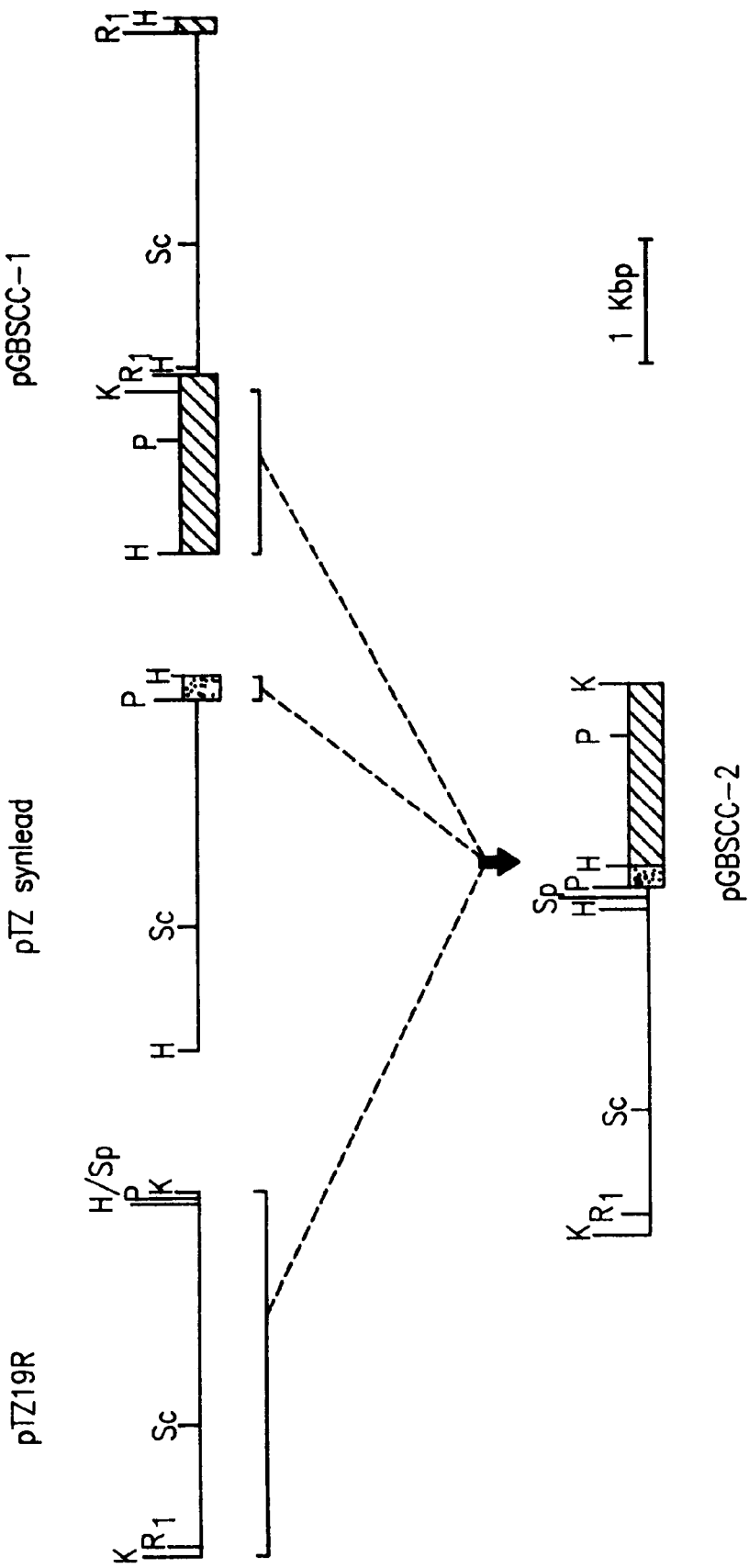
FIG. 4 shows the construction of a full-length $P_{450}$SCC cDNA of synthetically (▦) and by cDNA cloning (▨) derived $P_{450}$ SCC-sequences into pTZ18R to obtain pGBSCC-2.

The full-length $P_{450}SCCcDNA$ was constructed by molecular cloning in *E.coli* JM101 (ATCC 33876) of a ligation mixture containing the 1372 bp HindIII/KpnI pGBSCC-1 fragment, the 177 bp Pt/HindIII pTZ/syn lead fragment and pTZ19R DNA digested with PstI and KpnI. The resulting plasmid, pGBSCC-2, containing all nucleotide sequences encoding the mature bovine $P_{450}$ side chain cleavage protein is shown in FIG. 4.

EXAMPLE 2
Construction, transformation and expression of $P_{450}SCC$ in the bacterial host *Bacillus subtilis*

To derive expression of cytochrome $P_{450}SCC$ in a Bacillus host, $P_{450}SCCcDNA$ sequences were transferred to an *E.coli*/Bacillus shuttle vector pBHA-1.

Figure 6:
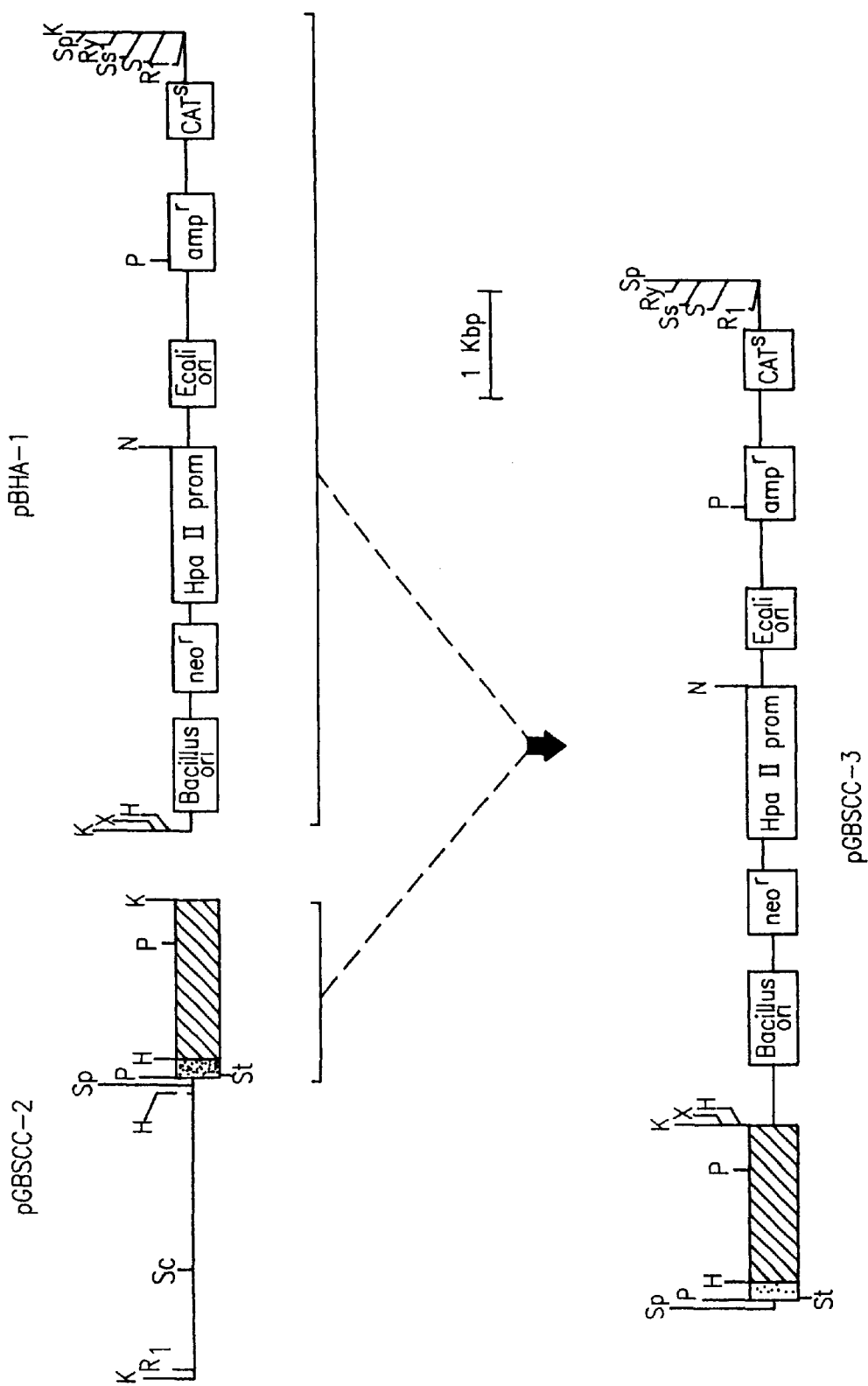
FIG. 6 is a schematic representation of the construction of pGBSCC-3. $P_{450}$SCC DNA sequences from plasmid pGBSCC-2 were introduced into the Bacillus/E.coli shuttle plasmid pBHA-1. Filled in boxes are as indicated in the legend of FIG. 4.

FIG. 5 shows the nucleotide sequence of the shuttle plasmid pBHA-1 (SEQ ID NO: 3). The plasmid consists of positions 11–105 and 121–215: bacteriophage FD terminator (double); positions 221–307: a part of plasmid pBR322 (viz. positions 2069–2153); positions 313–768: bacteriophage F1, origin of replication (viz. positions 5482–5943); positions 772–2571: part of plasmid pBR322, viz. the origin of replication and the p-lactamase gene; positions 2572–2685: transposon TN903, complete genome; positions 2719–2772: tryptophan terminator (double); positions 2773–3729: transposon Tn9, the chloramphenicolacetyl transferase gene. The nucleotides at position 3005 (A), 3038 (C), 3302 (A) and 3409 (A) differed from the wild type cat coding sequence. These mutations were introduced to eliminate the NcoI, BalI, EcoRI and PvuII sites: positions 3730–3804: multiple cloning site; positions 3807–7264: part of plasmid pUB110 containing the Bacillus "HpaII" promoter, the replication function and kanamycin resistance gene (EcoRI-PvuII fragment) (McKenzie et al., Plasmid, Vol. 15, pp 93–103, 1986 and McKenzie et al., Plasmid, Vol. 17, pp. 83–85, 1987); positions 7267–7331: multiple cloning site. The fragments were put together by known cloning techniques, e.g. filling in of sticky ends with Klenow, adapter cloning, etc. All data were derived from Genbank®, National Nucleic Acid Sequence Data Bank, NIH, USA.

pGBSCC-3 was derived by molecular cloning in *E.coli* JM101 of the KpnI/SphI $P_{450}SCCcDNA$ insert of pGBSCC-2 (described in Example 1) into the appropriate sites in pBHA-1 as indicated in FIG. 6.

By molecular cloning in *E.coli* JM101, the methionine initiation codon was introduced by exchanging the StuI SphI fragment (SEQ ID NO: 6) in pGBSCC-3 by a synthetically derived SphI/StuI fragment.

Figure 7:
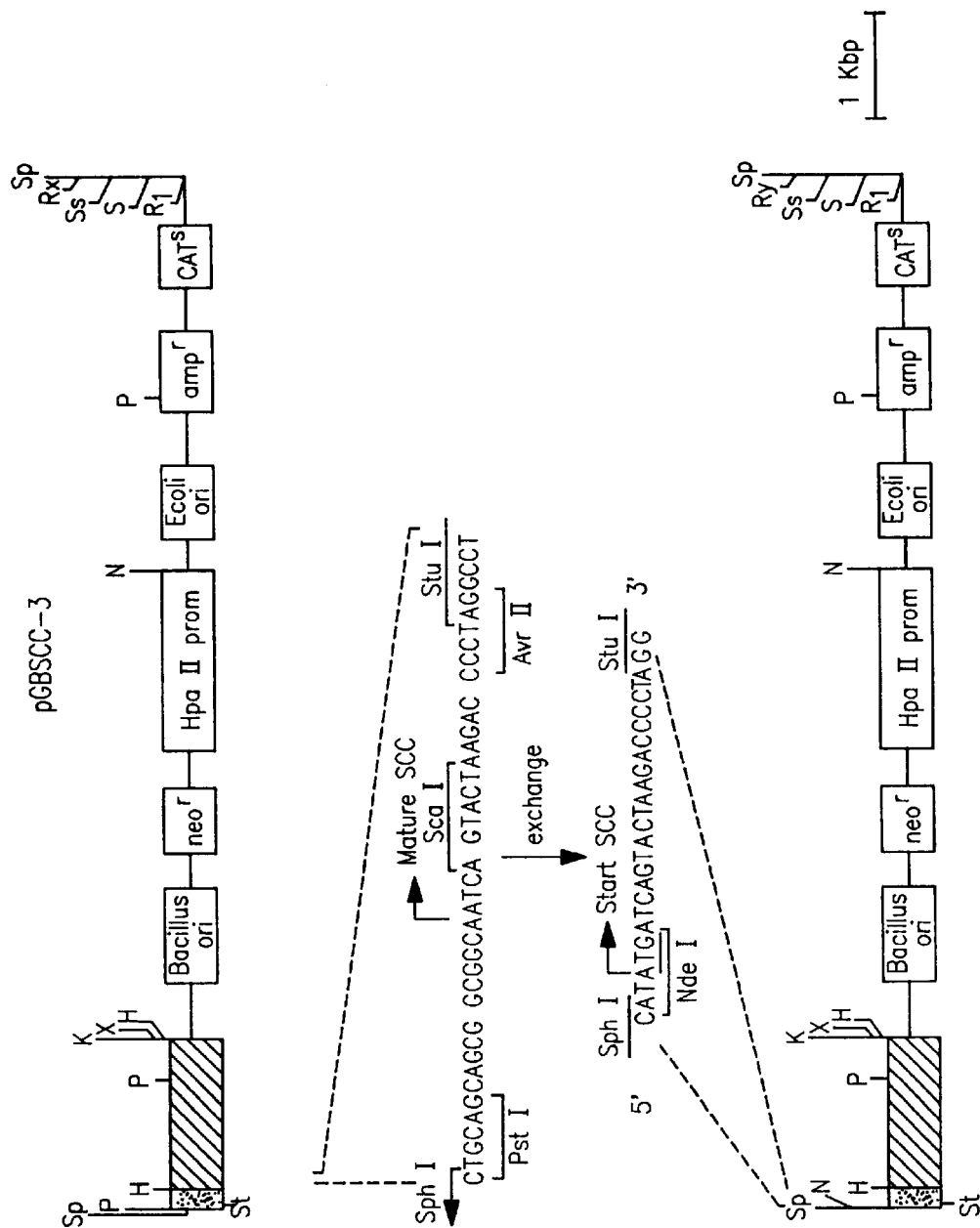
FIG. 7 shows the introduction of a NdeI restriction site (SEQ ID NO: 4) in recombination with an ATG start codon before the $P_{450}$SCC-maturation site (SEQ ID NO: 6) in pGBSCC-3 to obtain pGBSCC-4.
Figure 8:
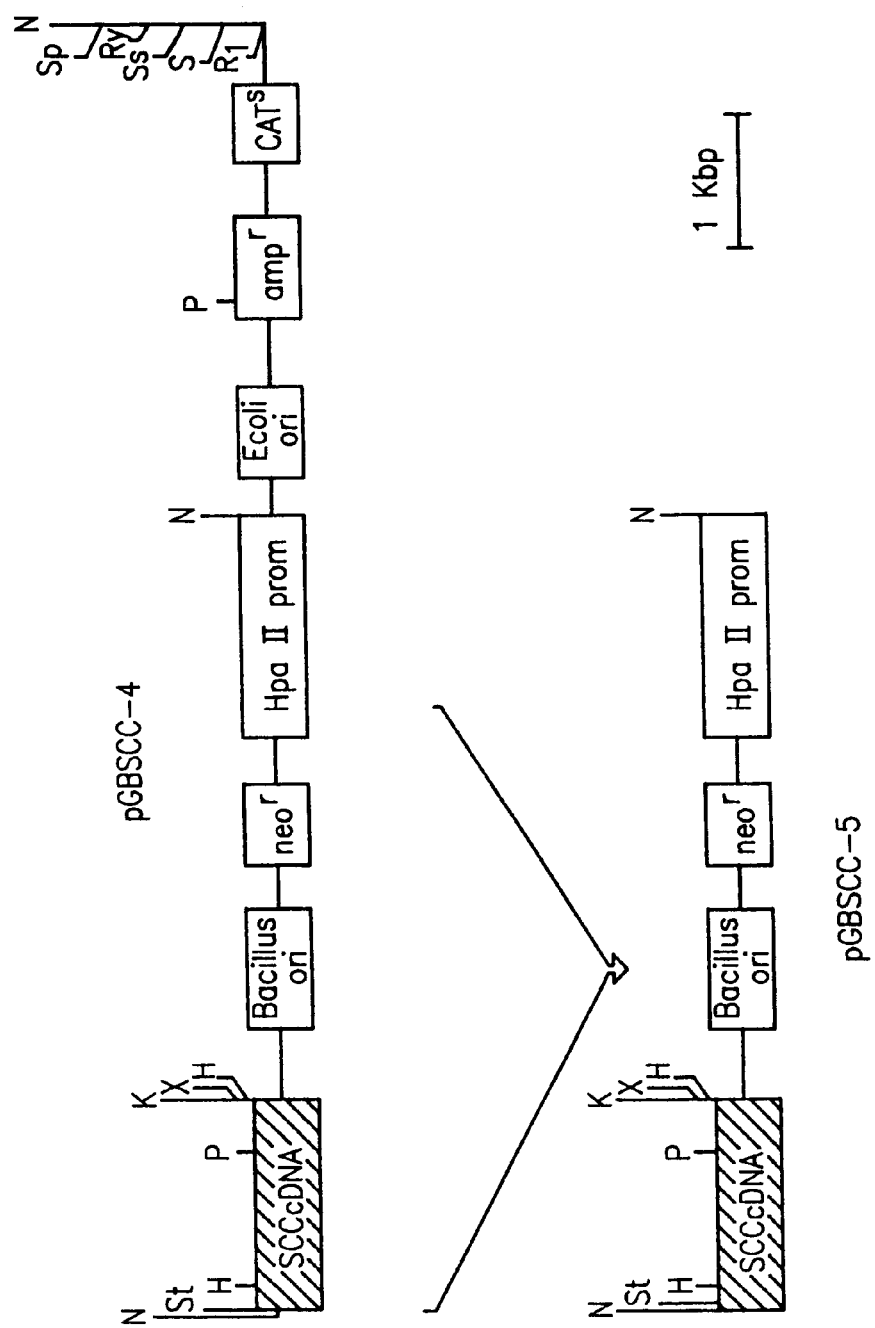
FIG. 8 shows a physical map of pGBSCC-5 which is obtained by removal of E.coli sequences from the plasmid pGBSCC-4.
Figure 9:
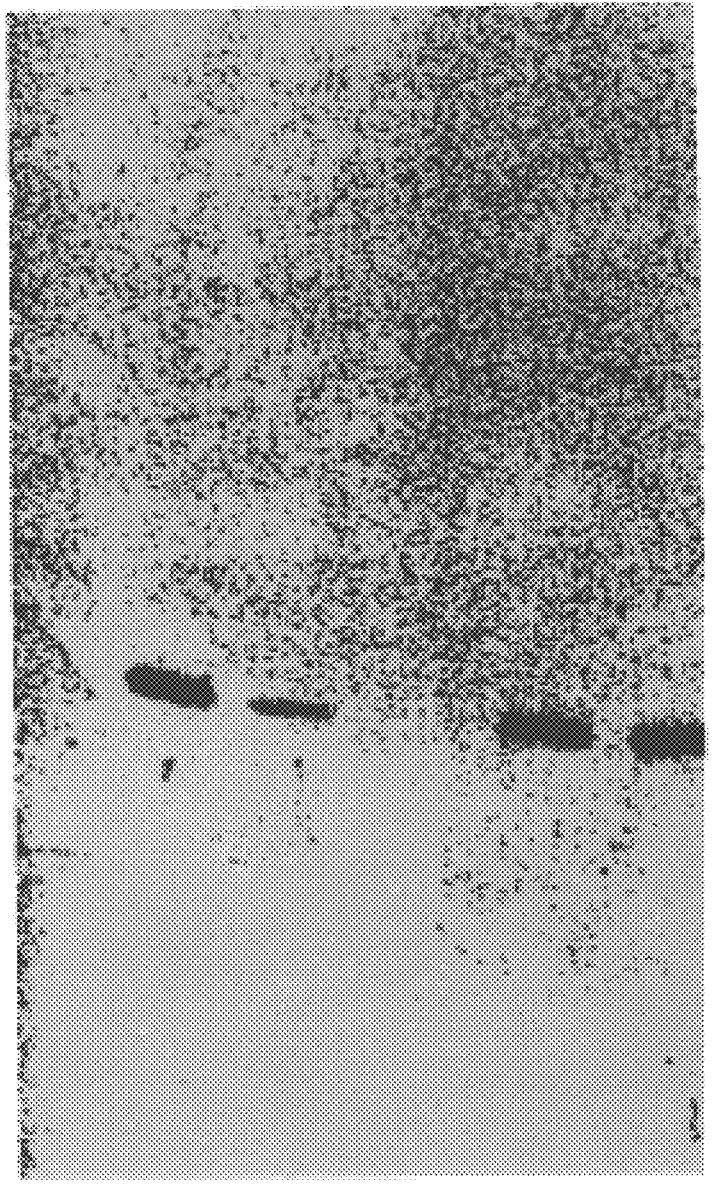
FIG. 9 shows a Western-blot probed with anti-bodies against $P_{450}$SCC, demonstrating the $P_{450}$SCC expression of plasmid pGBSCC-5 introduced in B.subtilis (lane c) and B.licheniformis (lane f). Control extracts from B.subtilis (lane c) a B.licheniformis are shown in lanes (a) and (d) resp. For comparison also purified adrenal cortex $P_{450}$SCC (30 ng) was added to these control extracts (lanes (b) and (e) resp.).

```
SPH  1                              STU  1
    CATATGATCAGTACTAAGACCCCTAGG         (SEQ ID NO:4)
    GTACGTATACTAGTCATGATTCTGGGGATCC     (SEQ ID NO:5)
       NDE 1
``` containing an NdeI site at the ATG initiation codon. The obtained plasmid pGBSCC-4 is shown in FIG. 7. The "Hpa II" Bacillus promoter was introduced upstream of $P_{450}SCCcDNA$ sequences by digestion of the *E.coli* part of the shuttle plasmid by agarose gel electrophoresis and subsequent religation and transformation into *Bacillus subtilis* 1A40 (BGSC 1A40) competent cells. Neomycin resistant colonies were analyzed and the plasmid pGBSCC-5 (FIG. 8) was obtained. Expression of bovine $P_{450}SCC$ was studied by preparing a cellular protein fraction of an overnight culture at 37° C. in TSB medium (Gibco) containing 10 µg/ml of neomycin. Cells of 100 µl of culture, containing approximately $5.10^6$ cells, were harvested by centrifugation and resuspended in 10 mM Tris/HCl pH 7.5. Lysis was performed by adding lysozyme (1 mg/ml) and incubation during 15 minutes at 37° C. After treatment with 0.2 mg DNase/ml during 5 minutes at 37° C., the mixture was adjusted to 1×SB buffer, as described by Laemmli, Nature, Vol. 227, pp. 680–685, 1970, in a final volume of 200 µl. After heating for 5 minutes at 100° C., 15 µl of the mixture was subjected to a 7.5% of SDS/polyacrylamide gel electrophoresis. As shown in FIG. 9 (lane C), a 53 kDa band could be detected after immunoblotting of the gel probed with $P_{450}SCC$ specific antibodies. Specific bovine $P_{450}SCC$ antibodies were obtained by immunization of rabbits with purified $P_{450}SCC$ protein isolated from bovine adrenal cortex tissue.

EXAMPLE 3
Expression of $P_{450}SCC$ in the bacterial host *Bacillus licheniformis*

Expression of bovine $P_{450}SCC$ in *B.licheniformis* was performed by transformation plasmid pGBSCC-5 into the appropriate host strain *B.licheniformis* T5 (CBS 470.83). A cellular protein fraction prepared as described in Example 2, from an overnight culture at 37° C. in Trypton Soy Broth (TSB) medium (Oxoid) containing 10 µg/ml of neomycin, was analyzed by SDS/PAGE and Western-blotting. As shown in FIG. 9 (lane f), a 53 kDa sized protein band was visualized after incubation of the nitrocellulose filter with antibodies specific for bovine $P_{450}SCC$. One transformant, SCC-201, was further analyzed for in vivo activity of $P_{450}SCC$ (see Example 11).

EXAMPLE 4
Expression of $P_{450}SCC$ in the bacterial host *Escherichia coli*
(a) Construction of the expression cassette To derive a suitable expression vector in the host *E.coli* for bovine $P_{450}SCC$, pTZ18R was mutated by site-directed mutagenesis as described by Zoller et al. (Methods in Enzymology, Vol. 100, pp. 468–500, 1983); Zoller et al. (Methods in Enzymolozy, Vol. 154, 329–350, 1987) and Kramer et al. (Methods in Enzymology, Vol. 154, pp. 350–367, 1987). Plasmids and strains for in vitro mutagenesis experiments were obtained from Pharmacia Inc.

Figure 10:
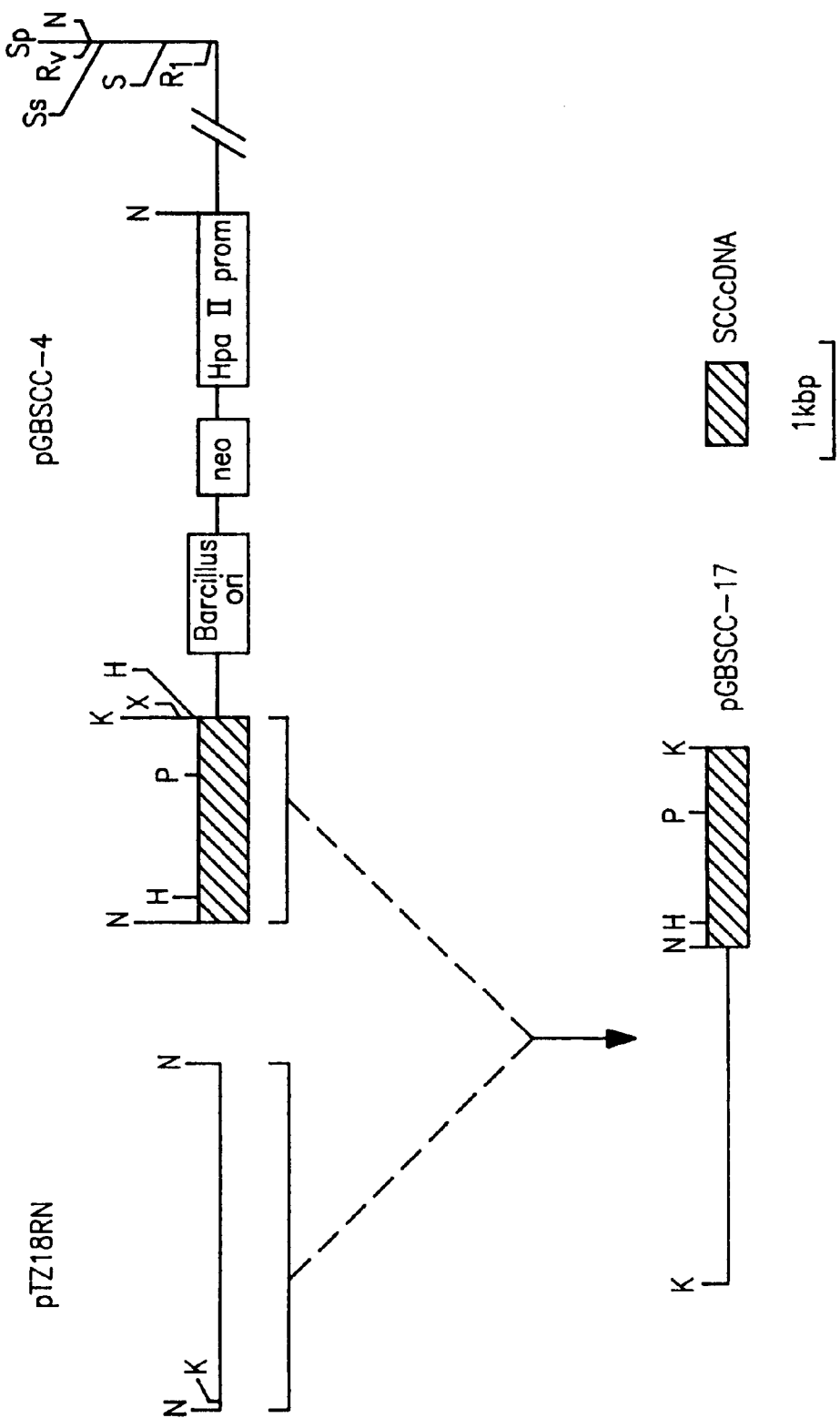
FIG. 10 is a schematic representation of the construction of pGBSCC-17. The coding $P_{450}$SCC-DNA sequences from plasmid pGBSCC-4 were introduced into the E.coli expression vector pTZ18RN. The $P_{450}$ SCC-sequences are indicated in a box (▨).

A synthetic derived oligomer with the sequence:

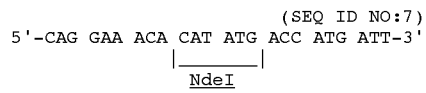

was used to create an NdeI restriction site at the ATG initiation codon of the lac Z gene in pTZ18R. The resulting plasmid pTZ18RN was digested with NdeI and KpnI and the NdeI/KpnI DNA fragment of pGBSCC-4 containing the full-length SCCcDNA, was inserted by molecular cloning as indicated in FIG. 10. The transcription of $P_{450}SCCcDNA$ sequences in the derived plasmid pGBSCC-17 will be driven by the E.coli lac-promoter.

(b) Expression of $P_{450}SCC$ in the host E.coli JM101 pGBSCC-17 was introduced into E.coli JM101 competent cells by selecting ampicillin resistant colonies. Expression of cytochrome $P_{450}SCC$ was studied by preparing a cellular protein fraction (described in Example 2) of transformants SCC-301 and 302 from an overnight culture at 37° C. in 2×TY medium (containing per liter of de-ionized water: Bacto tryptone (Difco), 16 g; yeast extract (DiFco), 10 g and NaCl, 5 g) containing 50 µg/ml of ampicillin.

Protein fractions were analyzed by SDS/PAGE stained with Coomassie brilliant blue (FIG. 11A) or by Western-blot and probed with antibodies specific for bovine $P_{450}SCC$ (FIG. 11B). Both analyses show a protein of the expected length (FIG. 11A, lanes 1 and 2 and in FIG. 11B, lanes 3 and 4) for the transformants SCC-301 and SCC-302, resp., which is absent in the E.coli JM101 control strain (FIG. 11A, lane 3 and FIG. 11B, lane 2).

EXAMPLE 5
Construction, transformation and expression of $P_{450}SCC$ in the yeast Kluyveromyces lactis (a) Introduction of the geneticin resistance marker in pUC19

A DNA fragment comprising the Tn5 gene (Reiss et al., EMBO J., Vol. 3, pp. 3317–3322, 1984) conferring resistance to geneticin under the direction of the alcohol dehydrogenase I (ADHI) promoter from S.cerevisiae, similar to that described by Bennetzen et al. (J. Biol. Chem., Vol. 257, pp. 3018–3025, 1982) was inserted into SmaI site of pUC19 (Yanisch-Perron et al., Gene., Vol. 33, pp. 103–119, 1985). The obtained plasmid, pUCG418, is shown in FIG. 12.

E.coli containing pUCG418 was deposited at Centraal Bureau voor Schimmelcultures under CBS 872.87.

(b) Construction of the expression cassette

A vector was constructed, comprising pUCG418 (for description see Example 5(a)) cut with XbaI and HindIII, the XbaI-SalI fragment from pGB901 containing the lactase promoter (see van den Berg et al., continuation-in-part of U.S. patent application Ser. No. 572,414: Kluyveromyces as a host strain) and synthetic DNA comprising part of the 3' noncoding region of the lactase gene of K.lactis. This plasmid, pGB950, is depicted in FIG. 13. pGB950 was cut with SalI and XhoI and synthetic DNA was inserted:

gen base (Difco laboratories) solution to an $OD_{610}$ of about 7. From 10 ml of the culture, the cells were collected by centrifugation, washed with TE-buffer (10-mM Tris-HCl pH 7.5; 0.1 mM EDTA) and resuspended in 1 ml of TE-buffer. An equal volume of 0.2 M lithium acetate was added and the mixture was incubated for 1 hour at 30° C. in a shaking waterbath. 15 µg of pGBSCC-7 was cut at the unique SacII site in the lactase promoter, ethanol precipitated and resuspended in 15 µl of TE-buffer. This DNA preparation was added to 100 µl of the pre-incubated cells and the incubation was prolonged for 30 minutes. Then, an equal volume of 70% PEG 4000 was added and the mixture was incubated for 1 hour at the same temperature, followed by a heat shock of 5 minutes at 42° C. Then, 1 ml of YEPD-medium was added and the cells were incubated for 90 minutes in a shaking waterbath of 30° C. Finally, the cells were collected by centrifugation, resuspended in 300 µl of YEPD and spread on agar plates containing 15 ml of YEPD agar with 300 µg/ml of geneticin and were overlayered 1 hour before use with 15 ml of YEPD-agar without G418. Colonies were grown for 3 days at 30° C.

(d) Analysis of the transformants

Transformants and the control strain CBS 2360 were grown in YEPD medium for about 64 hours at 30° C. The cells were collected by centrifugation, resuspended in a physiological salt solution of an $OD_{610}$ of 300 and disrupted by shaking with glass beads for 3 minutes on a Vortex shaker at maximum speed. Cell debris was removed by centrifugation for 10 minutes at 4500 rpm in a Hearaeus Christ minifuge GL. From the supernatants, 40 µl samples were taken for analysis on immunoblots (see FIG. 15A, lane 3 and FIG. 15B, lane 4).

The results show that a protein of the expected length is expressed in K.lactis cells transformed with pGBSCC-7. The transforman was denoted as K.lactis SCC-101.

EXAMPLE 6
Construction, transformation and expression of $P_{450}SCC$ in the yeast Saccharomyces cerevisiae (a) Construction of the expression cassette To delete the lactase promoter, pGB950 (see Example 4(b)) was cut with XbaI and SalI and the sticky ends were filled in using Klenow DNA polymerase and subsequently ligated. In the resulting plasmid, pGBSCC-8, the XbaI-site was destroyed, but the SalI site was maintained.

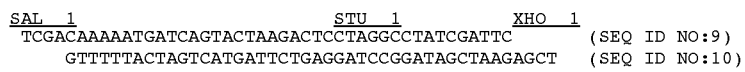

```
SAL 1                    STU 1              XHO 1
  TCGACAAAAATGATCAGTACTAAGACTCCTAGGCCTATCGATTC      (SEQ ID NO:9)
      GTTTTTACTAGTCATGATTCTGAGGATCCGGATAGCTAAGAGCT  (SEQ ID NO:10)
``` resulting in plasmid pGBSCC-6 as shown in FIG. 13.

The StuI-EcoRI fragment from pGBSCC-2 (see Example 1) containing the $P_{450}SCC$ coding region was isolated and the sticky end was filled in, using Klenow DNA polymerase. This fragment was inserted into pGBSCC-6 cut with StuI. The plasmid containing the fragment in the correct orientation was called pGBSCC-7 (see FIG. 14).

(c) Transformation of K.lactis

K.lactis strain CBS 2360 was grown in 100 ml of YEPD-medium (1% yeast extract, 2% peptone, 2% glucose-monohydrate) containing 2.5 ml of 6.7% (w/w) yeast nitro- The SalI-fragment from pGB161 (see J. A. van den Berg et al., European Patent No. 96,430) containing the isocytochrome CI (cyc 1) promoter from S.cerevisiae was isolated and partially digested with XhoI. The 670 bp XhoI-SalI fragment was isolated and cloned into the SalI-site of pGBSCC-8. In the selected plasmid, pGBSCC-9, the SalI-site between the cyc 1 promoter and the 3' noncoding region of the lactase gene was maintained (FIG. 16) (HindIII partially digested).

The SalI-HindIII fragment from pGBSCC-7, containing the $P_{450}SCC$ coding region was inserted in pGBSCC-9 cut with SalI and HindIII. In the resulting plasmid, pGBSCC-10, the $P_{450}SCC$ coding region was downstream to the cyc 1 promoter (FIG. 17).

(b) Transformation of S.cerevisiae

S.cerevisiae strain D273-10B (ATCC 25657) was grown in 100 ml of YEPD overnight at 30° C., subsequently diluted (1:10000) in fresh medium and grown to an $OD_{610}$ of 6. The cells from 10 ml of the culture were collected by centrifugation and suspended in 5 ml of TE-buffer. Again, the cells were collected by centrifugation, suspended in 1 ml of the TE-buffer and 1 ml of 0.2 M lithium acetate was added. The cells were incubated for 1 hour in a shaking waterbath at 30° C. 15 μg of pGBSCC-10 were cut at the unique MluI-site in the cyc 1 promoter, ethanol precipitated and resuspended in 15 μl of TE. This DNA preparation was added to 100 μl of the pre-incubated yeast cells and incubated (shaking) for 30 minutes at 30° C. After addition of 115 μl of a 70% PEG4000 solution, the incubation was prolonged 60 minutes without shaking. Subsequently, a heat shock of 5 minutes at 42° C. was given to the cells and 1 ml of YEPD medium was added, followed by an one and one-half hour incubation at 30° C. in a shaking waterbath. Finally, the cells were collected by centrifugation, resuspended in 30 μl of YEPD and spread on YEPD agar plates containing geneticin (300 μg/ml). Colonies were grown for three days at 30° C.

(c) Analysis of the transformants

Figure 15A:
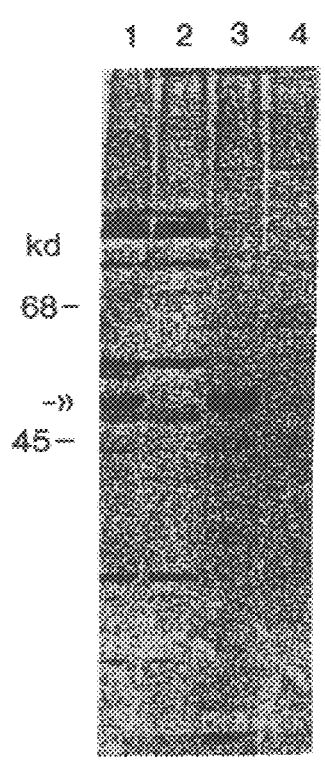

Transformants and the control strain were grown in YEPL-medium (1% yeast extract, 2% bactopeptone, 3.48% $K_2HPO_4$ and 2.2% of a 90% L-(+)-lactic acid solution; before sterilization, the pH was adjusted to 6.0 using a 25% ammonia solution) for 64 hours at 30° C. Further analysis was done as described in Example 5(d). The immunoblot-analysis demonstrated the expression of $P_{450}SCC$ in S.cerevisiae (FIG. 15A, lane 1).

EXAMPLE 7

Construction, transformation and expression of pre-$P_{450}SCC$ encoding DNA in the yeast Kluyveromyces lactis (a) Construction of the expression cassette Plasmid pGB950 (see Example 5(b)) was cut with SalI and XhoI and synthetic DNA was inserted:

pGBSCC-2 was inserted into pGBSCC-11 cut with StuI. The plasmid containing the fragment in the correct orientation was called pGBSCC-12 (FIG. 18).

(b) Transformation of K.lactis and analysis of the transformants

Figure 15B:
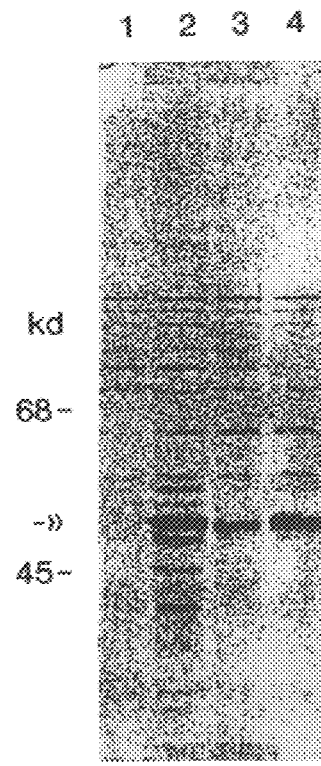
Figure 15C:
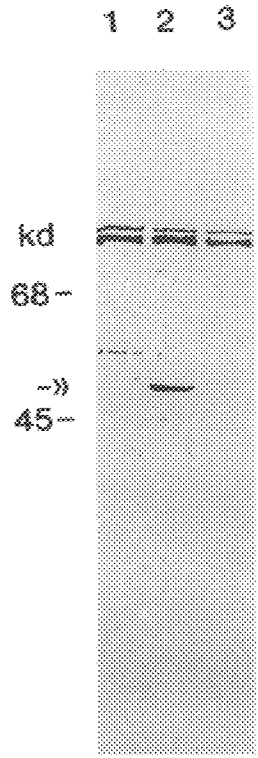

Transformation of K.lactis with pGBSCC-12 was performed as described in Example 5(c). The transformants were analyzed as described in Example 5(d). The analysis demonstrated the production of $P_{450}SCC$ by K.lactis (FIG. 15B, lane 3).

EXAMPLE 8

Construction, transformation and expression of pre-$P_{450}SCC$ encoding DNA in the yeast Saccharomyces cerevisiae (a) Construction of the expression cassette The SalI-HindIII (HindIII partially digested) fragment from pGBSCC-12 containing the pre-$P_{450}SCC$ coding region was inserted in pGBSCC-9 cut with SalI and HindIII. The resulting plasmid was called pGBSCC-13 (FIG. 19).

(b) Transformation of S.cerevisiae and analysis of the transformants

S.cerevisiae strain D273-10B was transformed with pGBSCC-13 as described in Example 6(b). The transformants were analyzed as described in Example 5(c). The result, shown in FIG. 15C (lane 3), demonstrated the expression of $P_{450}SCC$ by S.cerevisiae. One transformant, SCC-105, was further analyzed for in vitro activity of $P_{450}SCC$ (see Example 12).

EXAMPLE 9

Construction, transformation and expression in Kluyveromyces lactis of $P_{450}SCC$ sequences fused to the pre-region of cytochrome oxidase VI from Saccharomyces cerevisiae (a) Construction of the expression cassette Plasmid pGB950 (see Example 6(b)) was cut with SalI and XhoI and synthetic DNA was inserted:

```
SAL I
  TCGACAAAAATGTTGGCTCGAGGTTTGCCATTGAGATCCGCTTTGGTTAAGGCTTGTCC(SEQ ID NO:11)
      GTTTTTACAACCGAGCTCCAAACGGTAACTCTAGGCGAAACCAATTCCGAACAGG(SEQ ID NO:12)

ACCAATCTTGTCCACTGTTGGTGAAGGTTGGGGTCACCACAGAGTTGGTACTGGTGAAGG
TGGTTAGAACAGGTGACAACCACTTCCAACCCCAGTGGTGTCTCAACCATGACCACTTCC

STU 1         XHO 1
TGCTGGTATCAGTACTAAGACTCCTAGGCCTATCGATTC
ACGACCATAGTCATGATTCTGAGGATCCGGATAGCTAAGAGCT
``` resulting in plasmid pGBSCC-11 (FIG. 18). Analogous as described in Example 5(b), the $P_{450}SCC$ coding region of

```
        SAL I
  TCGACAAAAATGTTGTCTCGAGCTATCTTCAGAAACCCAGTTATCAACAGAACTTTGTT(SEQ ID NO:13)
      GTTTTTACAACAGAGCTCGATAGAAGTCTTTGGGTCAATAGTTGTCTTGAAACAA(SEQ ID NO:14)

GAGAGCTAGACCAGGTGCTTACCACGCTACTAGATTGACTAAGAACACTTTCATCCAATC
CTCTCGATCTGGTCCACGAATGGTGCGATGATCTAACTGATTCTTGTGAAAGTAGGTTAG
```

```
                    STU 1            XHO 1
CAGAAAGTACATCAGTACTAAGACTCCTAGGCCTATCGATTC
GTCTTTCATGTAGTCATGATTCTGAGGATCCGGATAGCTAAGAGCT
``` resulting in plasmid pGBSCC-14.

The amino acid sequence from the cytochrome oxidase VI (COX VI) pre-sequence was taken from the article of Wright et al. (J. Biol. Chem., Vol. 259, pp. 15401–15407, 1984). The synthetic DNA was designed, using preferred yeast codons. The $P_{450}SCC$ coding region of pGBSCC-2 was inserted into pGBSCC-14 cut with StuI, similarly as described in Example 5(b). The plasmid containing the $P_{450}SCC$ coding sequence in frame with the COX VI pre-sequence was called pGBSCC-15 (FIG. 20).

(b) Transformation of *K.lactis* and analysis of the transformants

Transformation of *K.lactis* with pGBSCC-15 was performed as described in Example 5(c). The transformants were analyzed as described in Example 5(d). The result (FIG. 15B, lane 2) shows that $P_{450}SCC$ was expressed.

EXAMPLE 10

Construction, transformation and expression in *Saccharomyces cerevisiae* of $P_{450}SCC$ sequences fused to the pre-region of cytochrome oxidase VI from *Saccharomyces cerevisiae*

(a) Construction of the expression cassette

The SalI-HindIII (HindIII partially digested) fragment from pGBSCC-15, containing the coding region for $P_{450}SCC$ fused to the COX VI pre-sequence, was inserted in pGBSCC-9 cut with SalI and HindIII. The resulting plasmid was called pGBSCC-16 (FIG. 21).

(b) Transformation of *S.cerevisiae* and analysis of the transformants

*S.cerevisiae* strain D273-10B was transformed with pGBSCC-16 as described in Example 6(b). The transformants were analyzed as described in Example 6(c). The result, shown in FIG. 15C (lane 2), demonstrated the expression of $P_{450}SCC$ by *S.cerevisiae*.

EXAMPLE 11

In vivo activity of $P_{450}SCC$ in *Bacillus licheniformis* SCC-201

*B.licheniformis* SCC-201 was obtained as described in Example 3 and the organism was inoculated in 100 ml of medium A. Medium A consisted of:

| | |
|---|---|
| Calcium chloride-hexahydrate | 1 g |
| Ammonium sulfate | 5 g |
| Magnesium chloride-hexahydrate | 2.25 g |
| Manganese sulfate-tetrahydrate | 20 mg |
| Cobalt chloride-hexahydrate | 1 mg |
| Citric acid-monohydrate | 1.65 g |
| Distilled water | 600 ml |
| Trace elements stock solution | 1 ml |
| Antifoam (SAG 5693) | 0.5 mg |

Trace elements stock solution contained per 1 of distilled water:

| | |
|---|---|
| $CuSO_4.5H_2O$ | 0.75 g |
| $H_3BO_3$ | 0.60 g |
| KI | 0.30 g |
| $FeSO_2(NH_4)_2SO_4.2H_2O$ | 27 g |
| $ZnSO_4.7H_2O$ | 5 g |
| Citric acid.$H_2O$ | 15 g |
| $MnSO_4.H_2O$ | 0.45 g |
| $Na_2MoO_4.H_2O$ | 0.60 g |
| $H_2SO_4$ (96%) | 3 ml |

After sterilization and cooling to 30° C. to complete the medium, 60 g of maltose-monohydrate dissolved in 200 ml of distilled water (sterilized 20 minutes, 120° C.), 200 ml 1M of potassium phosphate buffer (pH 6.8; sterilized 20 minutes, 120° C.) and 1.7 g of Yeast Nitrogen base (Difco) dissolved in 100 ml of distilled water (sterilized by membrane filtration) were added to the medium. The culture was grown for 64 hours at 37° C. and subsequently 2 ml of this culture were added as inoculum to 100 ml of medium A containing 10 mg of cholesterol. Cholesterol was added as a solution containing cholesterol 10 mg; Tergitol™/ethanol (1:1, v/v), 0.75 ml and Tween 80™, 20 µl. The culture was grown for 48 hours at 37° C., whereupon the culture was extracted with 100 ml of dichloromethane. The mixture was separated by centrifugation and the organic solvent layer was collected. The extraction procedure was repeated twice and the 3×100 ml of dichloromethane fractions were pooled. The dichloromethane was evaporated by vacuum distillation and the dried extract (approximately 450 mg) was analyzed for pregnenolone using a gas chromatograph-mass spectrometer combination.

GC-MS analysis.

From the dried extract, a defined amount was taken and silylated by adding a mixture of pyridine bis-(trimethylsilyl)-trifluoroacetamide and trimethylchlorosilane. The silylated sample was analyzed by a GL-MS-DS combination (Carlo Erba MEGA 5160-Finnigan MAT 311A-Kratos DS 90) in the selected ion mode. Gas chromatography was performed under the following conditions: injection moving needle at 300° C.; column M.cpsil29 0.25 inner diameter of df 0.2 µm operated at 300° C. isotherm; direct introduction into MS-source.

Samples were analyzed by monitoring ions m/z 298 from pregnenolone at a resolution of 800. From the measurements, it was clear that in the case of the host strain *B.licheniformis* T5, no pregnenolone could be detected (detection limit 1 picogram), whereas in the case of *B.licheniformis* SCC-201, production of pregnenolone easily could be monitored.

EXAMPLE 12
In vivo activity of $P_{450}SCC$ from *Saccharomyces cerevisiae* SCC-105

*S.cerevisiae* SCC-105 was obtained as described in Example 8 and the organism was inoculated in 100 ml of medium B. Medium B contained per liter of distilled water:

| Yeast extract | 10 g |
|---|---|
| Bacto Peptone (Oxoid) | 20 g |
| Lactic acid (90%) | 20 g |
| Dipotassium phosphate | 20 g |
| pH = 5.5 (adjusted with ammonia, 25% w/w) | |

This culture was grown for 48 hours at 30° C. and subsequently, this culture was used as inoculum for a fermentor containing medium C. Medium C consisted of:

| Yeast extract | 100 g |
|---|---|
| Bacto Peptone (Oxoid) | 200 g |
| Lactic acid (90%) | 220 ml |
| Dipotassium hydrogen phosphate | 35 g |
| Distilled water | 7800 ml | pH was adjusted at pH = 6.0 with ammonia (25%) and the fermentor including the medium was sterilized (1 hour, 120° C.).

After cooling, 2.4 g of geneticin dissolved in 25 ml of distilled water were sterilized by membrane filtration and added to the medium. The inoculated mixture was grown in the stirred reactor (800 rpm) at 30° C., while sterile air was passed through the broth at a rate of 300 l/h and the pH was automatically kept at 6.0 with 4N $H_2SO_4$ and 5% $NH_4OH$ (5% $NH_4OH$ in distilled water; sterilized by membrane filtration). After 48 hours, a feed of lactic acid (90%, sterilized by membrane filtration) was started at a rate of 20 g/h. The fermentation was then resumed for 40 hours, whereupon the cells were collected by centrifugation (4,000×g, 15 minutes).

The pellet was washed with 0.9% (w/w) NaCl, followed by centrifugation (4000×g, 15 minutes); the pellet washed with phosphate buffer (50 mM, pH=7.0) and cells were collected by centrifugation (4,000×g, 15 minutes). The pellet was taken up in phosphate buffer (50 mM, pH=7.0) resulting in a suspension of 0.5 g wet weight/ml. This suspension was treated in a Dyno®-mill (Willy A. Bachofen Maschinenfabrik, Basel, Schweiz). Unbroken cells were removed by centrifugation (4,000×g, 15 minutes). The cells-free extract (2250 ml, 15–20 mg protein/ml) was stored at −20° C.

$P_{450}SCC$ was roughly purified by the following procedure. From 50 ml of thawed cell-free extract, a rough membrane fraction was pelleted by ultracentrifugation (125,000×g, 30 minutes) and resuspended in 50 ml of a 75 mM potassium phosphate solution (pH 7.0), containing 1% of sodium cholate. This dispersion was gently stirred for 1 hour at 0° C., and subsequently centrifugated (125,000×g, 60 minutes). To the thus obtained supernatant containing solubilized membrane proteins, $(NH_4)_2SO_4$ was added (30% w/v) while the pH was kept at 7.0 by adding small amounts of $NH_4OH$ solution (6N). The suspension was stirred for 20 minutes at 0° C., after which the fraction of precipitated proteins was collected by centrifugation (15,000×g, 10 minutes). The pellet was resuspended in 2.5 ml with 100 mM potassium phosphate buffer (pH 7.0) containing 0.1 mM dithio-threitol and 0.1 mM EDTA. This suspension was eluted over a gel filtration column (PD10, Pharmacia), yielding 3.5 ml of a desalted protein fraction (6 mg/ml), which was assayed for $P_{450}SCC$ activity.

$P_{450}SCC$ activity was determined by an assay which was essentially based on a method of Doering (Methods Enzymology, Vol. 15, pp. 591–596, 1969). The assay mixture consisted of the following solutions:

Solution A (natural $P_{450}SCC$ electron donating system): a 10 mM potassium phosphate buffer (pH 7.0) containing 3 mM of EDTA, 3 mM of phenylmethylsulfonyl fluoride (PMSF), 20 $\mu$M of adrenodoxin and 1 $\mu$M of adrenodoxin reductase (electron carriers; both purified from bovine adrenal cortex), 1 mM of NADPH (electron donor) and 15 mM glucose-6-phosphate and 8 units/ml of glucose-6-phosphate-dehydrogenase (NADPH generating systems).

Solution B (substrate): a micellar solution of 37.5 $\mu$M cholesterol (doubly radiolabeled with [26,27-$^{14}$C] cholesterol (40 Ci/mol) and [7$\alpha$-$^3$H] cholesterol (400 Ci/mol)) in 10% (v/v) Tergitol™ $NP_{40}$/ethanol (1:1, v/v).

The assay was started by mixing 75 $\mu$l of solution A with 50 $\mu$l of solution B and 125 $\mu$l of the roughly purified $P_{450}SCC$ fraction (or buffer as reference). The mixture was stirred gently at 30° C. Samples (50 $\mu$l) were drawn after 0, 30 and 180 minutes and diluted with 100 $\mu$l of water. Methanol (100 $\mu$l) and chloroform (150 $\mu$l) were added to the diluted sample. After extraction and centrifugation (5,000× g, 2 minutes), the chloroform layer was collected and dried. The dry residue was dissolved in 50 $\mu$l of acetone containing 0.5 mg of a steroid mixture (cholesterol, pregnenolone and progesterone (1:1:1, w/w/w)) and subsequently, 110 $\mu$l of concentrated formic acid were added. The suspension was heated for 15 minutes at 120° C. Then, the $^{14}$C/$^3$H ratio was determined by double label liquid scintillation counting. This ratio is a direct measure for the side chain cleavage reaction because the $^{14}$C-labeled side chain was evaporated from the mixture as isocaprylic acid during the heating procedure.

Using this assay, it was found that the $P_{450}$ SCC fraction, roughly purified from *S.cerevisiae* SCC-105, showed side chain cleavage activity. During 3 hours of incubation, 45% of the cholesterol had been converted. By means of thin layer chromatography, the reaction product was identified as pregnenolone.

EXAMPLE 13
Molecular cloning of a full-length cDNA encoding the bovine cytochrome $P_{450}$ steroid 17$\alpha$-hydroxylase ($P_{450}17\alpha$)

Approximately $10^6$ pfu's of the bovine adrenal cortex cDNA library described in Example 1 were selected for $P_{450}17\alpha$cDNA sequences by screening with two $^{32}$P-end labeled synthetic oligomers specific for $P_{450}$cDNA. Oligomer 17$\alpha$-1 (5'-AGT GGC CAC TTT GGG ACG CCC AGA GAA TTC-3') (SEQ ID NO: 15) and oligmer 17$\alpha$-2 (5'-GAG GCT CCT GGG GTA CTT GGC ACC AGA GTG CTT GGT-3') (SEQ ID NO: 16) are complementary to the bovine $P_{450}$SCCcDNA sequences as described by Zuber et al. (J. Biol. Chem., Vol. 261, pp. 2475–2482, 1986) from position 349 to 320 and 139 to 104, respectively.

Selection with oligomer 17$\alpha$-1 revealed ±1500 hybridizing pfu's. Several hybridizing pfu's were selected, purified and scaled up for preparative phage DNA isolation. The EcoRI site inserts of the recombinant lambda-gt11 DNA's were subcloned in the EcoRI site of pTZ18R. One clone, pGB17α-1, was further characterized by restriction endonuclease mapping and DNA-sequencing. Plasmid pGB17α-1 contained an 1.4 kb EcoRI insert complementary to the 3' part of $P_{450}17\alpha$ from the EcoRI site at position 320 to the polyadenylation site at position 1721 as described by Zuber et al. A map of pGB17α-1 is shown in FIG. 22A.

Eight hybridizing pfu's were obtained by selecting the cDNA library with oligomer 17α-2. After purification, upscaling of recombinant phages and isolation of rec lambdagt11 DNA's, EcoRI inserts were subcloned in the EcoRI site of pTZ18R. EcoRI inserts varied in length from 270 bp to 1.5 kbp. Only one clone, pGB17α-2 containing a 345 bp EcoRI-fragment, was further investigated by nucleotide sequencing and compared with the published $P_{450}17\alpha$cDNA sequence data by Zuber et al. As shown in FIG. 22B, the $P_{450}17\alpha$ cDNA sequence in pGB17α-2 started 72 bp upstream the predicted AUG start codon at position 47 and showed complete homology with the 5' part of $P_{450}17\alpha$cDNA till the EcoRI site at position 320 as described by Zuber et al.

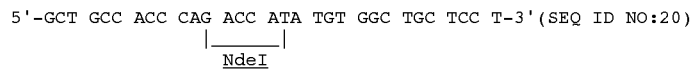

A full-length bovine $P_{450}17\alpha$cDNA was constructed by molecular cloning in *E.coli* JM101 of a ligation mixture containing a partial EcoRI digest of pGB17α-1 and the 345 bp EcoRI fragment of pGB17α-2. The obtained clone pGB17α-3 contained a full-length bovine $P_{450}17\alpha$cDNA and is shown in FIG. 22C.

EXAMPLE 14

Construction and transformation of a full-length $P_{450}17\alpha$cDNA clone into the yeast *Kluyveromyces lactis*

(a) Construction of the expression vector

To derive a suitable expression vector in yeast hosts for bovine $P_{450}17\alpha$, pGB17α-3 was mutated by site-directed mutagenesis as described by Zoller et al, (Methods in Enzymology, Vol. 100, pp. 468–500, 1983); Zoller et al. (Methods in Enzymology, Vol. 154, 329–350, 1987) and Kramer et al. (Methods in Enzymology Vol. 154, pp. 350–367, 1987). Plasmids and strains for in vitro mutagenesis experiments were obtained from Pharmacia Inc.

As indicated in FIG. 23, 9 bp just upstream the ATG initiation codon were changed to obtain a SalI restriction site and optimal yeast translation signals using the synthetic oligomer 17α-3 the pGB950 vector (see Example 5) which was first digested with XhoI, sticky ends filled in with Klenow DNA polymerase and subsequently digested with SalI, resulting in the plasmid pGB17α-5 as depicted in FIG. 24.

(b) Transformation of *K.lactis*

15 μg of pGB17α-5, cut at the unique SacII site in the lactase promoter, was used to transform *K.lactis* strain CBS 2360 as indicated in Example 5. Transformants were analyzed for the presence of integrated pGB17α-5 sequences in the host genome by southern analysis. One transformant, 17α-101 containing at least three copies of pGB17αa-5 in the genomic host DNA, was further analyzed for in vivo activity of $P_{450}17\alpha$ (see Example 16).

EXAMPLE 15

Construction and transformation of $P_{450}17\alpha$ in the bacterial hosts *Bacillus subtilis* and *Bacillus licheniformis*

(a) Construction of the expression vector

To derive a suitable expression vector in Bacillus hosts for bovine $P_{450}17\alpha$, pGB17α-3 was mutated by site-directed mutagenesis as described in Example 14. As indicated in FIG. 25, an NdeI restriction site was introduced at the ATG initiation codon using the synthetic oligomer 17α-4:

```
5'-GCT GCC ACC CAG ACC ATA TGT GGC TGC TCC T-3' (SEQ ID NO:20)
            |_____|
              NdeI
```

The resulting plasmid, pGB17α-6, was partially digested with EcoRI. The DNA fragment containing the full-length $P_{450}17\alpha$cDNA was separated by gel electrophoresis, isolated and ligated to EcoRI digested pBHA-1 DNA as shown in FIG. 26. The ligate was molecular cloned by transferring the ligation mixture into *E.coli* JM101 to obtain pGB17α-7.

(b) Transformation of *B.subtilis* and *B.licheniformis*

The "HpaII" Bacillus promoter was introduced upstream of the $P_{450}17\alpha$cDNA sequences by digestion with pGB17α-6 with the restriction enzyme NdeI, separation of the *E.coli* part of the shuttle plasmid by agarose gel electrophoresis and subsequent religation and transformation of *B.subtilis* 1A40 (BGSC 1A40) competent cells. Neomycin resistant colonies were analyzed and the plasmid pGB17α-8 (FIG. 27) was obtained.

Transformation of the host *B.licheniformis* T5 (CBS 470.83) was also performed with pGB17α-8. The plasmid remained stable in the appropriate Bacillus hosts as revealed by restriction analysis of pGB17α-8, even after many generations.

EXAMPLE 16

In vivo activity of $P_{450}17\alpha$ in *Kluyveromyces lactis* 17α-101

*K.lactis* 17α-101 was obtained as described in Example 14. The organism was inoculated in 100 ml of medium D.

The resulting plasmid, pGB17α-4, was digested with SalI and SmaI and the DNA-fragment containing the full length $P_{450}17\alpha$cDNA was separated by electrophoresis, isolated and transferred by molecular cloning in *E.coli* JM101 into Medium D contained per liter of distilled water:

| Yeast Extract (Difco) | 10 g |
| Bacto Peptone (Oxoid) | 20 g |
| Dextrose | 20 g |

After sterilization and cooling to 30° C., 2.68 g of Yeast Nitrogen Base (Difco) dissolved in 40 ml of distilled water (sterilized by membrane filtration) and 50 mg of neomycin dissolved in 1 ml of distilled water (sterilized by membrane filtration) were added to the medium. Subsequently, 50 mg of progesterone dissolved in 1.5 ml of dimethylformamide were added to 100 ml of medium. The culture was grown for 120 hours at 30° C. and subsequently, 50 ml of culture broth were extracted with 50 ml of dichloromethane. The mixture was centrifugated and the organic solvent layer was separated. Dichloromethane was evaporated by vacuum distillation and the dried extract (about 200 mg) was taken up in 0.5 ml of chloroform. This extract contained 17α-hydroxyprogesterone as shown by thin layer chromatography. The structure of the compound was confirmed by H-MNR and $^{13}$C-NMR. NMR analysis also showed that the ratio of 17α-hydroxyprogesterone/progesterone in the extract was approximately 0.3.

EXAMPLE 17
Molecular cloning of a full-length cDNA encoding the bovine cytochrome $P_{450}$ steroid 21-hydroxylase ($P_{450}$C21)

Approximately $10^6$ pfu's of the bovine adrenal cortex cDNA library, prepared as described in Example 1, were hybridized with a $^{32}$P-end labeled oligo C21-1. This oligo containing the sequence 5'-GAT GAT GCT GCA GGT AAG CAG AGA GAA TTC-3' (SEQ ID NO: 21) was a specific probe for the bovine $P_{450}$C21 gene located downstream the EcoRI site in the $P_{450}$C21 cDNA sequence as described by Yoshioka et al. (J. Biol. Chem., Vol. 261, pp. 4106–4109, 1986). From the screening, one hybridizing pfu was obtained. The EcoRI insert of this recombinant lambda-gt11 DNA was subcloned in the EcoRI site of pTZ18R resulting in a construct called PGBC21-1. As shown in FIG. 28, this plasmid contains a 1.53 kb EcoRI insert complementary to the $P_{450}$C21cDNA sequences from the EcoRI site at position 489 to the polyadenylation site as described by Yoshioka et al., as revealed by nucleotide sequencing.

To isolate the remaining 5' part (490 bp) of the $P_{450}$C21cDNA, a new bovine adrenal cortex cDNA library was prepared with the procedure described in Example 1 with only one modification. As primer for the first cDNA strand synthesis, an additional oligomer C21-2 was added. Oligomer C21-2 with the nucleotide sequence 5'-AAG CAG AGA GAA TTC-3' (SEQ ID NO: 22) was positioned downstream from the EcoRI-site of $P_{450}$C21cDNA from position 504 to 490.

Screening of this cDNA library with a $^{32}$P-end labeled oligomer C21-3 containing the $P_{450}$C21 specific sequence 5'-CTT CCA CCG GCC CGA TAG CAG GTG AGC GCC ACT GAG-3' (SEQ ID NO: 23) (positions 72 to 37) revealed approximately 100 hybridizing pfu's. The EcoRI-insert of only one recombinant lambda-gt11 DNA was subcloned in the EcoRI-site of PTZ18R resulting in a construct called PGBC21-2. This plasmid (FIG. 28) contained an insert of 540 bp complementary to the $P_{450}$C21 cDNA sequences from position −50 to the EcoRI-site at position 489 as revealed by nucleotide sequencing.

EXAMPLE 18
Construction of a $P_{450}$C21cDNA Bacillus expression vector and transformation to the bacterial hosts *Bacillus subtilis* and *Bacillus licheniformis*

(a) Construction of the expression vector

To construct a full-length $P_{450}$C21cDNA with flanking sequences specific for the Bacillus expression vector pBHA-1, the 5' part of the $P_{450}$C21 gene was first modified by the Polymerase Chain Reaction (PCR) method with pGBC21-2 as template and two specific $P_{450}$C21-oligomers as primers. Oligomers C21-4 (5'-CTC ACT GAT ATC CAT ATG GTC CTC GCA GGG CTG CTG-3') (SEQ ID NO: 24) contained 21 nucleotides complementary to C21-sequences from positions 1 to 21 and 18 additional bases to create an EcoRV restriction site and an NdeI restriction site at the ATG initiation codon. Oligomer C21-5 (5'-AGC TCA GAA TTC CTT CTG GAT GGT CAC-3') (SEQ ID NO: 25), was 21 bases complementary to the minus strand upstream the EcoRI-site at position 489.

The PCR was performed as described by Saiki et al (Science, Vol. 239, pp. 487–491, 1988) with minor modifications. The PCR was performed in a volume of 100 µl containing: 50 mM KCl, 10 mM Tris-HCl pH 8.3, 1.5 mM $MgCl_2$, 0.01% (w/v) gelatin, 200 µM each dNTP, 1 µM each C21-primer and 10 ng pGBC21-2 template. After denaturation (7' at 100° C.) and addition to 2 U of Taq-polymerase (Cetus), the reaction mixture was performed to 25 amplification cycles (each: 2' at 55° C., 3' at 72° C., 1' at 94° C.) in a DNA-amplifier apparatus (Perkin-Elmer). In the last cycle, the denaturation step was omitted. A schematic view of this $P_{450}$C21cDNA amplification is shown in FIG. 29.

The amplified fragment was digested with EcoRV and EcoRI and inserted by molecular cloning into the appropriate sites of pSP73 (Promega). The obtained plasmid was called pGBC21-3. As shown in FIG. 30, the 3' $P_{450}$C21-EcoRI fragment of pGBC21-1 was inserted in the right orientation into the EcoRI-site of pGBC21-3. The obtained vector pGBC21-4 was digested with EcoRV and KpnI (KpnI was situated in the multiple cloning site of $pSP_{73}$) and the fragment containing the full-length $P_{450}$C21cDNA was isolated by gel electrophoresis and inserted into the appropriate sites of pBHA-1 by molecular cloning. The derived plasmid pGBC21-5 is illustrated in FIG. 31.

(b) Transformation of Bacillus

The "HpaII" Bacillus promoter was introduced upstream to the $P_{450}$C21cDNA gene by digestion with pGBC21-5 with the restriction enzyme NdeI, separation of the *E.coli* part of the shuttle plasmid by agarose gel electrophoresis and subsequent religation and transformation of *B.subtilis* 1 A40 (BGSC 1 A40) competent cells. Neomycin resistant colonies were analyzed to obtain pGBC21-6 (FIG. 32).

Transformation of the host *B.licheniformis* T5 (CBS 470.83) was also performed with pGBC21-6. The plasmid remained stable in both Bacillus hosts as revealed by restriction analysis.

EXAMPLE 19
Construction of a $P_{450}$C21cDNA yeast expression vector and transformation to the yeast host *Kluyveromyces lactis*

(a) Construction of the expression vector

To derive a suitable expression vector in yeast hosts for bovine $P_{450}$ C21-2, pGBC21-2 was mutated by site directed mutagenesis as described in Example 14. For the mutation, oligomer C21-6 (5=-CCT CTG CCT GGG TCG ACA AAA ATG GTC CTC GCA GGG-3') (SEQ ID NO: 30) was used to create a SalI restriction site and optimal yeast translation signals upstream the ATG initiation codon as indicated in FIG. 33.

The SalI/EcoRI DNA fragment of derived plasmid pGBC21-7 was ligated to the 3' $P_{450}$C21-EcoRI-fragment of pGBC21-1 and inserted by molecular cloning into the appropriate sites of $pSP_{73}$ as indicated in FIG. 34. Derived pGBC21-8 was cut with SalI and EcoRV (EcoRV site was situated in the multiple cloning site of $pSP_{73}$) and the DNA fragment containing the full-length $P_{450}$C21cDNA was inserted into the yeast expression vector PGB950. Derived pGBC21-9 is depicted in FIG. 35.

(b) Transformation of *K.lactis*

15 μg of pGBC21-9 were digested with SacII and transformation of *K.lactis* CBS 2360 was performed as described in Example 5(c).

EXAMPLE 20
Molecular cloning of a full-length cDNA encoding the bovine cytochrome $P_{450}$ steroid 11β-hydroxylase ($P_{450}$11β)

A bovine adrenal cortex cDNA library was prepared as described in Example 1 with one modification. An additional $P_{450}$11β-specific primer (oligomer 11β-1) with the nucleotide sequence 5'-GGC AGT GTG CTG ACA CGA-3' (SEQ ID NO: 32) was added to the reaction mixture of the first strand cDNA synthesis. Oligomer 11β-1 was positioned just downstream to the translation stop codon from position 1530 to 1513. Nucleotide sequences and map positions of mentioned $P_{450}$11β-oligomers were all derived from the $P_{450}$11βcDNA sequence data described by Morohasi et al. (J. Biochem., Vol. 102(3), pp. 559–568, 1987). The cDNA library was screened with a $^{32}$P-labeled oligomer 11β-2 (5'-CCG CAC CCT CGC CTT TGC CCA CAG TGC CAT-3') (SEQ ID NO: 33) located at the 5' end of the $P_{450}$11βcDNA from position 36 to 1.

Screening with oligomer 11β-2 revealed 6 hybridizing pfu's. These were further purified and analyzed with oligomer 11β-3 (5'-CAG CTC AAA GAG AGT CAT CAG CAA GGG GAA GGC TGT-3', positions 990 to 955) (SEQ ID NO: 34). Two out of six showed a positive hybridizing signal with $^{32}$P-labeled oligomer 11β-3. The EcoRI inserts in both lip-lambda-gt11 recombinants were subcloned into the EcoRI-site of pTZ118R. One clone with an EcoRI insert of 2.2 kb (pGB11β-1) was further analyzed by restriction enzyme mapping and is shown in FIG. 36. pGB11β-1 contained all coding $P_{450}$11β cDNA sequences as determined by Morohashi et al.

EXAMPLE 21
Construction of a $P_{450}$C21cDNA Bacillus expression vector and transformation to the bacterial hosts *Bacillus subtilis* and *Bacillus licheniformis*

(a) Construction of the expression vector

A full-length $P_{450}$11β cDNA with modified flanking sequences to the Bacillus expression vector pBHA-1 was obtained by the PCR method (described in Example 18) with pGB11β-1 as template and two specific $P_{450}$11β-oligomers as primers.

Oligomer 11β-4 (5'-TTT GAT ATC GAA TTC CAT ATG GGC ACC AGA GGT GCT GCA GCC-3') (SEQ ID NO: 35) contained 21 bases complementary to the mature $P_{450}$11βcDNA sequence from position 72 to 93 and 21 bases to create EcoRV, EcoRI and NdeI restriction-sites and ATG initiation codon. Oligomer 11β-5 (5'-TAA CGA TAT CCT CGA GGG TAC CTA CTG GAT GGC CCG GAA GGT-3') (SEQ ID NO: 36) contained 21 bases complementary to the minus $P_{450}$11β cDNA strand upstream the translation stop codon at position 1511 and 21 bases to create restriction-sites for EcoRV, XhoI and KpnI.

After PCR amplification with above mentioned template and $P_{450}$11β-primers, the amplified fragment (1.45 kb) was digested with EcoRI and KpnI and inserted by molecular cloning into the Bacillus expression vector pBHA-1 cut with EcoRI and KpnI to obtain the vector pGB11β-2 (see FIG. 36).

(b) Transformation of Bacillus

The "HpaII" Bacillus promoter was introduced upstream to the $P_{450}$11βcDNA sequences by digestion of pGB11β-2 with NdeI, separation of the *E.coli* part of the shuttle plasmid by agarose gel electrophoresis and subsequent religation (as described in Example 18) and transformation of *B.subtilis* 1A40 (BGSC 1A40) competent cells. Neomycin resistant colonies were analyzed and the plasmid, pGB11β-3, was obtained. The derived plasmid pGB11β-3 was also transmitted to the *B.licheniformis* host strain T5 (CBS 470.83).

EXAMPLE 22
Construction of a $P_{450}$11βcDNA yeast expression vector and transformation to the yeast host *Kluyveromyces lactis*

(a) Construction of the expression cassette

A full-length $P_{450}$11β cDNA with modified flanking sequences to the yeast expression vector pGB950 was obtained by the PCR method (described in Example 18) with pGB11β-1 as template and two specific $P_{450}$11β-oligomers as primers.

Oligomer 11β-6 (5'-CTT CAG TCG ACA AAA ATG GGC ACC AGA GGT GCT GCA GCC-3') (SEQ ID NO: 37) contained 21 bases complementary to the mature $P_{450}$11β cDNA sequence from position 72 to 93 and 18 additional bases to create a SalI restriction site, an optimal yeast translation signal and an ATG initiation codon. Oligomer 11β-5 is described in Example 21(a). After PCR amplification with the above mentioned template and $P_{450}$11β-primers, the amplified fragment (1.45 kb), was digested with SalI and XhoI and inserted by molecular cloning into the yeast expression vector pGB950 cut with SalI to obtain the vector pGB11β-4 (FIG. 37).

(b) Transformation of *K.lactis*

15 μg of pGB11β-4 were cut at the unique SacII site in the lactase promoter and transformation of *K.lactis* CBS 2360 was performed as described in Example 5(c).

EXAMPLE 23
Molecular cloning of a full-length cDNA encoding the bovine andrenodoxin (ADX), and subsequent transformation and expression of ADXcDNA in the yeast of *Kluyveromyces lactis*

(a) Molecular cloning of ADX

A full-length ADXcDNA, with 5' and 3' flanking sequences modified to the yeast expression vector pGB950, was directly obtained from a bovine adrenal cortex mRNA/cDNA pool (for detailed description see Example 1) by amplification using the PCR method (see Example 18). For the ADXcDNA amplification, two synthetic oligomer primers were synthesized.

Oligomer ADX-1 (5'-CTT CAG TCG ACA AAA ATG AGC AGC TCA GAA GAT AAA ATA-3') (SEQ ID NO: 43) contained 21 bases complementary to the 5' end of the mature ADXcDNA sequence as described by Okamura et al (Proc. Natl. Acad. Sci. USA, Vol. 82, pp. 5705–5709, 1985) from positions 173 to 194. The oligomer ADX-1 contained at the 5' end 18 additional nucleotides to create a SalI restriction site, an optimal yeast translation signal and an ATG initiation codon. The oligomer ADX-2 (5'-TGT AAG GTA CCC GGG ATC CTT ATT CTA TCT TTG AGG AGT T-3') (SEQ ID NO: 44) was complementary to the 3' end of the minus strand of ADXcDNA from position 561 to 540 and contained additional nucleotides for creating restriction sites for BamHI, SmaI and KpnI.

The PCR was performed as described in Example 18 with 1 $\mu$M of each ADX-primers and 10 $\mu$l of mRNA/cDNA mixture (as described in Example 1) as template. A schematic view of this ADXcDNAa amplification is shown in FIG. 38.

The amplified fragment contained a full-length ADX-cDNA sequence with modified flankings, which was characterized by restriction-site analysis and nucleotide sequencing.

(b) Construction of the expression vector

The amplified ADX cDNA fragment was digested with SalI and SmaI and inserted by molecular cloning into the yeast expression vector pGB950 cut with SalI and EcoRV. The derived plasmid PGBADX-1 is depicted in FIG. 38.

(c) Transformation of K.lactis

15 $\mu$g of pGBADX-1 were cut at the unique SacII-site in the lactase promoter and transformation of K.lactis CBS 2360 was performed as described in Example 5(c).

(d) Analysis of the transformants

Two transformants, ADX-101 and ADX-102, and the control strain CBS 2360 were selected for further analysis. The strains were grown in YEPD-medium for about 64 hours at 30° C. Total cellular protein was isolated as described in Example 5(d). From the supernatants, 8 $\mu$l samples were taken for analysis on immunoblots (see FIG. 39, lanes 3, 4 and 5).

The results show that a protein of the expected length (14 kDa) was expressed in K.lactis cells transformed with pGBADX-1. The in vitro ADX-activity of transformant ADX-102 is described in Example 24.

EXAMPLE 24

In vitro activity of adrenodoxin obtained from Kluyveromyces lactis ADX-102

K.lactis ADX-102, obtained as described in Example 23, and control strain K.lactis CBS 2360 were grown in 100 ml of YEPD medium (1% yeast extract, 2% peptone, 2% glucose monohydrate) containing 2.5 ml of a 6.7% (w/w) yeast nitrogen base (Difco laboratories) solution and 100 mg $l^{-1}$ of geneticin (G418 sulfate; Gibco Ltd.), for 56 hours at 30° C. The cells were collected by centrifugation (4,000×g, 15 minutes), resuspended in a physiological salt solution and washed with a phosphate buffer (pH 7.0, 50 mM). After centrifugation (4,000×g, 15 minutes), the pellet was resuspended in a phosphate buffer (pH 7.0, 50 mM) resulting in a suspension containing 0.5 g cell wet weight/ml. The cells were disrupted using a Braun MSK Homogenizer (6×15 seconds, 0.45–0.50 mm glass beads) and unbroken cells were removed by centrifugation (4,000×g, 15 minutes). The cell-free extracts (40 mg protein/ml) were stored at –20° C.

ADX activity, i.e. electrotransfer capacity from adrenodoxin reductase to cytochrome $P_{450}SCC$, in the cell-free extracts was determined by a $P_{450}SCC$ activity assay. The assay mixture consisted of the following solutions:

Solution A (natural $P_{450}SCC$ electron donating system with the exception of ADX): a 50 mM potassium phosphate buffer (pH 7.0) containing 3 mM of EDTA, 2 $\mu$M of adrenodoxin reductase (purified from bovine adrenal cortex), 1 mM of NADPH (electron donor), 15 mM glucose-6-phosphate and 16 units/ml of glucose-6-phosphate-dehydrogenase (NADPH regenerating system).

Solution B (substrate and enzyme): a micellar solution of 75 $\mu$M of cholesterol (doubly radiolabeled with [26,27-$^{14}$C] cholesterol (40 Ci/mol) and [7$\alpha$-$^{3}$H] cholesterol (400 Ci/mol)) and 1.5 $\mu$M of $P_{450}$ SCC (purified from bovine adrenal cortex) in 10% (v/v) Tergitol™ NP 40/ethanol (1:1, v/v).

The assay was started by mixing 75 $\mu$l of solution A with 50 $\mu$l of solution B and 125 $\mu$l of cell-free extract or 125 $\mu$l of a potassium phosphate buffer (50 mM, pH 7.0) containing 10 $\mu$M ADX (purified from bovine adrenal cortex). The mixture was stirred gently at 30° C. Samples were drawn after 15 minutes of incubation and diluted with 100 $\mu$l of water. From a sample, substrate and product(s) were extracted with 100 $\mu$l of methanol and 150 $\mu$l of chloroform. After centrifugation (5,000×g, 2 minutes), the chloroform layer was collected and dried. The dry residue was dissolved in 50 $\mu$l of acetone containing 0.5 mg of a steroid mixture (cholesterol, pregnenolone and progesterone (1:1:1, w/w/w)) and subsequently 110 $\mu$l of concentrated formic acid were added. The suspension was heated for 15 minutes at 120° C. and then, the $^{14}$C/$^{3}$H ratio was determined by double label liquid scintillation counting. The ratio was a direct measure for the side chain cleavage reaction, because the $^{14}$C-labeled side chain was evaporated from the mixture as isocaprylic acid during the heating procedure.

Using this assay, ADX electron carrier activity could easily be demonstrated in the cell-free extract of K.lactis ADX-102. In the assays with cell-free extract of K.lactis ADX-102 or with purified ADX, the side chain of the cholesterol was cleaved within 15 minutes in a yield of 50%, whereas in the assay with cell-free extract of the control K.lactis CBS 2360, no side chain cleavage could be detected.

EXAMPLE 25

Molecular cloning and construction of a full-length cDNA encoding the bovine adrenodoxin oxidoreductase (ADR), and subsequent transformation of ADRcDNA in the yeast Kluyveromyces lactis (a) Molecular cloning of adrenodoxin oxidoreductase A bovine adrenal cortex cDNA library was prepared as described in Example 1 with one modification. An additional ADR-specific primer (oligomer ADR-1) with the nucleotide sequence 5'-GGC TGG GAT CTA GGC-3' (SEQ ID NO: 49) was added to the reaction mixture of the first strand cDNA synthesis. Oligomer ADR-1 was located just downstream to the translation stop codon from position 1494 to 1480.

Nucleotide sequences and map positions of mentioned ADR-oligomers were all derived from the ADRcDNA sequence data described by Nonaka et al, Biochem. Biophys. Res. Comm., Vol. 145(3), pp. 1239–1247, 1987). The obtained cDNA library was screened with a $^{32}$P-labeled oligomer ADR-2 (5'-CAC CAC ACA GAT CTC GGG CCT CTG CTC CTG TGG CCA-3') (SEQ ID NO: 50).

4 hybridizing pfu's were identified and subsequently purified. However, only 1 pfu showed also a positive signal with oligomer ADR-3 (5'-TTC CAT CAG CCG CTT CCT CGG GCG AGC GGC CTC CCT-3') (SEQ ID NO: 51), which was located in the middle of the ADRcDNA (position 840 to 805). The ADRcDNA insert (approx. 2 kb) was molecular cloned into the EcoRI-site of pTZ18R. The obtained plasmid, pGBADR-1, contained a full-length ADRcDNA as revealed by restriction enzyme mapping and nucleotide sequencing. The physical map of pGBADR-1 is illustrated in FIG. 40.

(b) Construction of the expression cassette

A full-length ADR cDNA with modified flanking sequences to the yeast expression vector, pGB950, was obtained by the PCR method (see Example 18) with pGBADR-1 as template and two'specific ADR-oligomers as primers. Oligomer ADR-4 ((5-CGA GTG TCG ACA AAA ATG TCC ACA CAG GAG CAG ACC-3') (SEQ ID NO: 52), contained 18 bases complementary to the mature ADRcDNA sequences from position 96 to 114 and 18 bases to introduce a SalI restriction site, an optimal yeast translation signal, and an ATG initiation codon.

Oligomer ADR-5 (5'-CGT GCT CGA GGT ACC TCA GTG CCC CAG CAG CCG CAG-3') (SEQ ID NO: 53) contained 18 bases complementary to the minus strand of ADRcDNA upstream to the translation stop codon at position 1479 and 15 bases to create KDnI and XhoI restriction sites for molecular cloning in various expression vectors.

After amplification with the above mentioned template and ADR primers, the amplified fragment (1.4 kb) was digested with SalI and XhoI and inserted by molecular cloning into the yeast expression vector pGB950 cut with SalI and XhoI. The derived plasmid, pGBADR-2, is illustrated in FIG. 40.

(c) Transformation of *K.lactis*

15 μg of pGBADR-2 was cut at the unique SacII-site in the lactase promoter and transformation of *K.lactis* CBS 2360 was performed as described in Example 5(c).

EXAMPLE 26
Molecular cloning of a full-length cDNA encoding bovine NADPH-cytochrome $P_{450}$ reductase (RED)

The bovine adrenal cortex cDNA library described in Example 1 was screened with a $^{32}$P-labeled synthetic oligomer 5'-TGC CAG TTC GTA GAG CAC ATT GGT GCG TGG CGG GTT AGT GAT GTC CAG GT-3' (SEQ ID NO: 54), specific for a conserved amino acid region within rat-, porcine- and rabbit RED as described by Katagari et al (J. Biochem., Vol. 100, pp. 945–954, 1986) and Murakami et al. (DNA, Vol. 5, pp. 1–10, 1986).

Five hybridizing pfu's were obtained and further characterized by restriction enzyme mapping and nucleotide sequencing. A full-length REDcDNA was inserted into expression vectors and transformed to appropriate hosts as mentioned in Examples 2, 3 and 6.

EXAMPLE 27
Construction, transformation and expression of an expression cassette encoding the proteins $P_{450}$SCC and ADX in the yeast *Kluyveromyces lactis*

(a) Construction of the expression cassette

The expression cassette pGBADX-1 (see Example 23) was digested with SacII and HindIII (partially) and sticky ends were filled in using Klenow DNA polymerase. The DNA fragment comprising a part of the lactase promoter (but still functional), the coding ADX sequence and the lactase terminator was separated and isolated by agarose-gel electrophoresis and subsequently inserted into pGBSCC-7, which was first linearized by XbaI digestion (see Example 5(b)) and sticky ends filled in using Klenow DNA polymerase. The construction was set up so that a unique restriction site (SacII) was obtained, which is necessary to transfer the plasmid to *K.lactis*.

This unique SacII restriction site was located in the lactase promoter sequence flanking the SCC sequence, as the SacII restriction site in the lactase promoter flanking the ADX sequence was destroyed by the fill-in reaction. The obtained expression cassette pGBSCC/ADX-1 contained the coding sequence for SCC as well as for ADX, each driven by the lactase promoter.

(b) Transformation of *K.lactis*

Transformation of *K.lactis* CBS 2360 was performed as described in Example 5(c) with 15 μg of pGBSCC/ADX-1, linearized at the unique SacII restriction site. One transformant (SCC/ADX-101) was selected from SCC and ADX expression studies.

(c) Analysis of the transformant *K.lactis* SCC/ADX-101

Cellular protein fractions were prepared from cultures of the SCC/ADX-101 and the control strain CBS 2360 as described in Example 5(d) and analyzed by SDS/PAGE and Western-blotting. The blot was probed with antibodies specific for SCC and ADX, respectively. Compared to the control strain, the cellular protein fraction of transformant SCC/ADX-101 showed two additional bands of expected length (53 and 14 kDa, respectively) showing the expression of both proteins SCC and ADX. Expression levels of both in transformant SCC/ADX-101 were comparable with levels observed in transformants expressing only one protein (for SCC see FIG. 15A, lane 3, and for ADX FIG. 39, lane 5). The in vitro SCC and ADX activity of transformant SCC/ADX-101 is described in Example 28.

EXAMPLE 28
In vitro activity of $P_{450}$SCC and adrenodoxin obtained from *Kluyveromyces lactis* SCC/ADX-101

*K.lactis* SCC/ADX-101 obtained as described in Example 27 and control strain *K.lactis* SCC-101 as described in Example 5(d) were grown in 1 liter of YEPD medium (1% yeast extract, 2% peptone, 2% glucose monohydrate) containing 100 mg l$^{-1}$ of geneticin (G418 sulfate; Gibco Ltd.), for 72 hours at 30° C. The cells were collected by centrifugation (4,000×g, 15 minutes), resuspended in a physiological salt solution and washed with a phosphate buffer (pH 7.5, 75 mM). After centrifugation (4,000×g, 15 minutes), the pellet was resuspended in a phosphate buffer (pH 7.5, 75 mM) resulting in a suspension containing 0.5 g cell wet weight/ml. The cells were disrupted using a Braun MSK Homogenizer (6×15 seconds, 0.45–0.50 mm glass beads). Unbroken cells were removed by centrifugation (4,000×g, 15 minutes).

In the cell-free extracts, the activity of the protein complex $P_{450}SCC/ADX$ was assayed by determining the cholesterol side-chain cleaving reaction in the presence of NADPH and ADR. The assay mixture consisted of the following solutions:

Solution A (natural $P_{450}SCC$ electron donating system with the exception of ADX): a 50 mM potassium phosphate buffer (pH 7.0) containing 3 mM of EDTA, 2 µM of adrenodoxin reductase (purified from bovine adrenal cortex), 1 mM of NADPH (electron donor), 15 mM of glucose-6-phosphate and 16 units/ml of glucose-6-phosphate-dehydrogenase (NADPH regenerating system).

Solution B (substrate and enzyme): a micellar solution of 37.5 µM of cholesterol (doubly radiolabeled with [26,27-$^{14}$c] cholesterol (40 Ci/mol) and [7α-$^{3}$H] cholesterol (400 Ci/mol)) in 10% (v/v) Tergitol™ NP 40/ethanol (1:1, v/v).

The assay was started by mixing 75 µl of solution A with 50 µl of solution B and 125 µl of cell-free extract. The mixture was stirred gently at 30° C. Samples were drawn after 60 minutes of incubation and diluted with 100 µl of water. From a sample, substrate and products(s) were extracted with 100 µl of methanol and 150 µl of chloroform. After centrifugation (5,000×g, 2 minutes), the chloroform layer was collected and dried. The dry residue was dissolved in 50 µl of acetone containing 0.5 mg of a steroid mixture (cholesterol, pregnenolone and progesterone (1:1:1, w/w/w)) and subsequently 110 µl of concentrated formic acid were added. The suspension was heated for 15 minutes at 120° C. Then, the $^{14}$C/$^{3}$H ratio was determined by double label liquid scintillation counting. The ratio was a direct measure for the side-chain cleavage reaction, because the $^{14}$C-labeled side chain was evaporated from the mixture as isocaprylic acid during the heating procedure.

Using this assay, cholesterol side-chain cleaving activity was demonstrated in the cell-free extract of K.lactis SCC/ADX-101, whereas the cell-free extract of K.lactis SCC-101, no activity was detectable. By means of HPLC-analysis, the reaction product produced by a cell-free extract of K.lactis SCC/ADX-101 was identified as pregnenolone.

EXAMPLE 29

Construction and transformation of an expression cassette encoding bovine cytochrome $P_{450}$ steroid 17α-hydroxylase and bovine cytochrome $P_{450}$ steroid C21-hydroxylase in the yeast Kluyveromyces lactis (a) Construction of the expression cassette The expression cassette pGB17α-5 (FIG. 41) described in Example 14, was digested with SacII and HindIII (partially) and sticky ends were filled in using Klenow DNA polymerase. The DNA fragment comprising a part of the lactase promoter, the sequence coding for $P_{450}17α$ and the lactase terminator were separated and isolated by agarose gel electrophoresis and subsequently inserted into pGBC21-9 (FIG. 42) described in Example 19, which was first linearized by XbaI digestion and sticky ends filled in using Klenow, DNA polymerase. The obtained expression cassette, pGB17α/C21-1 (FIG. 43), had a unique SacII restriction site because the SacII, restriction site in the lactase promotor flanking the $P_{450}17α$ sequence was destroyed by the fill-in reaction.

(b) Transformation of K.lactis

Transformation of K.lactis CBS 2360 was performed as described in Example 5(c) with 15 µg of pGB17α/C21-1, linearized at the unique SacII restriction site. One transformant 17α/C21-101 was further analyzed for in vivo activity of both, $P_{450}17α$ and $P_{450}C21$ (see Examples 30 and 31).

EXAMPLE 30

In vitro activity of $P_{450}17α$ and $P_{450}C21$ obtained from Kluyveromyces lactis 17α/C21-101

K.lactis 17α/C21-101 obtained as described in Example 29, K.lactis 17α-101 as described in Example 14 and K.lactis CBS 2360 were grown in 100 ml of medium D. Medium D contained per liter of distilled water:

| | |
|---|---|
| Yeast Extract (Difco) | 10 g |
| Bacto Peptone (Oxoid) | 20 g |
| Dextrose | 20 g |
| pH = 6.5 | |

After sterilization and cooling to 30° C., 25 mg of geneticin (G418 sulfate; Gibco Ltd.) dissolved in 1 ml of distilled water sterilized by membrane filtration was added. The cultures were grown for 72 hours at 30° C. and the cells were collected by centrifugation (4,000×g, 15 minutes). The pellet was washed with phosphate buffer (50 mM, pH=7.0) and cells were collected by centrifugation (4,000×g, 15 minutes). The pellet was taken up in phosphate buffer (50 mM, pH=7.0) resulting in a suspension containing 0.5 g wet weight/ml. This suspension was disrupted by sonification (Braun labsonic 1510; 12×1 minute, 50 Watts) Unbroken cells were removed by centrifugation (12,000×g, 15 minutes).

Cell-free extracts were assayed for $P_{450}17α$ activity and $P_{450}C21$ activity by determining the production of 17α,21 dihydroxy-progesterone in the presence of NADPH. The assay mixture consisted of the following solutions:

Solution A: a 50 mM potassium phosphate buffer (pH=7.0), containing 3 mM of EDTA, 2 mM of NADPH, 50 mM of glucose-6-phosphate and 16 units/ml of glucose-6-phosphate-dehydrogenase (NADPH-regenerating system).

Solution B (substrate): a micellar solution of 80 µM of [4-$^{14}$C] progesterone (30 Ci/mol) in 10% (v/v) Tergitol™ NP 40/ethanol (1:1, v/v) in a potassium phosphate buffer (75 mM, pH=7,5).

The assay was started by mixing 75 µl of Solution A with 50 µl of Solution B and 125 µl of cell-free extract. The mixture was stirred gently at 30° C. and 50 µl samples were drawn after 60 minutes of incubation and added to a mixture of 100 µl of methanol and 50 µl of chloroform. Subsequently, 100 µl of chloroform and 100 µl of water were added. The chloroform layer was collected by centrifugation (5,000×g, 2 minutes) and the water/methanol layer was re-extracted with 100 µl of chloroform. The two chloroform layers were combined and dried. The dry residue was dissolved in 100 µl of acetonitrile/H$_2$O (9:1, v/v) and 50 µl samples were eluted with acetonitrile/H$_2$O (58:42, v/v) using an HPLC column (Chrompack lichr. 10RP18, 250×4.6 mm). In the eluate, the steroid substrate and products were detected by a flow scintillation counter and a U.V. detector. The radioactivity of the collected fractions was determined by liquid scintillation counting. Using the assay, it was found that a cell-free extract obtained from K.lactis 17α/C21-101 produced 17α,21 dihydroxy progesterone, whereas cell-free extracts obtained from K.lactis 17α-101 and K.lac-

*tis* CBS 2360 did not. The main product produced by *K.lactis* 17α-101 appeared to be 17α hydroxy progesterone.

EXAMPLE 31
In vivo activity of $P_{450}17\alpha$ and $P_{450}C21$ in *Kluyveromyces lactis* 17α/C21-101

*K.lactis* 17α/C21-101 obtained as described in Example 29 and *K.lactis* CBS 2360 were inoculated in 25 ml of medium D. Medium D contained per liter of distilled water:

| | |
|---|---|
| Yeast Extract (Difco) | 10 g |
| Bacto Peptone (Oxoid) | 20 g |
| Dextrose | 20 g |
| pH = 6.5 | |

After sterilization and cooling to 30° C., 25 mg of geneticin dissolved in 1 ml of distilled water sterilized by membrane-filtration was added to 1 liter of medium D. Then, 100 µl of a solution containing the substrate [4-$^{14}$C] progesterone were added to 25 ml of the completed medium. The substrate solution contained 800 µl [4-$^{14}$C] progesterone (8 Ci/mole) per ml in 10% (v/v) Tergitol™ NP 40/ethanol (1:1, v/v). The cultures were grown at 30° C. in a rotary shaker (240 rpm) and samples of 2 ml taken after 0 and 68 hours were drawn. Each sample was mixed with 2 ml of methanol. After 24 hours of extraction at 4° C., the mixtures were centrifugated (4,000×g, 15 minutes). From the obtained supernatant, samples of 200 µl were eluted with acetonitrile/H$_2$O (58:42, v/v) using an HPLC column (Chrompack Lichr. 10 RP18, 250×4.6 mm).

In the eluate, the steroid substrate and products were detected. The radioactivity of the collected fractions was determined by liquid scintillation counting. One of the fractions obtained from a culture of *K.lactis* 17α/C21-101 grown for 68 hours clearly showed the presence of 17α,21 dihydroxyprogesterone, whereas this compound was not produced in a culture of the control strain *K.lactis* CBS2360.

EXAMPLE 32
Construction, transformation and expression of an expression cassette encoding the human 3β-HSDH in the yeast *Saccharomyces cerevisiae*

1. Generation of pUC derivatives with new polylinker sites.

M13mp19 (Yanisch-Peron, C. et al., Gene 33 (1985) p 103–119) was mutagenized using oligonucleotide

OTG2805: 5' GCGCTCAGCGGCCGCTTTCCAGTCG 3' (SEQ ID NO: 59)

and a NotI site was introduced into the remaining sequence of the lacI gene (M13TG724). Then, a polylinker containing EcoRI, SnaBI and NotI sites was introduced in the EcoRI site of M13TG724 using oligonucleotides

OTG2793: 5' AATTGCGGCCGCGTACGTATG 3' (SEQ ID NO: 60)

and

OTG2796: 5' AATTCATACGTACGCGGCCGC 3' (SEQ ID NO: 61)

However, during the cloning step, multiplication and modification of the insert occurred. The resulting M13TG7244 had the following sequence:

<u>GAATTC</u>A<u>TACGTA</u>CG<u>CGGCCGC</u>AATTGCGGCCGG
<u>TACGTA</u>TAATTCACTGGCCGT (SEQ ID NO: 62)

Note that the EcoRI, SnaBI and NotI sites are underlined and that the lacZ sequence of pUC19 is in italics. M13TG7244 was digested with EcoRI and SstI restriction enzymes and a linker was introduced using oligonucleotides OTG2919: 5' CAACGCGTCCTAGG 3' (SEQ ID NO: 63) and

OTG2920: 5' AATTCCTAGGACGCGTTGAGCT 3' (SEQ ID NO: 64)

yielding M13TG7246. This linker added MluI and AvrII sites. A PvuII fragment containing the relevant restriction sites of M13TG7246 was subcloned into pUC19, yielding pTG7457 (FIG. 44).

pUC19 (Yanisch-Peron, C. et al., Gene 33 (1985) p 103–119) was digested with BamHI and EcoRI restriction enzymes and a polylinker was introduced using oligonucleotides

OTG2792: 5' GATCCGCAGATATCATCTAGATCCCGGGTAGAT 3', (SEQ ID NO: 65)

OTG2797: 5' AGAGCTCAAGATCTACCCGGGATCTA-GATGATATCTGCG 3', (SEQ ID NO: 66)

OTG2794: 5' CTTGAGCTCTACGCAGCTGGTCGACAC-CTAGGAG 3' (SEQ ID NO: 67) and

OTG2795: 5' AATTCTCCTAGGTGTCGACCAGCTGCGT 3' (SEQ ID NO: 68)

yielding pTG7453 (FIG. 45).

Subcloning of the terminator.

PGK terminator:

The polylinker sites between BamHI and SstI of pTG7453 were introduced into a pTG7457 derivative and the new plasmid was digested with BglII and HindIII restriction enzymes and a similarly restricted fragment containing the PGK terminator (Hitzeman, R. A. et al., Nucleic Acids Res. 10 (1982) 7791–7808) ; Loison, G. et al., Yeast 5 (1989) p 497–507) was cloned into it. The new plasmid was termed pTG10014 (FIG. 46). pTG10014 was digested with ClaI restriction enzyme and the cohesive ends filled in with the Klenow polymerase yielding pTG10015.

Subcloning of the promoters.

a) the CYC1 promoter:

The polylinker sites between BamHI and SstI of pTG7453 were introduced into a pTG7457 derivative and the new plasmid was opened by SnaBI restriction enzyme and the RsaI DraI fragment of 456 nucleotides of pEMBL8 (Dente et al., Nucleic Acids Res. 11 (1983) p 1645–1655), containing the origin of replication of phage f1, was introduced generating pTG7503. A 0.78 kb BamHI HindIII fragment of pGBSCC-9, prepared in Example 6 containing the CYC1 promoter of *Saccharomyces cerevisiae*, a polylinker and the lactase terminator of *Kluyveromyces lactis*, were subcloned in pTG7503, yielding pTG10004 (FIG. 47). The XhoI and MluI sites of the CYC1 promoter were eliminated by site directed mutagenesis using oligonucleotide

OTG4410: 5' GCGGATCTGCTCGAAGATTGCCT-
GCGCGTTGGGCTTGATC 3' (SEQ ID NO: 69)

on ssDNA of pTG10004. This yielded pTG10005. pTG10005 was digested with SalI and XhoI restriction enzymes and a MluI site was introduced using oligonucleotides OTG4433: 5' TCGACGGACGCGTGG 3' (SEQ ID NO: 70) and

OTG4434: 5' TCGACCACGCGTCC 3' (SEQ ID NO: 71)

yielding pTG10006.

b) The GAL10/CYC1 promoter:

The pYeDP1/8-2 (Cullin, C., Gene 65 (1988) p 203–217) plasmid was opened with XhoI restriction enzyme. The cohesive ends were filled in with klenow polymerase and the plasmid was religated. In pTG10010, the GAL10/CYC1 promoter no longer contained the XhoI site and this served as a template for a PCR amplification.

2. Construction of the expression vectors.

In pTG7503, part of the remaining lacZ coding sequence was eliminated by site directed mutagenesis using oligonucleotide

OTG4431: 5' TGGCCGTCGTTTTACTCCTGCGCCTGAT-
GCGGTAT 3' (SEQ ID NO: 72)

yielding pTG7549. The LacZ promoter present in pTG7549 was deleted using oligonucleotides OTG4470: 5' GGCCGCAAAACCAAA 3' (SEQ ID NO: 73) and

OTG4471: 5' AGCTTTTGGTTTTGC 3' (SEQ ID NO: 74)

which were inserted after a NotI HindIII restriction, restoring both sites. The new construct was termed pTG7553. A BamHI MluI fragment containing the CYC1 promoter of pTG10006 and the MluI HindIII fragment containing the PGK terminator of pTG10015 were ligated together. The ligation material was then added to pTG7553, previously digested with MluI and HindIII restriction enzymes. Finally, oligonucleotide

OTG4478: 5' GATCTATCGATGCGGCCGCG 3' (SEQ ID NO: 75)

hybridized with oligonucleotide

OTG4479: 5' CGCGCGCGGCCGCATCGATA 3' (SEQ ID NO: 76)

(BamHI MluI linkers containing ClaI NotI sites) was added, and ligated together. The resulting plasmid was termed pTG10031 (FIGS. 48). The PCR amplified fragment obtained with pYeDP1/8-2 was digested with ClaI and SalI restriction enzymes and introduced into pTG10031 digested with the same enzymes yielding pTG10033 (FIG. 49).

3. Construction of the basic vector pTG3828 (Achstetter, T. et al., Gene 110 (1992) p 25–31) was digested with BglII and BamHI restriction enzymes and a polylinker segment of pPOLYIII (Lathe R. et al., Gene 57 (1987) p 193–201) covering the BglII BamHI sites was introduced. The orientation which had lost the BglII and BamHI sites was chosen (pTG10012). pTG10012 was digested with NotI and EcoRI restriction enzymes and ligated to the large EcoRI NotI fragment of pTG7549 and this generated pTG10013 (FIG. 50). The URA3-D fragment on this plasmid was bordered by HindIII sites.

4. Construction of the recombination vectors.

The NotI cassettes containing the CYC1 or the GAL10/CYC1 promoter and the PGK terminator were subcloned into vectors containing the URA3-d gene in both orientations, yielding, recombination vectors pTG10041-pTG10042 and pTG10045-pTG10046 respectively. pTG10013 was digested with NotI restriction enzyme and the NotI fragments containing the expression block of pTG10031 were ligated into it yielding two orientations, pTG10041 (FIG. 51) and pTG10042 (FIG. 52). Similarly, pTG10045 (FIG. 53) and pTG10046 (FIG. 54) were obtained from pTG10033 and pTG10013.

5. Construction of transfer vectors

The cDNA coding for human 3BHSDH Type I, obtained from Labrie, was contained in the EcoRI site of pT7T3 vector. The coding sequence corresponded to the sequence published previously by V. Luu The et al. (1989) Mol. Endocrinol. Vol. 3, pp. 1310–1312, except that the 5' contained an additional GGG. This plasmid was modified to allow direct cloning in the expression vectors. First, a linker containing a MluI site using oligonucleotide

OTG4539 : 5' AATTGGACGCGTCC 3' (SEQ ID NO: 77)

was introduced at the 3' end of the coding sequence after partial EcoRI digestion (pTG10036). The EcoRI site of pTG10036 was treated by Mung Bean Nuclease and the resultant DNA was digested by MluI restriction enzyme. On the other hand, a SalI MluI insert of 1.7 kb was cloned into the SalI MluI sites of pTG10031 (pTG10058). The SalI site of pTG10058 which carried the CYC1 promoter was filled in with Klenow polymerase and the resultant plasmid was digested with MluI restriction enzyme. Ligation of these fragments yielded pTG10064 (FIG. 55) which contained the coding sequence for 3BHSDH bordered by SalI and MluI restriction sites. The SalI MluI fragment from pTG10064 was subcloned into pTG10033 yielding pTG10065 (FIG. 56) with 3BHSDH under control of GAL10/CYC1.

6. Expression of 3BHSDH in S. cerevisiae

The yeast used in this study was strain W303-1B (MATα, $\rho^+$, ura3-1, leu2-3, -112, his3-11, -15, trp1-1, ade2-1, can$^R$(?), cyr$^+$(?) [Crivellone et al., J. Biol. Chem. 263 (1988) 14323–14333) as a model strain. W303-1B was auxotrophic for uracil, leucine, histidine, tryptophane, adenine and resistant to canavanine.

a) Construction of a yeast—E.coli shuttle vector for the expression of 3BHSDH.

Using the recombination vectors, assembly of the desired expression plasmid via recombination in vivo can be accomplished. Yeast was made electrocompetent and was transformed using 100 ng of pTG10042 (restricted with SalI and MluI) and pTG10065 (restricted with NotI). After electroporation, the cells were plated on selective YNBG medium containing adenine, tryptophane, leucine and histidine but no uracil. After 3–4 days of growth, colonies were purified on the same medium. Saccharomyces cerevisiae recombined expression plasmid (SCREP) pTG10201 (PromCYC1-3β HSDH—PGKterm) was obtained in strain (W303-1B). The latter SCREP was obtained by an in vivo recombination between the GAL10/CYC1 promoter and the CYC1 promoter, reconstructing the CYC1 promoter.

b) Detection of 3B HSDH antigen in yeast by Western blotting.

Antibodies

The rabbit anti-3B HSDH antibodies against human 3BHSDH were obtained from F. Labrie and have been described in V. Luu The et al., (1989) Mol. Endocrinol. Vol. 3, pp. 1310–1312.

Western blotting

Western blotting was done as described previously (E. Degryse et al., (1992) Gene Vol. 118, pp. 47–53) except that anti-3βHSDH antibodies were used.

c) Compartmentation.

Compartmentation was studied in strain W303-1B transformed with SCREP pTG10201 (CYC1+3β HSDH). Cells were divided into cytosol, mitochondria and microsomes according to C. Cullin and al., Gene 65 (1988) p 203–217. Western blots and activity measurements were performed on fractions of the untransformed and two transformed strains. The control (untransformed strain) was found to be negative all over. For the other strains, most of the activity was found in the mitochondrial and microsomal fractions. These results were confirmed in the Western blot, showing the correct size of the expressed gene product.

d) In vitro activity of 3β HSDH after induction in minimal medium and cell fractionation.

Cells were grown until an optical density between 2 and 5 at 600 nm, in YNBG medium supplemented with casamino acids (0.5%) and tryptophane, adenine, histidine and leucine. After harvest of the cells by centrifugation, microsomes were prepared according to C. Cullin and al., Gene 65 (1988) p 203–217. The 3β HSDH activity was measured with the method of Bauer H. C. et al., J. Steroid Biochem. 33 (1989) 643–646. The microsomes were taken up in TrisHCl 50 mM pH7.4, EDTA 2 mM, glycerol 20% and stored at −20° C. until used. The protein concentration was 3.75 mg/ml. Activity was measured in DPBS +BSA (0.175 ml)+pregnenolone (0.005 ml; 1 μCi=40 nmole/ml) and 19 μg of microsomal extract/tube. The reaction was started by the addition of NAD 10 mM (0.015 μl) and lasted for 60 minutes at 37° C. Controls were used in which the reaction was stopped immediately after substrate addition to the complete reaction mixture (t=0h) or to the NAD deleted reaction mixture (t=0h-NAD).

The in vitro activity of 3β HSDH was measured using radioactive pregnenolone. After incubation at 37° C., the bulk of the pregnenolone was precipitated with digitonin and the soluble product (progesterone) was measured by scintillation counting. A microsomal fraction of W303-1B/ pTG10201 (CYC1+3β HSDH) was shown to be active in the presence of NAD only.

| NAD dependence of 3β HSDH activity | | |
|---|---|---|
| | t = 0h − (t = 0H − NAD) | 60′ − (t = 0h − NAD) |
| + NAD | 17000 | 463000 |
| − NAD | 0 | 0 |

Activity was also measured after cell fractionation (see above). Activity was measured in DPBS+BSA (0.077 ml)+ pregnenolone (0.002 ml; 1 μCi=40 nmole/ml)+NAD (0.010 μl, 10 mM) and 7 μg of cytosolic extract, 9 μg of mitochondrial extract and 6 μg of microsomal extract/tube.

| W303 | net CPM/15′/μg | |
|---|---|---|
| cytosol | 312 | |
| mitochondria | 297 | |
| microsomes | 178 | |
| W303/pTG10201 | (Prom CYC1 3β HSDH PGK term) | Percentage |
| cytosol | 6577 | 9.7% |
| mitochondria | 42308 | 62.7% |
| microsomes | 18590 | 27.5% |

The activity measurements coincided with the results of the Western blot. Activity was found in the mitochondrial and microsomal fraction. No activity was present in the cytosol nor in any fraction obtained from untransformed yeast. After a 15 minutes incubation at 37° C., the conversion of pregnenolone (0.8 μM) into progesterone was measured for 1 μg amounts of the following fractions: mitochondria, 60% conversion; micro-somes, 15% conversion, cytosol, 3% conversion. The reaction was not linear with time, but this point was not investigated further. The conversion of pregnenolone into progesterone was demonstrated in vivo (see below).

e) In vivo activity of 3β HSDH

Bioconversion of pregnenolone into progesterone:

Transformed yeast cells were grown in the presence of 100 μg/ml of pregnenolone and samples were extracted and analyzed by RP-HPLC for conversion into progesterone. The preliminary results showed the accumulation of progesterone in the culture medium of transformed yeast. 15% of pregnenolone was converted into progesterone in 2 days.

EXAMPLE 33

Construction, transformation and bioconversion from an expression cassette encoding human 3β-HSDH and bovine P450 17α in *Saccharomyces cerevisiae*

1. Construction of transfer vectors for human 3β-HSDH and bovine $P_{450}$ 17α a) Sub-cloning of the DNA coding for the bovine $P_{450}$ 17α:

The cDNA coding for the bovine $P_{450}$ in plasmid pGB17α-5 described in example 14 (FIG. 24) was reformatted on SalI MluI restriction sites by introduction of a MluI site into the XhoI site of the vector. The SalI MluI fragment was subcloned into pTG10031 (example 32, FIG. 48) under control of the CYC1 promoter. This vector was called pTG10058.

b) Sub-cloning of the human 3β-HSDH type I:

The vector pTG 10065 with cDNA encoding human 3β-HSDH type I under control of the Gal10/CYC1 promoter was obtained in Example 32 (FIG. 56).

2. Construction of a yeast—E.coli shuttle vector for the expression of human 3βHSDH type I and bovine $P_{450}17\alpha$.

Using recombination vectors, assembly of the desired expression plasmid via recombination in vivo can be accomplished. Plasmids containing $CYC1_{prom}$-$PGK_{term}$ and the cDNAs for bovine $P_{450}$ 17α or human 3β-HSDH type I were coupled with LEU2 or URA3-d as selection markers, respectively. Recombination vectors were generated containing the yeast 2 μm, a replicon, an expression cassette with the $CYC1_{prom}$-$PGK_{term}$ and different selection markers URA3-d (pTG10259) or LEU2 (pTG10260). pTG10259 is identical to the previously described recombination vector pTG10042 previously described in Example 32 (FIG. 52) except that the single XbaI site contained in the 2 μm region was replaced by a XbaI site, obtained through filling in by the Klenow polymerase and religation.

The LEU2 containing recombination vector was constructed as follows. Into a plasmid containing the LEU2 gene (Genbank locus YSCLEU2, accession number J01333), HindIII sites into the HpaI site (located at position 241 were introduced in YSCLEU2, using as an adaptor oligonucleotide OTG4464: CACAAGCTTGTG (SEQ ID NO: 78)) and SalI site (at position 2213 in YSCLEU2, using as an adaptor oligonucleotide OTG4463: TCGAGG-GAAGCT (SEQ ID NO: 79)). The HindIII fragment was cloned into pTG10013 (see FIG. 50) digested with HindIII restriction enzyme and was treated with phosphatase. This yielded both orientations, pTG10023 and pTG10024. A NotI fragment containing the expression block of pTG10031 (FIG. 48) was subcloned into pTG10023 and yielded pTG10158. The orientation of the selection marker and the expression block in pTG10158 was similar to that present in pTG10042 (FIG. 52). pTG10158 generated pTG10260 simply by eliminating the single XbaI site contained in the 2 μm region, as done above. The expression blocks from pTG10065 (human 3βB-HSDH type I) and pTG10058 (bovine $P_{450}$ 17α), were introduced next, yielding the final expression plasmids, respectively pTG10261 and pTG10269.

3. Transformation of Saccharomyces cerevisiae

Yeast strain W303-1B was transformed using a transformation protocol described by Lauermann, Curr. Genetics, Vol. 20, pp. 1–3, (1991). Ethanol improved the transformation efficiency of intact yeast cells. The yeast cells were transformed with 1 μg of pTG10261+pTG10269 (no carrier DNA was utilized). After transformation and plating out on agar plates containing YNBG+casamino acids 0.01%+WAH or YNBG casamino acids 0.01%+WAHL, candidate colonies were confirmed on selective medium. Selection was done on YNBG+casamino acids 0.01%+WAH (W=Trp, A=adenine, H=His). PCR was used to confirm the simultaneous presence of the selective marker and the cDNA associated with it.

4. In vivo activity of $P_{450}$ 17α and 3β-HSDH in Saccharomyces cerevisiae

Bioconversion was measured with 100 μg/ml of pregnenolone incubated at 30° C. with cells on YNB+glycerol+WAH medium. Samples were taken after 2 days, then were extracted and analyzed by RP-HPLC. Values for 17α-hydroxyprogesterone (17OH-PROG) and progesterone (PROG) were expressed as μg/ml with duplicate data from different clones. The following results were obtained.

|  | Product | | Product | |
|---|---|---|---|---|
|  | PROG | 17OH-PROG | PROG | 17OH-PROG |
| W303-1B pTG10261 + pTG10269 | 1.6 | 3.2 | 0.6 | 4.6 |

The bioconversion of pregnenolone into 17α-hydroxyprogesterone was achieved in yeast by coexpression of 3β-HSDH and $P_{450}$ 17α.

EXAMPLE 34

In vivo activity of bovine $P_{450}17\alpha$ in transformed Kluyveromyces lactis Transformation of K.lactis strain CBS 2360 was performed with pGB 17α-5 as described in Example 14 and in vivo activity was determined in the whole cells of the transformed K.lactis strain. Four independent transformants (17α-3, 17α-7, 17α-10 and 17α-11) were grown in rich medium (10 g of yeast extracts, 10 g of bactopeptone and 20 g of glucose/liter) for 72 hours to reach an A600 of at least 30. The cells were harvested and resuspended at $1 \times 10^6$ cells/ml (A600=1).

Five ml of culture were incubated in the presence of $^3$H-labelled progesterone (20 μM) for 24 hours at 28° C. and then were extracted with dichloromethane. RP-HPLC analysis showed that progesterone was specifically transformed into 17α-hydroxyprogesterone. The amount of 17α-hydroxyprogesterone was about 40% (about 23% to 58% depending on the transformant) of the substrat added (see FIG. 57 corresponding to 17α-3). No androstenedione, which was the product of the C17-20-lyase activity of $P_{450}17\alpha$, was detected.

$^3$H-labelled 17α-hydroxyprogesterone was also incubated with the transformants under the conditions described above and after 24 hours of incubation, no androstenedione was detected. These data indicate that the bovine $P_{450}17\alpha$ expressed in K.lactis under the lactase promoter does not show any activity C17-20 lyase.

Various modifications of the products and method of the invention may be made without departing from the spirit or scope thereof and it is to be understood that the invention is intended to be limited only as defined in the appended claims.

What we claim is:

1. An expression cassette comprising a heterologous DNA encoding two or more enzymes from the metabolic pathway for the bioconversion of cholesterol to hydrocortisone wherein one of the enzymes is a bovine enzyme which catalyzes the oxidation of progesterone to 17α-hydroxyprogesterone and the remaining one or more bovine or human enzymes catalyze at least one reaction selected from the group consisting of the oxidation of cholesterol to pregnenolone by bovine enzyme; the conversion of pregnenolone to progesterone by human enzyme; the oxidation of the 17α-hydroxyprogesterone to cortexolone by bovine enzyme; and the oxidation of cortexolone to hydrocortisone by bovine enzyme; and wherein the heterologous DNA is operably linked to control sequences required to express the encoded enzymes in a recombinant host.

2. An expression cassette comprising a heterologous DNA encoding an enzyme from the metabolic pathway for the bioconversion of cholesterol to hydrocortisone which is a bovine enzyme which catalyzes the oxidation of progesterone to 17α-hydroxyprogesterone and further comprising one or more additional heterologous DNAs encoding one or more additional bovine or human enzymes from the metabolic pathway for the bioconversion of cholesterol to hydrocortisone, which one or more additional enzymes catalyze at least one reaction selected from the group consisting of: the oxidation of cholesterol to pregnenolone by bovine enzyme; the oxidation of pregnenolone to progesterone by human enzyme; the oxidation of 17α-hydroxyprogesterone to cortexolone by bovine enzyme; and the oxidation of cortexolone to hydrocortisone by bovine enzyme; and wherein each of the heterologous DNAs is operably linked to control sequences required to express the encoded enzymes in a recombinant host.

3. The expression cassette according to claim 1 wherein the enzyme that catalyzes the oxidation of progesterone to 17α-hydroxyprogesterone is bovine steroid-17-α-hydroxylase ($P_{450}17\alpha$) and the remaining one or more bovine or human enzymes are selected from the group consisting of bovine side-chain cleaving enzyme $P_{450}SCC$); human 3β-hydroxysteroid hydrogenase/isomerase (3β-HSD); bovine adrenodoxin (ADX); bovine adrenodoxin reductase (ADR); bovine NADPH cytochrome P450 reductase (RED); bovine steroid-21-hydroxylase ($P_{450}C21$) and bovine steroid-11-β-hydroxylase ($P_{450}11\beta$).

4. A recombinant host cell and progeny thereof comprising at least one expression cassette according to claim 1.

5. The recombinant host cell and progeny thereof according to claim 4, wherein the host is a micro-organism.

6. The recombinant host cell and progeny thereof according to claim 5, wherein the host is a species of Saccharomyces, Kluyveromyces or Bacillus or *Escherichia coli*.

7. A recombinant host cell and progeny thereof comprising a heterologous DNA encoding two or more enzymes from the metabolic pathway for the bioconversion of cholesterol to hydrocortisone wherein one of the enzymes is a bovine enzyme which catalyzes the oxidation of progesterone to 17α-hydroxyprogesterone and the remaining one or more bovine or human enzymes catalyzes at least one reaction selected from the group consisting of: the oxidation of cholesterol to pregnenolone by bovine enzyme; the conversion of pregnenolone to progesterone by human enzyme; the oxidation of the 17α-hydroxyprogesterone to cortexolone by bovine enzyme; and the oxidation of cortexolone to hydrocortisone by bovine enzyme; and wherein the heterologous DNA is operably linked to control sequences required to express the encoded enzymes in the recombinant host.

8. The recombinant host cell according to claim 7 wherein the bovine enzyme that catalyzes the oxidation of progesterone to 17α-hydroxyprogesterone is steroid-17-α-hydroxylase ($P_{450}17\alpha$) and the remaining one or more bovine or human enzymes are selected from the group consisting of: bovine side-chain cleaving enzyme ($P_{450}SCC$); human 3β-hydroxysteroid dehydrogenase/isomerase (3β-HSD); bovine adrenodoxin (ADX); bovine adrenodoxin reductase (ADR); bovine NADPH cytochrome $P_{450}$ reductase (RED); bovine steroid-21-hydroxylase ($P_{450}C21$) and bovine steroid-11-β-hydroxylase ($P_{450}11\beta$).

9. The recombinant host cell according to claim 7 wherein the enzyme that catalyzes the oxidation of progesterone to 17α-hydroxyprogesterone is bovine steroid-17-α-hydroxylase ($P_{450}17\alpha$) and the remaining one or more enzymes includes at least bovine steroid-21-hydroxylase ($P_{450}C21$).

10. The recombinant host cell of claim 7 wherein the host cell is Kluyveromyces species and wherein the enzyme that catalyzes the oxidation of progesterone to 17α-hydroxyprogesterone is bovine steroid-17-α-hydroxylase ($P_{450}17\alpha$) and the remaining one or more enzymes includes at least bovine steroid-21 -hydroxylase ($P_{450}C21$).

11. A method for making two or more enzymes from the metabolic pathway for the bioconversion of cholesterol to hydrocortisone comprising incubating the recombinant host cell of claim 6 in a nutrient medium under conditions where the two or more enzymes encoded by the heterologous DNA are expressed and accumulate.

12. A method for the selective oxidation of a compound to an oxidized product in vitro, which process comprises the steps of: (a) incubating the compound to be oxidized in the presence of the enzymes produced in the method of claim 11 under conditions where the compound is oxidized and the oxidized product accumulates, and (b) recovering the oxidized product.

13. A method for the selective oxidation of a compound to an oxidized product, which process comprises the steps of: (a) incubating the compound to be oxidized in the presence of the recombinant host cells of claim 6 under conditions where the compound is oxidized and the oxidized product accumulates, and (b) recovering the oxidized product.

14. The method according to claim 13, wherein one oxidation is the oxidation of progesterone to 17α-hydroxyprogesterone and the other oxidation is selected from the group consisting of: the oxidation of cholesterol to pregnenolone; the conversion of pregnenolone to progesterone; the oxidation of the 17α-hydroxyprogesterone to cortexolone; and the oxidation of cortexolone to hydrocortisone.

15. The method according to claim 14 wherein the two oxidations are effected simultaneously on the same compound in one step.

16. The method according to claim 14 wherein one oxidation is the conversion of progesterone to 17α-hydroxyprogesterone and the other oxidation is the conversion of 17α-hydroxyprogesterone to cortexolone.

17. In a method for the preparation of hydrocortisone from sterols, comprising culturing a recombinant host cell in a nutrient medium, the improvement comprising culturing a recombinant host cell of claim 7.

18. A method for selective oxidation of a compound to an oxidized product, which method comprises the steps of: (a) incubating the compound to be oxidized in the presence of the recombinant host cells of claim 7 under conditions where the compound is oxidized and the oxidized product accumulates, and (b) recovering the oxidized product.

19. The method according to claim 18 wherein the enzyme that catalyzes the oxidation of progesterone to 17α-hydroxyprogesterone is steroid-17-α-hydroxylase ($P_{450}17\alpha$) and the remaining one or more enzymes includes at least steroid-21-hydroxylase ($P_{450}C21$).

* * * * *

SEQUENCE LISTING (1) GENERAL INFORMATION:

(iii) NUMBER OF SEQUENCES: 79

(2) INFORMATION FOR SEQ ID NO: 1:

(i) SEQUENCE CHARACTERISTICS:
        (A) LENGTH: 37 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER SSC-1

(xi) SEQUENCE DESCRIPTION: SEQ ID NO: 1:

GGCTGACGAA GTCCTGAGAC ACTGGATTCA GCACTGG                                37

(2) INFORMATION FOR SEQ ID NO: 2:

(i) SEQUENCE CHARACTERISTICS:
        (A) LENGTH: 177 BASE PAIRS
        (B) TYPE: NUCLEIC ACID
        (C) STRANDEDNESS: DOUBLE
        (D) TOPOLOGY: LINEAR (ix) FEATURE:
        (D) OTHER INFORMATION: SYNTHETIC
            PSTI/HINDIII FRAGMENT (xi) SEQUENCE DESCRIPTION: SEQ ID NO: 2:

TGCAGCAGCG GCGGCAATCA GTACTAAGAC CCCTAGGCCT                             40

TACAGTGAGA TCCCCTCCCC TGGTGACAAT GGCTGGCTTA                             80

ACCTCTACCA TTTCTGGAGG GAGAAGGGCT CACAGAGAAT                             120

CCACTTTCGC CACATCGAGA ACTTCCAGAA GTATGGCCCC                             160

ATTTACAGGG AGAAGCT                                                     177

(2) INFORMATION FOR SEQ ID NO: 3:

(i) SEQUENCE CHARACTERISTICS:
        (A) LENGTH: 7336 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: PLASMID pBHA-1

(xi) SEQUENCE DESCRIPTION: SEQ ID NO: 3:

AATTCACCTC GAAAGCAAGC TGATAAACCG ATACAATTAA                             40

AGGCTCCTTT TGGAGCCTTT TTTTTTGGAG ATTTTCAACG                             80

TGAAAAAATT ATTATTCGCA ATTCCAAGCT AATTCACCTC                             120

GAAAGCAAGC TGATAAACCG ATACAATTAA AGGCTCCTTT                             160

TGGAGCCTTT TTTTTGGAG ATTTTCAACG TGAAAAAATT                              200

ATTATTCGCA ATTCCAAGCT CTGCCTCGCG CGTTTCGGTG                             240

ATGACGGTGA AAACCTCTGA CACATGCAGC TCCCGGAGAC                             280

GGTCACAGCT TGTCTGTAAG CGGATGCAGA TCACGCGCCC                             320

TGTAGCGGCG CATTAAGCGC GGCGGGTGTG GTGGTTACGC                             360

```
GCAGCGTGAC CGCTACACTT GCCAGCGCCC TAGCGCCCGC        400

TCCTTTCGCT TTCTTCCCTT CCTTTCTCGC CACGTTCGCC        440

GGCTTTCCCC GTCAAGCTCT AAATCGGGGG CTCCCTTTAG        480

GGTTCCGATT TAGTGCTTTA CGGCACCTCG ACCCCAAAAA        520

ACTTGATTAG GGTGATGGTT CACGTAGTGG GCCATCGCCC        560

TGATAGACGG TTTTTCGCCC TTTGACGTTG GAGTCCACGT        600

TCTTTAATAG TGGACTCTTG TTCCAAACTG GAACAACACT        640

CAACCCTATC TCGGTCTATT CTTTTGATTT ATAAGGGATT        680

TTGCCGATTT CGGCCTATTG GTTAAAAAAT GAGCTGATTT        720

AACAAAAATT TAACGCGAAT TTTAACAAAA TATTAACGTT        760

TACAATTTGA TCTGCGCTCG GTCGTTCGGC TGCGGCGAGC        800

GGTATCAGCT CACTCAAAGG CGGTAATACG GTTATCCACA        840

GAATCAGGGG ATAACGCAGG AAAGAACATG TGAGCAAAAG        880

GCCAGCAAAA GGCCAGGAAC CGTAAAAAGG CCGCGTTGCT        920

GGCGTTTTTC CATAGGCTCC GCCCCCCTGA CGAGCATCAC        960

AAAAATCGAC GCTCAAGTCA GAGGTGGCGA AACCCGACAG       1000

GACTATAAAG ATACCAGGCG TTTCCCCCTG GAAGCTCCCT       1040

CGTGCGCTCT CCTGTTCCGA CCCTGCCGCT TACCGGATAC       1080

CTGTCCGCCT TTCTCCCTTC GGGAAGCGTG GCGCTTTCTC       1120

ATAGCTCACG CTGTAGGTAT CTCAGTTCGG TGTAGGTCGT       1160

TCGCTCCAAG CTGGGCTGTG TGCACGAACC CCCCGTTCAG       1200

CCCGACCGCT GCGCCTTATC CGGTAACTAT CGTCTTGAGT       1240

CCAACCCGGT AAGACACGAC TTATCGCCAC TGGCAGCAGC       1280

CACTGGTAAC AGGATTAGCA GAGCGAGGTA TGTAGGCGGT       1320

GCTACAGAGT TCTTGAAGTG GTGGCCTAAC TACGGCTACA       1360

CTAGAAGGAC AGTATTTGGT ATCTGCGCTC TGCTGAAGCC       1400

AGTTACCTTC GGAAAAAGAG TTGGTAGCTC TTGATCCGGC       1440

AAACAAACCA CCGCTGGTAG CGGTGGTTTT TTTGTTTGCA       1480

AGCAGCAGAT TACGCGCAGA AAAAAAGGAT CTCAAGAAGA       1520

TCCTTTGATC TTTTCTACGG GGTCTGACGC TCAGTGGAAC       1560

GAAAACTCAC GTTAAGGGAT TTTGGTCATG AGATTATCAA       1600

AAAGGATCTT CACCTAGATC CTTTTAAATT AAAAATGAAG       1640

TTTTAAATCA ATCTAAAGTA TATATGAGTA AACTTGGTCT       1680

GACAGTTACC AATGCTTAAT CAGTGAGGCA CCTATCTCAG       1720

CGATCTGTCT ATTTCGTTCA TCCATAGTTG CCTGACTCCC       1760

CGTCGTGTAG ATAACTACGA TACGGGAGGG CTTACCATCT       1800

GGCCCCAGTG CTGCAATGAT ACCGCGAGAC CCACGCTCAC       1840

CGGCTCCAGA TTTATCAGCA ATAAACCAGC CAGCCGGAAG       1880

GGCCGAGCGC AGAAGTGGTC CTGCAACTTT ATCCGCCTCC       1920
```

-continued

| | |
|---|---|
| ATCCAGTCTA TTAATTGTTG CCGGGAAGCT AGAGTAAGTA | 1960 |
| GTTCGCCAGT TAATAGTTTG CGCAACGTTG TTGCCATTGC | 2000 |
| TGCAGGCATC GTGGTGTCAC GCTCGTCGTT TGGTATGGCT | 2040 |
| TCATTCAGCT CCGGTTCCCA ACGATCAAGG CGAGTTACAT | 2080 |
| GATCCCCCAT GTTGTGCAAA AAAGCGGTTA GCTCCTTCGG | 2120 |
| TCCTCCGATC GTTGTCAGAA GTAAGTTGGC CGCAGTGTTA | 2160 |
| TCACTCATGG TTATGGCAGC ACTGCATAAT TCTCTTACTG | 2200 |
| TCATGCCATC CGTAAGATGC TTTTCTGTGA CTGGTGAGTA | 2240 |
| CTCAACCAAG TCATTCTGAG AATAGTGTAT GCGGCGACCG | 2280 |
| AGTTGCTCTT GCCCGGCGTC AACACGGGAT AATACCGCGC | 2320 |
| CACATAGCAG AACTTTAAAA GTGCTCATCA TTGGAAAACG | 2360 |
| TTCTTCGGGG CGAAAACTCT CAAGGATCTT ACCGCTGTTG | 2400 |
| AGATCCAGTT CGATGTAACC CACTCGTGCA CCCAACTGAT | 2440 |
| CTTCAGCATC TTTTACTTTC ACCAGCGTTT CTGGGTGAGC | 2480 |
| AAAAACAGGA AGGCAAAATG CCGCAAAAAA GGGAATAAGG | 2520 |
| GCGACACGGA AATGTTGAAT ACTCATACTC TTCCTTTTTC | 2560 |
| AATATTATTG AAGCAGACAG TTTTATTGTT CATGATGATA | 2600 |
| TATTTTTATC TTGTGCAATG TAACATCAGA GATTTTGAGA | 2640 |
| CACAACGTGG CTTTGTTGAA TAAATCGAAC TTTTGCTGAG | 2680 |
| TTGACTCCCC GCGCGCGATG GGTCGAATTT GCTTTCGAAA | 2720 |
| AAAAAGCCCG CTCATTAGGC GGGCTAAAAA AAAGCCCGCT | 2760 |
| CATTAGGCGG GCTCGAATTT CTGCCATTCA TCCGCTTATT | 2800 |
| ATCACTTATT CAGGCGTAGC AACCAGGCGT TTAAGGGCAC | 2840 |
| CAATAACTGC CTTAAAAAAA TTACGCCCCG CCCTGCCACT | 2880 |
| CATCGCAGTA CTGTTGTAAT TCATTAAGCA TTCTGCCGAC | 2920 |
| ATGGAAGCCA TCACAGACGG CATGATGAAC CTGAATCGCC | 2960 |
| AGCGGCATCA GCACCTTGTC GCCTTGCGTA TAATATTTGC | 3000 |
| CCATAGTGAA AACGGGGGCG AAGAAGTTGT CCATATTCGC | 3040 |
| CACGTTTAAA TCAAAACTGG TGAAACTCAC CCAGGGATTG | 3080 |
| GCTGAGACGA AAAACATATT CTCAATAAAC CCTTTAGGGA | 3120 |
| AATAGGCCAG GTTTTCACCG TAACACGCCA CATCTTGCGA | 3160 |
| ATATATGTGT AGAAACTGCC GGAAATCGTC GTGGTATTCA | 3200 |
| CTCCAGAGCG ATGAAAACGT TTCAGTTTGC TCATGGAAAA | 3240 |
| CGGTGTAACA AGGGTGAACA CTATCCCATA TCACCAGCTC | 3280 |
| ACCGTCTTTC ATTGCCATAC GAAATTCCGG ATGAGCATTC | 3320 |
| ATCAGGCGGG CAAGAATGTG AATAAAGGCC GGATAAAACT | 3360 |
| TGTGCTTATT TTTCTTTACG GTCTTTAAAA AGGCCGTAAT | 3400 |
| ATCCAGCTAA CGGTCTGGT TATAGGTACA TTGAGCAACT | 3440 |
| GACTGAAATG CCTCAAAATG TTCTTTACGA TGCCATTGGG | 3480 |
| ATATATCAAC GGTGGTATAT CCAGTGATTT TTTTCTCCAT | 3520 |

```
TTTAGCTTCC TTAGCTCCTG AAAATCTCGA TAACTCAAAA              3560

AATACGCCCG GTAGTGATCT TATTTCATTA TGGTGAAAGT              3600

TGGAACCTCT TACGTGCCGA TCAACGTCTC ATTTTCGCCA              3640

AAAGTTGGCC CAGGGCTTCC CGGTATCAAC AGGGACACCA              3680

GGATTTATTT ATTCTGCGAA GTGATCTTCC GTCACAGGTA              3720

TTTATTCGAA GACGAAAGGG CATCGCGCGC GGGGAATTCC              3760

CGGGAGAGCT CGATATCGCA TGCGGTACCT CTAGAAGAAG              3800

CTTGGAGACA AGGTAAAGGA TAAAACAGCA CAATTCCAAG              3840

AAAAACACGA TTTAGAACCT AAAAAGAACG AATTTGAACT              3880

AACTCATAAC CGAGAGGTAA AAAAAGAACG AAGTCGAGAT              3920

CAGGGAATGA GTTTATAAAA TAAAAAAAGC ACCTGAAAAG              3960

GTGTCTTTTT TTGATGGTTT TGAACTTGTT CTTTCTTATC              4000

TTGATACATA TAGAAATAAC GTCATTTTTA TTTTAGTTGC              4040

TGAAAGGTGC GTTGAAGTGT TGGTATGTAT GTGTTTTAAA              4080

GTATTGAAAA CCCTTAAAAT TGGTTGCACA GAAAAACCCC              4120

ATCTGTTAAA GTTATAAGTG ACTAAACAAA TAACTAAATA              4160

GATGGGGGTT TCTTTTAATA TTATGTGTCC TAATAGTAGC              4200

ATTTATTCAG ATGAAAAATC AAGGGTTTTA GTGGACAAGA              4240

CAAAAAGTGG AAAAGTGAGA CCATGGAGAG AAAAGAAAAT              4280

CGCTAATGTT GATTACTTTG AACTTCTGCA TATTCTTGAA              4320

TTTAAAAAGG CTGAAAGAGT AAAAGATTGT GCTGAAATAT              4360

TAGAGTATAA ACAAAATCGT GAAACAGGCG AAAGAAAGTT              4400

GTATCGAGTG TGGTTTTGTA AATCCAGGCT TTGTCCAATG              4440

TGCAACTGGA GGAGAGCAAT GAAACATGGC ATTCAGTCAC              4480

AAAAGGTTGT TGCTGAAGTT ATTAAACAAA AGCCAACAGT              4520

TCGTTGGTTG TTTCTCACAT TAACAGTTAA AAATGTTTAT              4560

GATGGCGAAG AATTAAATAA GAGTTTGTCA GATATGGCTC              4600

AAGGATTTCG CCGAATGATG CAATATAAAA AAATTAATAA              4640

AAATCTTGTT GGTTTTATGC GTGCAACGGA AGTGACAATA              4680

AATAATAAAG ATAATTCTTA TAATCAGCAC ATGCATGTAT              4720

TGGTATGTGT GGAACCAACT TATTTTAAGA ATACAGAAAA              4760

CTACGTGAAT CAAAAACAAT GGATTCAATT TTGGAAAAAG              4800

GCAATGAAAT TAGACTATGA TCCAAATGTA AAAGTTCAAA              4840

TGATTCGACC GAAAAATAAA TATAAATCGG ATATACAATC              4880

GGCAATTGAC GAAACTGCAA ATATCCTGT AAAGGATACG               4920

GATTTTATGA CCGATGATGA AGAAAAGAAT TTGAAACGTT              4960

TGTCTGATTT GGAGGAAGGT TTACACCGTA AAAGGTTAAT              5000

CTCCTATGGT GGTTTGTTAA AAGAAATACA TAAAAAATTA              5040

AACCTTGATG ACACAGAAGA AGGCGATTTG ATTCATACAG              5080
```

-continued

| | |
|---|---|
| ATGATGACGA AAAAGCCGAT GAAGATGGAT TTTCTATTAT | 5120 |
| TGCAATGTGG AATTGGGAAC GGAAAAATTA TTTTATTAAA | 5160 |
| GAGTAGTTCA ACAAACGGGC CAGTTTGTTG AAGATTAGAT | 5200 |
| GCTATAATTG TTATTAAAAG GATTGAAGGA TGCTTAGGAA | 5240 |
| GACGAGTTAT TAATAGCTGA ATAAGAACGG TGCTCTCCAA | 5280 |
| ATATTCTTAT TTAGAAAAGC AAATCTAAAA TTATCTGAAA | 5320 |
| AGGGAATGAG AATAGTGAAT GGACCAATAA TAATGACTAG | 5360 |
| AGAAGAAAGA ATGAAGATTG TTCATGAAAT TAAGGAACGA | 5400 |
| ATATTGGATA AATATGGGGA TGATGTTAAG GCTATTGGTG | 5440 |
| TTTATGGCTC TCTTGGTCGT CAGACTGATG GGCCCTATTC | 5480 |
| GGATATTGAG ATGATGTGTG TCATGTCAAC AGAGGAAGCA | 5520 |
| GAGTTCAGCC ATGAATGGAC AACCGGTGAG TGGAAGGTGG | 5560 |
| AAGTGAATTT TGATAGCGAA GAGATTCTAC TAGATTATGC | 5600 |
| ATCTCAGGTG GAATCAGATT GGCCGCTTAC ACATGGTCAA | 5640 |
| TTTTTCTCTA TTTTGCCGAT TTATGATTCA GGTGGATACT | 5680 |
| TAGAGAAAGT GTATCAAACT GCTAAATCGG TAGAAGCCCA | 5720 |
| AACGTTCCAC GATGCGATTT GTGCCCTTAT CGTAGAAGAG | 5760 |
| CTGTTTGAAT ATGCAGGCAA ATGGCGTAAT ATTCGTGTGC | 5800 |
| AAGGACCGAC AACATTTCTA CCATCCTTGA CTGTACAGGT | 5840 |
| AGCAATGGCA GGTGCCATGT TGATTGGTCT GCATCATCGC | 5880 |
| ATCTGTTATA CGACGAGCGC TTCGGTCTTA ACTGAAGCAG | 5920 |
| TTAAGCAATC AGATCTTCCT TCAGGTTATG ACCATCTGTG | 5960 |
| CCAGTTCGTA ATGTCTGGTC AACTTTCCGA CTCTGAGAAA | 6000 |
| CTTCTGGAAT CGCTAGAGAA TTTCTGGAAT GGGATTCAGG | 6040 |
| AGTGGACAGA ACGACACGGA TATATAGTGG ATGTGTCAAA | 6080 |
| ACGCATACCA TTTTGAACGA TGACCTCTAA TAATTGTTAA | 6120 |
| TCATGTTGGT TACGTATTTA TTAACTTCTC CTAGTATTAG | 6160 |
| TAATTATCAT GGCTGTCATG GCGCATTAAC GGAATAAAGG | 6200 |
| GTGTGCTTAA ATCGGGCCAT TTTGCGTAAT AAGAAAAAGG | 6240 |
| ATTAATTATG AGCGAATTGA ATTAATAATA AGGTAATAGA | 6280 |
| TTTACATTAG AAAATGAAAG GGGATTTTAT GCGTGAGAAT | 6320 |
| GTTACAGTCT ATCCCGGCAT TGCCAGTCGG GGATATTAAA | 6360 |
| AAGAGTATAG GTTTTTATTG CGATAAACTA GGTTTCACTT | 6400 |
| TGGTTCACCA TGAAGATGGA TTCGCAGTTC TAATGTGTAA | 6440 |
| TGAGGTTCGG ATTCATCTAT GGGAGGCAAG TGATGAAGGC | 6480 |
| TGGCGCTCTC GTAGTAATGA TTCACCGGTT TGTACAGGTG | 6520 |
| CGGAGTCGTT TATTGCTGGT ACTGCTAGTT GCCGCATTGA | 6560 |
| AGTAGAGGGA ATTGATGAAT TATATCAACA TATTAAGCCT | 6600 |
| TTGGGCATTT TGCACCCCAA TACATCATTA AAAGATCAGT | 6640 |
| GGTGGGATGA ACGAGACTTT GCAGTAATTG ATCCCGACAA | 6680 |

| | |
|---|---|
| CAATTTGATT AGCTTTTTTC AACAAATAAA AAGCTAAAAT | 6720 |
| CTATTATTAA TCTGTTCAGC AATCGGGCGC GATTGCTGAA | 6760 |
| TAAAAGATAC GAGAGACCTC TCTTGTATCT TTTTTATTTT | 6800 |
| GAGTGGTTTT GTCCGTTACA CTAGAAAACC GAAAGACAAT | 6840 |
| AAAAATTTTA TTCTTGCTGA GTCTGGCTTT CGGTAAGCTA | 6880 |
| GACAAAACGG ACAAAATAAA AATTGGCAAG GGTTTAAAGG | 6920 |
| TGGAGATTTT TTGAGTGATC TTCTCAAAAA ATACTACCTG | 6960 |
| TCCCTTGCTG ATTTTTAAAC GAGCACGAGA GCAAAACCCC | 7000 |
| CCTTTGCTGA GGTGGCAGAG GGCAGGTTTT TTTGTTTCTT | 7040 |
| TTTTCTCGTA AAAAAAGAA AGGTCTTAAA GGTTTTATGG | 7080 |
| TTTTGGTCGG CACTGCCGAC AGCCTCGCAG GACACACACT | 7120 |
| TTATGAATAT AAAGTATAGT GTGTTATACT TTACTTGGAA | 7160 |
| GTGGTTGCCG GAAAGAGCGA AAATGCCTCA CATTTGTGCC | 7200 |
| ACCTAAAAAG GAGCGATTTA CATATGAGTT ATGCAGTTTG | 7240 |
| TAGAATGCAA AAAGTGAAAT CAGGGGATC CTCTAGAGTC | 7280 |
| GAGCTCAAGC TAGCTTGGTA CGTACCAGAT CTGAGATCAC | 7320 |
| GCGTTCTAGA GGTCGA | 7336 |

(2) INFORMATION FOR SEQ ID NO: 4:

(i) SEQUENCE CHARACTERISTICS:
        (A) LENGTH: 27 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SPHI/STUI FRAGMENT
           IN pGBSCC-4

(xi) SEQUENCE DESCRIPTION: SEQ ID NO: 4:

| | |
|---|---|
| CATATGATCA GTACTAAGAC CCCTAGG | 27 |

(2) INFORMATION FOR SEQ ID NO: 5:

(i) SEQUENCE CHARACTERISTICS:
        (A) LENGTH: 31 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SPHI/STUI FRAGMENT
           IN pGBSCC-4

(xi) SEQUENCE DESCRIPTION: SEQ ID NO: 5:

| | |
|---|---|
| CCTAGGGGTC TTAGTACTGA TCATATGCAT G | 31 |

(2) INFORMATION FOR SEQ ID NO: 6:

(i) SEQUENCE CHARACTERISTICS:
        (A) LENGTH: 41 BASE PAIRS
        (B) TYPE: NUCLEIC ACID
        (C) STRANDEDNESS: DOUBLE
        (D) TOPOLOGY: UNKNOWN (ix) FEATURE:

(D) OTHER INFORMATION: SPHI/STUI FRAGMENT
                IN pGBSSC-3, FIGURE 7

(xi) SEQUENCE DESCRIPTION: SEQ ID NO: 6:

CTGCAGCAGC GGCGGCAATC AGTACTAAGA CCCCTAGGCC T                      41

(2) INFORMATION FOR SEQ ID NO: 7:

(i) SEQUENCE CHARACTERISTICS:
        (A) LENGTH: 24 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: NDEI RESTRICTION
            SITE AT THE ATG INITIATION CODON OF
            THE LACZ GENE IN PTZ18R (xi) SEQUENCE DESCRIPTION: SEQ ID NO: 7:

CAGGAAACAC ATATGACCAT GATT                                        24

(2) INFORMATION FOR SEQ ID NO: 8:

(i) SEQUENCE CHARACTERISTICS:
        (A) LENGTH: 108 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: LACTASE TERMINATOR (xi) SEQUENCE DESCRIPTION: SEQ ID NO: 8:

TCGACGCGGC CGCAGATCTG ATATCTCGAG AATTTATACT                        40

TAGATAAGTA TGTACTTACA GGTATATTTC TATGAGATAC                        80

TGATGTATAC ATGCATGATA ATATTTAA                                    108

(2) INFORMATION FOR SEQ ID NO: 9:

(i) SEQUENCE CHARACTERISTICS:
        (A) LENGTH: 44 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SALI/XHOI FRAGMENT
            IN pGBSCC-6

(xi) SEQUENCE DESCRIPTION: SEQ ID NO: 9:

TCGACAAAAA TGATCAGTAC TAAGACTCCT AGGCCTATCG ATTC                   44

(2) INFORMATION FOR SEQ ID NO: 10:

(i) SEQUENCE CHARACTERISTICS:
        (A) LENGTH: 44 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SALI/XHOI FRAGMENT
            IN pGBSCC-6

(xi) SEQUENCE DESCRIPTION: SEQ ID NO: 10:

TCGAGAATCG ATAGGCCTAG GAGTCTTAGT ACTGATCATT TTTG                   44

(2) INFORMATION FOR SEQ ID NO: 11:

(i) SEQUENCE CHARACTERISTICS:
        (A) LENGTH: 158 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SALI/XHOI
            SYNTHETIC DNA IN PLASMID pGBSCC-11

(xi) SEQUENCE DESCRIPTION: SEQ ID NO: 11:

```
TCGACAAAAA TGTTGGCTCG AGGTTTGCCA TTGAGATCCG                40
CTTTGGTTAA GGCTTGTCCA CCAATCTTGT CCACTGTTGG                80
TGAAGGTTGG GGTCACCACA GAGTTGGTAC TGGTGAAGGT               120
GCTGGTATCA GTACTAAGAC TCCTAGGCCT ATCGATTC                 158
```

(2) INFORMATION FOR SEQ ID NO: 12:

(i) SEQUENCE CHARACTERISTICS:
        (A) LENGTH: 158 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SALI/XHOI
            SYNTHETIC DNA IN PLASMID pGBSCC-11

(xi) SEQUENCE DESCRIPTION: SEQ ID NO: 12:

```
TCGAGAATCG ATAGGCCTAG GAGTCTTAGT ACTGATACCA                40
GCACCTTCAC CAGTACCAAC TCTGTGGTGA CCCCAACCTT                80
CACCAACAGT GGACAAGATT GGTGGACAAG CCTTAACCAA               120
AGCGGATCTC AATGGCAAAC CTCGAGCCAA CATTTTTG                 158
```

(2) INFORMATION FOR SEQ ID NO: 13:

(i) SEQUENCE CHARACTERISTICS:
        (A) LENGTH: 161 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: SALI/XHOI
            SYNTHETIC DNA IN pGBSSC-14

(xi) SEQUENCE DESCRIPTION: SEQ ID NO: 13:

```
TCGACAAAAA TGTTGTCTCG AGCTATCTTC AGAAACCCAG                40
TTATCAACAG AACTTTGTTG AGAGCTAGAC CAGGTGCTTA                80
CCACGCTACT AGATTGACTA AGAACACTTT CATCCAATCC               120
AGAAAGTACA TCAGTACTAA GACTCCTAGG CCTATCGATT               160
C                                                         161
```

(2) INFORMATION FOR SEQ ID NO: 14:

(i) SEQUENCE CHARACTERISTICS:
        (A) LENGTH: 161 BASE PAIRS
        (B) TYPE: NUCLEIC ACID
        (C) STRANDEDNESS: DOUBLE
        (D) TOPOLOGY: UNKNOWN (ix) FEATURE:
            (D) OTHER INFORMATION: SALI/XHOI
                SYNTHETIC DNA IN pGBSCC-14

(xi) SEQUENCE DESCRIPTION: SEQ ID NO: 14:

TCGAGAATCG ATAGGCCTAG GAGTCTTAGT ACTGATGTAC                          40

TTTCTGGATT GGATGAAAGT GTTCTTAGTC AATCTAGTAG                          80

CGTGGTAAGC ACCTGCTCTA GCTCTCAACA AAGTTCTGTT                         120

GATAACTGGG TTTCTGAAGA TAGCTCGAGA CAACATTTTT                         160

G                                                                  161

(2) INFORMATION FOR SEQ ID NO: 15:

(i) SEQUENCE CHARACTERISTICS:
            (A) LENGTH: 30 BASE PAIRS
            (B) TYPE: NUCLEIC ACID
            (C) STRANDEDNESS: DOUBLE
            (D) TOPOLOGY: LINEAR (ix) FEATURE:
            (D) OTHER INFORMATION: OLIGOMER 17
                ALPHA-1

(xi) SEQUENCE DESCRIPTION: SEQ ID NO: 15:

AGTGGCCACT TTGGGACGCC CAGAGAATTC                                    30

(2) INFORMATION FOR SEQ ID NO: 16:

(i) SEQUENCE CHARACTERISTICS:
            (A) LENGTH: 36 BASE PAIRS
            (B) TYPE: NUCLEIC ACID
            (C) STRANDEDNESS: DOUBLE
            (D) TOPOLOGY: LINEAR (ix) FEATURE:
            (D) OTHER INFORMATION: OLIGOMER 17
                ALPHA-2

(xi) SEQUENCE DESCRIPTION: SEQ ID NO: 16:

GAGGCTCCTG GGGTACTTGG CACCAGAGTG CTTGGT                              36

(2) INFORMATION FOR SEQ ID NO: 17:

(i) SEQUENCE CHARACTERISTICS:
            (A) LENGTH: 43 BASE PAIRS
            (B) TYPE: NUCLEIC ACID
            (C) STRANDEDNESS: SINGLE
            (D) TOPOLOGY: LINEAR (ix) FEATURE:
            (D) OTHER INFORMATION: SEQUENCE OF pGB17
                ALPHA-3 MUTATED BY SITE DIRECTED
                MUTAGENESIS, FIGURE 23

(xi) SEQUENCE DESCRIPTION: SEQ ID NO: 17:

TCTTTGTCCT GACTGCTGCC ACCCAGACAC AATGTGGCTG CTC                      43

(2) INFORMATION FOR SEQ ID NO: 18:

(i) SEQUENCE CHARACTERISTICS:
            (A) LENGTH: 43 BASE PAIRS
            (B) TYPE: NUCLEIC ACID
            (C) STRANDEDNESS: SINGLE
            (D) TOPOLOGY: LINEAR (ix) FEATURE:

(D) OTHER INFORMATION: SYNTHETIC OLIGOMER
              17 ALPHA-3 WITH SALI SITE (xi) SEQUENCE DESCRIPTION: SEQ ID NO: 18:

TCTTTGTCCT GACTGCTGCC AGTCGACAAA AATGTGGCTG CTC        43

(2) INFORMATION FOR SEQ ID NO: 19:

(i) SEQUENCE CHARACTERISTICS:
        (A) LENGTH: 31 BASE PAIRS
        (B) TYPE: NUCLEIC ACID
        (C) STRANDEDNESS: DOUBLE
        (D) TOPOLOGY: LINEAR (ix) FEATURE:
        (D) OTHER INFORMATION: SEQUENCE OF pGB17
            ALPHA-3 MUTATED BY SITE DIRECTED
            MUTAGENESIS TO CREATE A NDEI SITE,
            FIGURE 25

(xi) SEQUENCE DESCRIPTION: SEQ ID NO: 19:

GCTGCCACCC AGACACAATG TGGCTGCTCC T                     31

(2) INFORMATION FOR SEQ ID NO: 20:

(i) SEQUENCE CHARACTERISTICS:
        (A) LENGTH: 31 BASE PAIRS
        (B) TYPE: NUCLEIC ACID
        (C) STRANDEDNESS: DOUBLE
        (D) TOPOLOGY: LINEAR (ix) FEATURE:
        (D) OTHER INFORMATION: SYNTHETIC OLIGOMER
            17 ALPHA-4

(xi) SEQUENCE DESCRIPTION: SEQ ID NO: 20:

GCTGCCACCC AGACCATATG TGGCTGCTCC T                     31

(2) INFORMATION FOR SEQ ID NO: 21:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER C21-1

(xi) SEQUENCE DESCRIPTION: SEQ ID NO: 21:

GATGATGCTG CAGGTAAGCA GAGAGAATTC                       30

(2) INFORMATION FOR SEQ ID NO: 22:

(i) SEQUENCE CHARACTERISTICS:
        (A) LENGTH: 15 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER C21-2

(xi) SEQUENCE DESCRIPTION: SEQ ID NO: 22:

AAGCAGAGAG AATTC                                       15

(2) INFORMATION FOR SEQ ID NO: 23:

(i) SEQUENCE CHARACTERISTICS:

(A) LENGTH:  36 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER C21-3

(xi) SEQUENCE DESCRIPTION: SEQ ID NO: 23:

CTTCCACCGG CCCGATAGCA GGTGAGCGCC ACTGAG                                  36

(2) INFORMATION FOR SEQ ID NO: 24:

(i) SEQUENCE CHARACTERISTICS:
        (A) LENGTH:  36 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER C21-4

(xi) SEQUENCE DESCRIPTION: SEQ ID NO: 24:

CTCACTGATA TCCATATGGT CCTCGCAGGG CTGCTG                                  36

(2) INFORMATION FOR SEQ ID NO: 25:

(i) SEQUENCE CHARACTERISTICS:
        (A) LENGTH:  27 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER C21-5

(xi) SEQUENCE DESCRIPTION: SEQ ID NO: 25:

AGCTCAGAAT TCCTTCTGGA TGGTCAC                                            27

(2) INFORMATION FOR SEQ ID NO: 26:

(i) SEQUENCE CHARACTERISTICS:
        (A) LENGTH:  12 BASE PAIRS
        (B) TYPE:  NUCLEIC ACID
        (C) STRANDEDNESS:  DOUBLE
        (D) TOPOLOGY:  UNKNOWN (ix) FEATURE:
        (D) OTHER INFORMATION:  FIGURE 29,
            pGBC21-2

(xi) SEQUENCE DESCRIPTION: SEQ ID NO: 26:

CCAGCCATGG TC                                                            12

(2) INFORMATION FOR SEQ ID NO: 27:

(i) SEQUENCE CHARACTERISTICS:
        (A) LENGTH:  9 BASE PAIRS
        (B) TYPE:  NUCLEIC ACID
        (C) STRANDEDNESS:  DOUBLE
        (D) TOPOLOGY:  UNKNOWN (ix) FEATURE:
        (D) OTHER INFORMATION:  FIGURE 29,
            pGBC21-2

(xi) SEQUENCE DESCRIPTION: SEQ ID NO: 27:

AAGGAATTC                                                                 9

(2) INFORMATION FOR SEQ ID NO: 28:

(i) SEQUENCE CHARACTERISTICS:
        (A) LENGTH: 21 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER C21-4

(xi) SEQUENCE DESCRIPTION: SEQ ID NO: 28:

CTCACTGATA TCCATATGGT C                         21

(2) INFORMATION FOR SEQ ID NO: 29:

(i) SEQUENCE CHARACTERISTICS:
        (A) LENGTH: 15 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER C21-5

(xi) SEQUENCE DESCRIPTION: SEQ ID NO: 29:

AAGGAATTCT GAGCT                             15

(2) INFORMATION FOR SEQ ID NO: 30:

(i) SEQUENCE CHARACTERISTICS:
        (A) LENGTH: 36 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER C21-6

(xi) SEQUENCE DESCRIPTION: SEQ ID NO: 30:

CCTCTGCCTG GGTCGACAAA AATGGTCCTC GCAGGG          36

(2) INFORMATION FOR SEQ ID NO: 31:

(i) SEQUENCE CHARACTERISTICS:
        (A) LENGTH: 36 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: PGBC21-2,
            FIGURE 33

(xi) SEQUENCE DESCRIPTION: SEQ ID NO: 31:

CCTCTGCCTG GGTCTCCAGC CATGGTCCTC GCAGGG          36

(2) INFORMATION FOR SEQ ID NO: 32:

(i) SEQUENCE CHARACTERISTICS:
        (A) LENGTH: 18 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER 11 BETA-1

(xi) SEQUENCE DESCRIPTION: SEQ ID NO: 32:

GGCAGTGTGC TGACACGA                            18

(2) INFORMATION FOR SEQ ID NO: 33:

(i) SEQUENCE CHARACTERISTICS:
        (A) LENGTH:  30 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER 11 BETA-2

(xi) SEQUENCE DESCRIPTION: SEQ ID NO: 33:

```
CCGCACCCTG GCCTTTGCCC ACAGTGCCAT                                    30
```

(2) INFORMATION FOR SEQ ID NO: 34:

(i) SEQUENCE CHARACTERISTICS:
        (A) LENGTH:  36 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER 11 BETA-3

(xi) SEQUENCE DESCRIPTION: SEQ ID NO: 34:

```
CAGCTCAAAG AGAGTCATCA GCAAGGGGAA GGCTGT                             36
```

(2) INFORMATION FOR SEQ ID NO: 35:

(i) SEQUENCE CHARACTERISTICS:
        (A) LENGTH:  42 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER 11 BETA-4

(xi) SEQUENCE DESCRIPTION: SEQ ID NO: 35:

```
TTTGATATCG AATTCCATAT GGGCACCAGA GGTGCTGCAG CC                      42
```

(2) INFORMATION FOR SEQ ID NO: 36:

(i) SEQUENCE CHARACTERISTICS:
        (A) LENGTH:  42 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER 11 BETA-5

(xi) SEQUENCE DESCRIPTION: SEQ ID NO: 36:

```
TAACGATATC CTCGAGGGTA CCTACTGGAT GGCCCGGAAG GT                      42
```

(2) INFORMATION FOR SEQ ID NO: 37:

(i) SEQUENCE CHARACTERISTICS:
        (A) LENGTH:  39 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER 11 BETA-6

(xi) SEQUENCE DESCRIPTION: SEQ ID NO: 37:

```
CTTCAGTCGA CAAAAATGGG CACCAGAGGT GCTGCAGCC                              39
```

(2) INFORMATION FOR SEQ ID NO: 38:

(i) SEQUENCE CHARACTERISTICS:
        (A) LENGTH: 18 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: REGION IN 11 BETA
            cDNA HOMOLOGOUS TO PRIMERS, FIGURE 36

(xi) SEQUENCE DESCRIPTION: SEQ ID NO: 38:

```
CGCCTACTGG GCACCAGA                                                    18
```

(2) INFORMATION FOR SEQ ID NO: 39:

(i) SEQUENCE CHARACTERISTICS:
        (A) LENGTH: 21 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: REGION IN 11 BETA
            cDNA HOMOLOGOUS TO PRIMERS, FIGURE 36

(xi) SEQUENCE DESCRIPTION: SEQ ID NO: 39:

```
GCCATCCAGT AGTCGTGTCA G                                                21
```

(2) INFORMATION FOR SEQ ID NO: 40:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER 11 BETA-4,
            FIGURE 36

(xi) SEQUENCE DESCRIPTION: SEQ ID NO: 40:

```
TTTGATATCG AATTCCATAT GGGCACCAGA                                       30
```

(2) INFORMATION FOR SEQ ID NO: 41:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER 11 BETA-5,
            FIGURE 36

(xi) SEQUENCE DESCRIPTION: SEQ ID NO: 41:

```
GCCATCCAGT AGGTACCCTC GAGGATATCG TTA                                   33
```

(2) INFORMATION FOR SEQ ID NO: 42:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: UNKNOWN (ix) FEATURE:
        (D) OTHER INFORMATION: OLIGOMER 11 BETA-6,
            FIGURE 37

(xi) SEQUENCE DESCRIPTION: SEQ ID NO: 42:

CTTCAGTCGA CAAAAATGGG CACCAGA                                           27

(2) INFORMATION FOR SEQ ID NO: 43:

(i) SEQUENCE CHARACTERISTICS:
        (A) LENGTH:  39 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER ADX-1

(xi) SEQUENCE DESCRIPTION: SEQ ID NO: 43:

CTTCAGTCGA CAAAAATGAG CAGCTCAGAA GATAAAATA                               39

(2) INFORMATION FOR SEQ ID NO: 44:

(i) SEQUENCE CHARACTERISTICS:
        (A) LENGTH:  40 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  OLIGOMER ADX-2

(xi) SEQUENCE DESCRIPTION: SEQ ID NO: 44:

TGTAAGGTAC CCGGGATCCT TATTCTATCT TTGAGGAGTT                              40

(2) INFORMATION FOR SEQ ID NO: 45:

(i) SEQUENCE CHARACTERISTICS:
        (A) LENGTH:  18 BASE PAIRS
        (B) TYPE:  NUCLEIC ACID
        (C) STRANDEDNESS:  DOUBLE
        (D) TOPOLOGY:  UNKNOWN (ix) FEATURE:
        (D) OTHER INFORMATION:  REGION OF ADX
            mRNA/cDNA HOMOLOGOUS TO THE PRIMERS,
            FIGURE 38

(xi) SEQUENCE DESCRIPTION: SEQ ID NO: 45:

CGAGCGCAGA GCAGCTCA                                                     18

(2) INFORMATION FOR SEQ ID NO: 46:

(i) SEQUENCE CHARACTERISTICS:
        (A) LENGTH:  18 BASE PAIRS
        (B) TYPE:  NUCLEIC ACID
        (C) STRANDEDNESS:  DOUBLE
        (D) TOPOLOGY:  UNKNOWN (ix) FEATURE:
        (D) OTHER INFORMATION:  REGION OF ADX
            mRNA/cDNA HOMOLOGOUS TO THE PRIMERS,
            FIGURE 38

(xi) SEQUENCE DESCRIPTION: SEQ ID NO: 46:

ATAGAATAAA TAGGAATA                                                     18

(2) INFORMATION FOR SEQ ID NO: 47:

(i) SEQUENCE CHARACTERISTICS:
           (A) LENGTH: 27 BASE PAIRS
           (B) TYPE: NUCLEIC ACID
           (C) STRANDEDNESS: SINGLE
           (D) TOPOLOGY: LINEAR (ix) FEATURE:
           (D) OTHER INFORMATION: OLIGOMER ADX-1,
               FIGURE 38

(xi) SEQUENCE DESCRIPTION: SEQ ID NO: 47:

CTTCAGTCGA CAAAAATGAG CAGCTCA                                              27

(2) INFORMATION FOR SEQ ID NO: 48:

(i) SEQUENCE CHARACTERISTICS:
           (A) LENGTH: 28 BASE PAIRS
           (B) TYPE: NUCLEIC ACID
           (C) STRANDEDNESS: SINGLE
           (D) TOPOLOGY: LINEAR (ix) FEATURE:
           (D) OTHER INFORMATION: OLIGOMER ADX-2,
               FIGURE 38

(xi) SEQUENCE DESCRIPTION: SEQ ID NO: 48:

ATAGAATAAG GATCCCGGGT ACCTTACA                                             28

(2) INFORMATION FOR SEQ ID NO: 49:

(i) SEQUENCE CHARACTERISTICS:
           (A) LENGTH: 15 BASE PAIRS
           (B) TYPE: NUCLEIC ACID
           (C) STRANDEDNESS: SINGLE
           (D) TOPOLOGY: LINEAR (ix) FEATURE:
           (D) OTHER INFORMATION: OLIGOMER ADR-1

(xi) SEQUENCE DESCRIPTION: SEQ ID NO: 49:

GGCTGGGATC TAGGC                                                           15

(2) INFORMATION FOR SEQ ID NO: 50:

(i) SEQUENCE CHARACTERISTICS:
           (A) LENGTH: 36 BASE PAIRS
           (B) TYPE: NUCLEIC ACID
           (C) STRANDEDNESS: SINGLE
           (D) TOPOLOGY: LINEAR (ix) FEATURE:
           (D) OTHER INFORMATION: OLIGOMER ADR-2

(xi) SEQUENCE DESCRIPTION: SEQ ID NO: 50:

CACCACACAG ATCTGGGGGG TCTGCTCCTG TGGGGA                                    36

(2) INFORMATION FOR SEQ ID NO: 51:

(i) SEQUENCE CHARACTERISTICS:
           (A) LENGTH: 36 BASE PAIRS
           (B) TYPE: NUCLEIC ACID
           (C) STRANDEDNESS: SINGLE
           (D) TOPOLOGY: LINEAR (ix) FEATURE:
           (D) OTHER INFORMATION: OLIGOMER ADR-3

(xi) SEQUENCE DESCRIPTION: SEQ ID NO: 51:

TTCCATCAGC CGCTTCCTCG GGCGAGCGGC CTCCCT                                    36

(2) INFORMATION FOR SEQ ID NO: 52:

(i) SEQUENCE CHARACTERISTICS:
        (A) LENGTH: 36
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER ADR-4

(xi) SEQUENCE DESCRIPTION: SEQ ID NO: 52:

```
CGAGTGTCGA CAAAAATGTC CACACAGGAG CAGACC                        36
```

(2) INFORMATION FOR SEQ ID NO: 53:

(i) SEQUENCE CHARACTERISTICS:
        (A) LENGTH: 36 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: OLIGOMER ADR-5

(xi) SEQUENCE DESCRIPTION: SEQ ID NO: 53:

```
CGTGCTCGAG GTACCTCAGT GCCCCAGCAG CCGCAG                        36
```

(2) INFORMATION FOR SEQ ID NO: 54:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (ix) FEATURE:
        (D) OTHER INFORMATION: SYNTHETIC OLIGOMER
            USED TO SCREEN BOVINE ADRENAL CORTEX
            cDNA LIBRARY (xi) SEQUENCE DESCRIPTION: SEQ ID NO: 54:

```
TGCCAGTTCG TAGAGCACAT TGGTGCGTGG CGGGTTAGTG                    40
ATGTCCAGGT                                                     50
```

(2) INFORMATION FOR SEQ ID NO: 55:

(i) SEQUENCE CHARACTERISTICS:
        (A) LENGTH: 18 BASE PAIRS
        (B) TYPE: NUCLEIC ACID
        (C) STRANDEDNESS: DOUBLE
        (D) TOPOLOGY: UNKNOWN (ix) FEATURE:
        (D) OTHER INFORMATION: REGION OF ADR cDNA
            HOMOLOGOUS TO PRIMERS, FIGURE 40

(xi) SEQUENCE DESCRIPTION: SEQ ID NO: 55:

```
CAGCACTTCT CCACACAG                                            18
```

(2) INFORMATION FOR SEQ ID NO: 56:

(i) SEQUENCE CHARACTERISTICS:
        (A) LENGTH: 18 BASE PAIRS
        (B) TYPE: NUCLEIC ACID
        (C) STRANDEDNESS: DOUBLE
        (D) TOPOLOGY: UNKNOWN (ix) FEATURE:

(D) OTHER INFORMATION: REGION OF ADR cDNA
            HOMOLOGOUS TO PRIMERS, FIGURE 40

(xi) SEQUENCE DESCRIPTION: SEQ ID NO: 56:

GGGCACTGAG CCTAGATC                                                  18

(2) INFORMATION FOR SEQ ID NO: 57:

(i) SEQUENCE CHARACTERISTICS:
        (A) LENGTH:  27 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  PRIMER ADR4,
            FIGURE 40

(xi) SEQUENCE DESCRIPTION: SEQ ID NO: 57:

CGAGTGTCGA CAAAAATGTC CACACAG                                        27

(2) INFORMATION FOR SEQ ID NO: 58:

(i) SEQUENCE CHARACTERISTICS:
        (A) LENGTH:  24 BASE PAIRS
        (B) TYPE:  NUCLEIC ACID
        (C) STRANDEDNESS:  SINGLE
        (D) TOPOLOGY:  LINEAR (ix) FEATURE:
        (D) OTHER INFORMATION:  PRIMER ADR5,
            FIGURE 40

(xi) SEQUENCE DESCRIPTION: SEQ ID NO: 58:

GGGCACTGAG GTACCTCGAG CACG                                           24

(2) INFORMATION FOR SEQ ID NO: 59:

(i) SEQUENCE CHARACTERISTICS:
        (A) LENGTH:  25 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 59:

GCGCTCAGCG GCCGCTTTCC AGTCG                                          25

(2) INFORMATION FOR SEQ ID NO: 60:

(i) SEQUENCE CHARACTERISTICS:
        (A) LENGTH:  21 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 60:

AATTGCGGCC GCGTACGTAT G                                              21

(2) INFORMATION FOR SEQ ID NO: 61:

(i) SEQUENCE CHARACTERISTICS:
        (A) LENGTH:  21 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 61:

AATTCATACG TACGCGGCCG C                                              21

(2) INFORMATION FOR SEQ ID NO: 62:

(i) SEQUENCE CHARACTERISTICS:
        (A) LENGTH: 55 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 62:

```
GAATTCATAC GTACGCGGCC GCAATTGCGG CCGGTACGTA          40

TAATTCACTG GCCGT                                     55
```

(2) INFORMATION FOR SEQ ID NO: 63:

(i) SEQUENCE CHARACTERISTICS:
        (A) LENGTH: 14 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 63:

```
CAACGCGTCC TAGG                                      14
```

(2) INFORMATION FOR SEQ ID NO: 64:

(i) SEQUENCE CHARACTERISTICS:
        (A) LENGTH: 22 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 64:

```
AATTCCTAGG ACGCGTTGAG CT                             22
```

(2) INFORMATION FOR SEQ ID NO: 65:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 65:

```
GATCCGCAGA TATCATCTAG ATCCCGGGTA GAT                 33
```

(2) INFORMATION FOR SEQ ID NO: 66:

(i) SEQUENCE CHARACTERISTICS:
        (A) LENGTH: 39 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 66:

```
AGAGCTCAAG ATCTACCCGG GATCTAGATG ATATCTGCG           39
```

(2) INFORMATION FOR SEQ ID NO: 67:

(i) SEQUENCE CHARACTERISTICS:
        (A) LENGTH: 34 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 67:

```
CTTGAGCTCT ACGCAGCTGG TCGACACCTA GGAG                                            34

(2) INFORMATION FOR SEQ ID NO: 68:

(i) SEQUENCE CHARACTERISTICS:
        (A) LENGTH:  28 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 68:

AATTCTCCTA GGTGTCGACC AGCTGCGT                                                   28

(2) INFORMATION FOR SEQ ID NO: 69:

(i) SEQUENCE CHARACTERISTICS:
        (A) LENGTH:  40 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 69:

GCGGATCTGC TCGAAGATTG CCTGCGCGTT GGGCTTGATC                                      40

(2) INFORMATION FOR SEQ ID NO: 70:

(i) SEQUENCE CHARACTERISTICS:
        (A) LENGTH:  15 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 70:

TCGACGGACG CGTGG                                                                 15

(2) INFORMATION FOR SEQ ID NO: 71:

(i) SEQUENCE CHARACTERISTICS:
        (A) LENGTH:  14 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 71:

TCGACCACGC GTCC                                                                  14

(2) INFORMATION FOR SEQ ID NO: 72:

(i) SEQUENCE CHARACTERISTICS:
        (A) LENGTH:  35 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 72:

TGGCCGTCGT TTTACTCCTG CGCCTGATGC GGTAT                                           35

(2) INFORMATION FOR SEQ ID NO: 73:

(i) SEQUENCE CHARACTERISTICS:
        (A) LENGTH:  15 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO: 73:

GGCCGCAAAA CCAAA                                                                 15
```

(2) INFORMATION FOR SEQ ID NO: 74:

(i) SEQUENCE CHARACTERISTICS:
        (A) LENGTH: 15 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 74:

AGCTTTTGGT TTTGC                                              15

(2) INFORMATION FOR SEQ ID NO: 75:

(i) SEQUENCE CHARACTERISTICS:
        (A) LENGTH: 20 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 75:

GATCTATCGA TGCGGCCGCG                                     20

(2) INFORMATION FOR SEQ ID NO: 76:

(i) SEQUENCE CHARACTERISTICS:
        (A) LENGTH: 20 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 76:

CGCGCGCGGC CGCATCGATA                                     20

(2) INFORMATION FOR SEQ ID NO: 77:

(i) SEQUENCE CHARACTERISTICS:
        (A) LENGTH: 14 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 77:

AATTGGACGC GTCC                                              14

(2) INFORMATION FOR SEQ ID NO: 78:

(i) SEQUENCE CHARACTERISTICS:
        (A) LENGTH: 12 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 78:

CACAAGCTTG TG                                                  12

(2) INFORMATION FOR SEQ ID NO: 79:

(i) SEQUENCE CHARACTERISTICS:
        (A) LENGTH: 12 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 79:

TCGAGGGAAG CT                                                  12